US007425548B2

(12) United States Patent
Nair et al.

(10) Patent No.: US 7,425,548 B2
(45) Date of Patent: Sep. 16, 2008

(54) MATERIALS AND METHODS FOR IMMUNE SYSTEM STIMULATION

(75) Inventors: P.K. Raveendran Nair, Miami, FL (US); Steven J. Melnick, Miami, FL (US); Cheppail Ramachandran, Miami, FL (US)

(73) Assignee: Variety Chidren's Hospital, Miami, FL (US)

( * ) Notice: Subject to any disclaimer, the term of this patent is extended or adjusted under 35 U.S.C. 154(b) by 456 days.

(21) Appl. No.: 11/178,620

(22) Filed: Jul. 11, 2005

(65) Prior Publication Data

US 2006/0009501 A1  Jan. 12, 2006

Related U.S. Application Data

(60) Provisional application No. 60/586,548, filed on Jul. 9, 2004.

(51) Int. Cl.
*A61K 31/716* (2006.01)
*C07H 1/08* (2006.01)

(52) U.S. Cl. ..................... 514/60; 536/123.12; 536/128
(58) Field of Classification Search .................. None
See application file for complete search history.

(56) References Cited

U.S. PATENT DOCUMENTS

| | | | |
|---|---|---|---|
| 5,166,379 A | 11/1992 | Coval et al. | |
| 5,529,778 A | 6/1996 | Rohatgi | |
| 5,683,698 A | 11/1997 | Chavali et al. | |
| 6,379,721 B1 | 4/2002 | Sengupta et al. | |
| 6,451,354 B1 | 9/2002 | Hebert et al. | |
| 6,582,733 B1 | 6/2003 | Pruthi | |
| 2002/0142055 A1 | 10/2002 | De Souza et al. | |
| 2004/0009240 A1 | 1/2004 | Solanki | |
| 2004/0033273 A1 | 2/2004 | Patwardhan et al. | |

FOREIGN PATENT DOCUMENTS

| | | |
|---|---|---|
| CA | 2 432 488 A1 | 7/2002 |
| GB | 2 314 270 | 12/1997 |
| IN | 184422 | 1/1993 |
| IN | 183192 | 1/1994 |
| IN | 183805 | 10/1998 |
| IN | 183 487 | 1/2000 |
| WO | WO 02/053166 A1 | 7/2002 |

OTHER PUBLICATIONS

Rao, E. et al "Studies on the polysaccharide preparation (guduchisatwa) derived from *Tinospora cordifolia*" Ind. J. Pharm. Sci. May-Jun. 1981 pp. 103-105.*
Adachi, Y. et al. "Characterization of β-glucan recognition site on C-type lectin, dectin 1" *Infect Immun.*, 2004, 72:4159-4171.
Akira, S. and Sato, S. "Toll-like receptors and their signaling mechanisms" *Scand. J. Infect. Dis.*, 2003, 35:555-562.
Akira, S. "Toll-like receptor signaling" *J. Biol. Chem.*, 2003, 278:38105-38108.

Atal, C.K. et al. "Immunomodulating agents of paint origin. I: Preliminary screening" *J. Ethnopharmacology*, 1986; 18:133-141.
Auphan, N. et al. "Immunosuppression by glucocorticoids: inhibition of NF-κB activity through induction of IκB synthesis" *Science*, 1995, 270:286-290.
Bao, X. et al. "Chemical modifications of the (1→3)-α-D-glucan from spores of *Ganoderma lucidum* and investigation of their physicochemical properties and immunological activity" *Carbohyd. Res.*, 2001, 336:127-140.
Beutler, B. et al. "How we detect microbes and respond to them: the Toll-like receptors and their transducers" *J Leukocyte Biol.*, 2003, 74:479-485.
Bohn, J.A. and Bemiller, N. "(1→3)-β-D-glucans as biological response modifiers: a review of structure-functional activity relationships" *Carbohydr. Polymers*, 1995, 28:3-14.
Brown, G.D. and Gordon, S. "A new receptor for β-glucans" *Nature*, 2001, 413:36-37.
Brown, G.D. and Gordon, S. "Fungal β-glucans and mammalian immunity" *Immunity*, 2003:19:311-315.
Brown, G.D. et al. "Dectin-1 is a major β-glucan receptor on macrophages" *J. Exp. Med.*, 2002, 196:407-412.
Le Cabec, V. et al. "Nonopsonic phagocytosis of zymosan and *Mycobacterium kansasil* by CR3 (CD11b/CD18) involves distinct molecular determinants and is or is not coupled with NADPH oxidase activation" *Infect. Immunity*, 2000, 68:4736-4745.
Chintalwar, G. et al. "An immunologically active arabinogalactan from *Tinospora cordifolia*" *Phytochemistry*, 1999, 52:1089-1093.
Czop, J.K. and Austen, K.F. "A β-glucan inhibitable receptor on human monocytes: its identity with the phagocytic receptor for particulate activators of the alternative complement pathway" *J. Immunol.*, 1985, 134:2588-2593.
Dahanukar, S.A. et al. "Immunotherapeutic modification by *Tinospora cordifolia* of abdominal sepsis induced by caecal ligation in rats" *Ind. J. Gastroenterology*, 1988, 7(1):21-23.
Desai, V.R. et al. "An immunomodulator from *Tinospora cordifolia* with antioxidant activity in cell-free systems" *Proc. Indian Acad. Sci.*, 2002, 114:713-719.
Dhuley, J.N. "Effect of some Indian herbs on macrophage functions in ochratoxin A treated mice" *J. Ethnopharmacology*, 1997, 58:15-20.
Diwanay, S. et al. "Immunoprotection by botanical drugs in cancer chemotherapy" *J. Ethnopharmacology*, 2004, 90:49-55.

(Continued)

*Primary Examiner*—Leigh C Maier
(74) *Attorney, Agent, or Firm*—Saliwanchik, Lloyd & Saliwanchik

(57) ABSTRACT

The subject invention concerns a novel polysaccharide. RR1 is an α-D-glucan polysaccharide composed of a (1→4) linked back bone and (1→6) linked branches, which has been isolated from a medicinal herb, *Tinospora cordifolia*. RR1 exhibits unique immune-stimulating properties, is non-cytotoxic, and non-proliferating to normal lymphocytes, as well as tumor cell lines. The subject invention also concerns compositions containing an RR1 compound and methods for modulating an immune response in a subject using RR1 compounds. The present invention also provides methods for the use of an RR1 compound in conjunction with an antigen to stimulate an immune response, the RR1 compound providing an adjuvant-like activity in the generation of a Th1-type immune response to the antigen.

20 Claims, 20 Drawing Sheets

OTHER PUBLICATIONS

Gangan, V.D. et al. "Cordifolisides A, B, C: Norditerpene furan glycosides from *Tinospora cordifolia*" *Phytochemistry*, 1994, 37(3):781-786.

Gantner, B.N. et al. "Collaborative induction of inflammatory responses by dectin-1 and Toll-like receptor 2" *J. Exp. Med.*, 2003, 197:1107-1117.

Gao, J.J. et al. "Bacterial DNA and lipoplysaccharide induce synergistic production of TNF-α through a post-transcriptional mechanism" *J. Immunol*, 2001, 166:6855-6860.

Ghosh, S, and Karin, M. "Missing pieces in the NF-κB puzzle" *Cell*, 2002, 109:S81-S96.

Ghosh, S. et al. "NF-κB and rel proteins: evolutionarily conserved mediators of immune responses" *Annu Rev Immunol.*, 1998, 16:225-260.

Goel, H.C. et al. "Free radical scavenging and metal chelation by *Tinospora cordifolia*, a possible role in radioprotection" *Ind J Exp Biol*, 2002, 40:727-737.

Goel, V. et al. "Echinacea stimulates macrophage function in the lung and spleen of normal rats" *J. Nutri. Biochem*, 2002, 13:487-492.

Goldman, R. "Characteristics of the β-glucan receptor of murine macrophages" *Exp. Cell Res.*, 1988, 174:481-490.

Hetland, G. "Anti-infective action of immuno-modulating polysaccharides (β-glucan and *Plantago Major* L. Pectin) against intracellular (*Mycobacteria sp.*) and extracellular (*Streptococcus pneumoniae* sp.) respiratory pathogens" *Curr. Med. Chem.*, 2003, 2:135-146.

Jagetia, G.C. et al. "Evaluation of the antineoplastic activity of guduchi (*Tinospora cordifolia*) in cultured HeLa cells" *Cancer Letters*, 1998, 127:71-82.

Jahfar, M. "Glycosyl composition of polysaccharide from *Tinospora cordifolia*" *Acta Pharm*, 2003, 53:65-69.

Jahfar, M. and Azadi, P. "Glycosyl composition of polysaccharide from *Tinospora cordifolia*. II. Glycosyl linkages" *Acta Pharm*, 2004, 54:73-78.

Kandimalla, E.R. et al. "A dinucleotide motif in oligonucleotides shows potent immunomodulatory activity and overrides species-specific recognition observed with CpG motif" *Proc. Natl. Acad. Sci. USA*, 2003, 100:14303-14308.

Kapil, A. and Sharma, S. "Immunopotentiating compounds from *Tinospora cordifolia*" *J Ethnopharmacology*, 1997. 58:89-95.

Kim, H.S. et al. "In vitro chemopreventive effects of plant polysaccharides (*Aloe barbadensis Miller, Lentinus edodes, Ganoderma lucidum* and *Coriolus versicolor*)" *Carcinogenesis*, 1999, 20:1637-1640.

Kulicke, W-M. et al. "Correlation between immunological activity, molar mass, and molecular structure of different (1→3)-β-D-glucans" *Carbohydr. Res.*, 1997, 297:135-143.

Lebron, F. et al. "*Pneumocystis carinii* cell wall β-glucans initiate macrophage inflammatory responses through NF-κB activation" *J Biol Chem.*, 2003, 278:25001-25008.

Leyon, P.V. and Kuttan, G. "Inhibitory effect of a polysaccharide from *Tinospora cordifolia* on experimental metastasis" *J. Ethnopharmacology*, 2004, 90:233-237.

Li, R.W. et al. "Anti-inflammatory activity, cytotoxicity and active compounds of *Tinospora smilacina* benth" *Phytotherapy Res*, 2004, 18:78-83.

Manjrekar, P.N. et al. "Comparative studies of the immunomodulatory activity of *Tinospora cordifolia* and *Tinospora sinensis*" *Fitoterapia*, 2000, 71:254-257.

Martin, T.S. et al. "Furanoid diterpene glucosides from *Tinospora rumphii*" *Phytochemistry*, 1996, 42:153-158.

Marx, J. "How the glucocorticoids suppress immunity" *Science*, 1995, 270:232-233.

Mathew, S. and Kuttan, G. "Antioxidant activity of *Tinospora cordifolia* and its usefulness in the amelioration of cyclophosphamide induced toxicity" *J Exp Clin Cancer Res*, 1997, 16:407-411.

Morrison, D.C. and R.J. Ulevitch "The effects of bacterial endotoxins on host mediation systems" *Am. J. Pathol.*, 1978, 93:526-617.

Mueller, A et al. "The influence of glucan polymer structure and solution conformation on binding to (1→3)-β-D-glucan receptors in a human monocyte-like cell line" *Glycobiology*, 2000, 10:339-346.

Mukhopadhyay, S. et al. "The potential for Toll-like receptors to collaborate with other innate immune receptors" *Immunol.*, 2004, 112:521-530.

Nair, P.K. et al. "Immune stimulating properties of a novel polysaccharide from the medicinal plant *Tinopsora cordifolia*" *Int. Immunopharmacol.*, 2004, 4:1645-1659.

Nemmani, K.V. et al. "Cell proliferation and nature killer cell activity by polyherbal formulation, Immu-21 in mice" *Ind J Exp Biol*, 2002, 40:282-287.

Nono, I. et al. "Oxidative degradation of an antitumor (1-3)β-D-glucan, grifolan" *J. Pharmacobio-Dyn.*, 1991, 14:9-19.

Noor, H. and Ashcroft, S. "Pharmacological characterization of the antihyperglycaemic properties of *Tinospora crispa* extract" *J. Ethnopharmacology*, 1998, 62:7-13.

O'Connell, M.A. et al. "Role of IKK1 and IKK2 in lipopolysaccharide signaling in human monocytic cells" *J. Biol. Chem.*, 1998, 273:30410-30414.

Parham, P. "The unsung heroes" *Nature*, 2003, 423:20.

Prince, P.S.M. and Menon, V.P. "Antioxidant activity of *Tinospora cordifolia* roots in experimental diabetes" *J. Ethnopharmacology*, 1999, 65:277-281.

Prince, P.S.M. and Menon, V.P. "Antioxidant action of *Tinospora cordifolia* root extract in alloxan diabetic rats" *Phytother Res.*, 2001, 15:213-218.

Prince, P.S.M. and Menon, V.P. "Hypoglycaemic and hypolipidaemic action of alcohol extract of *Tinospora cordifolia* roots in chemical induced diabetes in rats" *Phytother Res.*, 2003, 17:410-413.

Prince, P.S.M. et al. "Hypolipidaemic action of *Tinospora cordifolia* roots in alloxan diabetic rats" *J. Ethnopharmacology*, 1999, 64:53-57.

Ramachandran, C. et al. "Ayurvedic Herbal Derivatives. Anti-cancer drug Amooranin immunostimulatory polysaccharide RR-1" presented at the Children's Oncology Group meeting in Dallas, TX on Nov. 5, 2003.

Ramachandran, C. et al. "Ayurvedic Herbal Derivatives: update. Anti-cancer drug Amooranin immunostimulatory polysaccharide RR-1" presented at the Children's Oncology Group meeting in Washington, D.C. on Apr. 2, 2004.

Ramachandran, C. et al. "The novel α-glucan RR1 from *Tinospora cordifolia* stimulates the immune system through NF-κB activated cytokine synthesis in macrophages" presented at the AACR International Conference on Frontiers in Cancer Prevention Research in Seattle, WA on Oct. 11-20, 2004.

Rege, N. et al. "Immunotherapy with *Tinospora cordifolia*: a new lead in the management of obstructive jaundice" *Ind J Gastroenterol*, 1993, 12:5-8.

Rege, N.N. et al. "Modulation of immunosuppression in obstructive jaundice by *Tinospora cordifolia*" *Ind J Med Res*, 1989, 90:478-483.

Rege, N.N. et al. "Adaptogenic properties of six *Rasayana* herbs used in ayurvedic medicine" *Phytother Res*, 1999, 13:275-291.

Ross, G.D. et al. "Specificity of membrane complement receptor type three ($CR_3$) for β-glucans" *Complement*, 1987, 4:61-74.

Ross, G.D. et al. "Therapeutic intervention with complement and β-glucan in cancer" *Immunopharmacology*, 1999, 42:61-74.

Sarma, D.N.K. et al. "Isolation of jatrorrhizine from *Tinospora cordifolia* roots" *Planta Med*, 1995, 61:98-99.

Singh, S.S. et al. "Chemistry and medicinal properties of *Tinospora cordifolia* (Guduchi)" *Ind. J. Pharm.*, 2003, 35:83-91.

Sohni, Y.R. and Bhatt, R.M. "Activity of a crude extract formulation in experimental hepatic amoebiasis and in immunomodulation studies" *J. Ethnopharmacology*, 1996, 54:119-124.

Subramanian, M. et al. "Antioxidant properties of a *Tinospora cordifolia* polysaccharaide against iron-mediated lipid damage and γ-ray induced protein damage" *Redox. Rep.*, 2002, 7:137-143.

Suda, M. et al. "Kupffer cells play important roles in the metabolic degradation of a soluble anti-tumor (1→3)-β-D-glucan, SSG, in mice" *FEMS Immunol. Med. Microbiol.*, 1996, 15:93-100.

Swaminathan, K. et al. "Structure of columbin, a diterpenoid furanolactone from *Tinospora cordifolia* miers" *Acta Cryst.*, 1989, C45(Pt2):300-303.

Thatte, U.M. and Dahanukar, S.A. "Comparative study of immunomodulating activity of Indian medicinal plants, lithium carbonate and glucan" *Meth Find Exp Clin Pharmacol*, 1988, 10:639-644.

Thatte, U.M. et al. "Immunotherapteutic modification of *Escherichia coli* peritonitis and bacterernia by *Tinospora cordifolia*" *J. Postgrad Med*, 1992, 38:13-15.

Thatte, U.M. et al. "*Tinospora cordifolia* induces colony stimulating activity in serum" *J. Postgrad Med*, 1994, 40:202-203.

Thornton, B.P. et al. "Analysis of the sugar specificity and molecular location of the β-glucan-binding lectin site of complement receptor type 3 (CD11b/CD18)" *J. Immunol.*, 1996, 156:1235-1246.

Williams, D.L. et al. "Glucan-based macrophage stimulators" *Clin. Immunotherapy*, 1996, 5:392-399.

Williams, D.L. et al. "Inhibition of LPS-induced NFκB activation by a glucan ligand involves down-regulation of IKKβ kinase activity and altered phosphorylation and degradation of IκBα" *Shock*, 2000, 13:446-452.

Williams, D.L. et al. "Inhibiting early activation of tissue nuclear factor-κB and nuclear factor interleukin 6 with (1→3)-β-D-glucan increases long-term survival in polymicrobial sepsis" *Surgery*, 1999, 126:54-65.

Williams, D.L. "Overview of (1→3)-β-D-glucan Immunobiology" *Mediators Inflamm.*, 1997, 6:247-250.

Willment, J.A. et al. "Characterization of the human β-glucan receptor and its alternatively spliced isoforms" *J. Biol. Chem.*, 2001, 276:43818-43823.

Xia, Y. et al. "The β-glucan-binding lectin site of mouse CR3 (CD11b/CD18) and its function in generating a primed state of the receptor that mediates cytotoxic activation in response to IC3b-opsonized target cells" *J. Immunol.*, 1999, 162:2281-2290.

Young, S.H. et al. "Molecular mechanism of tumor necrosis factor-α production in 1→3-β-glucan (zymosan)-activated macrophages" *J. Biol Chem.*, 2001, 276:20781-20787.

Chauhan, R.S. *J. Immunology & Immunopathology*, 1999, 1(1/2):54-57, abstract.

Chopra, R.N. I.C. Chopra, K.D. Handa, L.D Kanpur (Editors), 1982, Glossary of Indian Medicinal Plants; Council of Scientific an Industrial Research, New Delhi, Dhar VN & Sons, Kolkata, India.

* cited by examiner 0    15'    30'    60'

I-κBα⟶

MATERIALS AND METHODS FOR IMMUNE SYSTEM STIMULATION

CROSS-REFERENCE TO RELATED APPLICATION

The present application claims benefit of U.S. Provisional Application Ser. No. 60/586,548, filed Jul. 9, 2004, which is hereby incorporated by reference herein in its entirety, including any figures, tables, nucleic acid sequences, amino acid sequences, and drawings.

BACKGROUND OF THE INVENTION

The possibility of bio-terrorism, outbreak of Severe Acute Respiratory Syndrome (SARS) and Bird Flu virus, continuing spread of HIV/AIDS, and the emergence of pathogenic strains resistant against current medications compel investigators to look for new protective measures including biodefense strategies against these threats. Immune activation is an effective as well as protective approach for biodefense strategies for emerging infectious diseases (Hackett, C. J. *J. Allergy and Clin. Immunol.*, 2003, 112:686-694). Although the human immune system possesses a wide array of microbial detection and host defense mechanisms, pathogen evasion of the immune surveillance and destruction system is the norm. The situation is not different with cancer, as most of the tumor cells are not detected and escape immune surveillance (Wajchman, H. J. et al. *Cancer Res.*, 2004, 64:1171-1180).

It is the innate immune system components that detect the pathogens or the non-self intruders, with the help of the specific receptors, and respond immediately by activation of the immune competent cells, synthesis of cytokines and chemokines, and release of inflammatory mediators to eliminate or contain the intruders. Innate immune activation also triggers and paves the way for the adaptive immune response by antigen-specific T and B lymphocytes. The natural killer (NK) cells play a decisive role in the innate immune defense against virus infected and malignant cells by virtue of their ability to recognize and destroy abnormal cells, pending the development of adaptive immunity (Smith, H. R. et al. *Proc. Natl. Acad. Sci. USA*, 2002, 99:8826-8831; Moser, J. M. et al. *Curr. Opin. Immunol.*, 2002, 14:509-516).

Several compounds activate the immune system, such as microbial lipopolysaccharides (LPS), double-stranded RNA and DNA oligonucleotides containing unmethylated CpG motifs have been reported earlier (Hackett, C. J. *J. Allergy and Clin. Immunol.*, 2003, 112:686-694; Kandimalla, E. R. et al. *Proc. Natl. Acad. Sci. USA*, 2003, 100:14303-14308). Stimulation of multiple receptors is reported to exhibit synergistic effect in cytokine production (Gao, J. J. et al. *J. Immunol.*, 2001, 166:6855-6860). The complement activation cascade is another integral part of the innate immune system in which the cellular pathogens, such as intracellular bacteria, are coated with complement components (opsonization) and readily undergo phagocytosis. Thus, complement activation plays an important role in microbial killing and is essential for transport and clearance of immune complexes.

The type of adaptive immune response (also known as the specific or acquired immune response) that is generated to infection or other antigenic challenge can generally be distinguished by the subset of T helper (Th) cells involved in the response. The Th1 response (the cellular or cell-mediated response) is responsible for classical cell-mediated functions such as delayed-type hypersensitivity and activation of cytotoxic T lymphocytes (CTLs), whereas the Th2 response (the humoral response) functions more effectively as a helper for B-cell activation. The type of immune response to an antigen is generally determined by the cytokines produced by the cells responding to the antigen. Differences in the cytokines secreted by Th1 and Th2 cells are believed to reflect different biological functions of these two subsets.

It has become clear that cytokines play crucial roles in regulating various aspects of immune responses. Among the cytokines, interleukin (IL)-12 plays a central role in coordinating innate and cell-mediated adaptive immunity (Watford, W. T. et al. *Cytokine Growth Factor Rev.*, 2003, 14:361-368). Prophylactic as well as post-exposure protection by immune stimulation have been demonstrated (Walker, P. S. et al. *Proc. Natl. Acad. Sci. USA*, 1999, 96:6970-6975; Juffermans, N. P. et al *Infect. Immunol.*, 2002, 70:147-152). Usually, these protective measures are correlated with synthesis of IL-12 and interferon (IFN)-γ, the cytokines of the Th1 pathway of T cell differentiation associated with the adaptive immune system (Gramzinski, A. M. et al. *Infect. Immunol.*, 2001, 69:1643-1649).

The Th1 subset may be particularly suited to respond to viral infections and intracellular pathogens because it secretes IL-2 and IFN-gamma, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and, therefore, one type of response can moderate the activity of the other type of response. A shift in the Th1/Th2 balance can result in an allergic response, for example, or, alternatively, in an increased CTL response.

Immunization of a host animal against a particular antigen has been accomplished traditionally by repeatedly vaccinating the host with an immunogenic form of the antigen. While most current vaccines elicit effective humoral (antibody, or "Th2-type") responses, they fail to elicit cellular responses (in particular, major histocompatibility complex (MHC) class I-restricted CTL, or "Th1-type" responses) which are generally absent or weak. For many infectious diseases, such as tuberculosis and malaria, Th2-type responses are of little protective value against infection. Moreover, antibody responses are inappropriate in certain indications, most notably in allergy where an antibody response can result in anaphylactic shock. Proposed vaccines using small peptides derived from the target antigen and other currently used antigenic agents that avoid use of potentially infective intact viral particles, do not always elicit the immune response necessary to achieve a therapeutic effect. The lack of a therapeutically effective human immunodeficiency virus (HIV) vaccine is an unfortunate example of this failure.

Innate immunity mediated by macrophages, neutrophils and natural killer (NK) cells is the first line of host defense mechanism against microbial invasion. The innate immune system targets the structurally conserved pathogen-associated molecular patterns (PAMPs) through specific germ-line encoded receptors called pattern recognition receptors (PRRs) (Aderem, A. and Ulevitch, R. J. *Nature*, 2000, 406: 782-787). Augmentation of the immune system with natural as well as synthetic immune stimulators offers a distinct advantage over conventional therapies especially with weakened immune system and antibiotic resistance.

Several preclinical and clinical investigations have indicated the usefulness of β-glucans, a class of biological response modifiers (BRMs), for acceleration of wound healing and against orchestration of the systemic inflammatory response syndrome and septic shock (Ross, G. D. et al. *Immunopharmacology*, 1999, 42:61-74; Williams, D. L. *Mediators*

Inflamm., 1997, 6:247-250; Hetland, G. Curr. Med. Chem., 2003, 2:135-146). β-glucans are potent stimulators of innate immune system in invertebrates, while in mammals they are potent activators of the complement system. These polymers have therapeutic potential because of their effects on the immune system that may include anti-tumor and anti-infective activities as well as protection against fungal, bacterial, viral, and protozoan infections. Soluble and particulate β-glucans interact with cognate receptors on macrophages stimulating the syntheses of cytokines, chemokines and reactive oxygen intermediates (Ganter, B. N. et al. J. Expt. Med., 2003, 197:1107-1117). The major receptors reported for β-glucan recognition/binding on macrophages are complement receptor 3 (CD11b/CD18 or CR3), Dectin-1 and Toll-like receptors (TLRs) 2 and 6. Although lactosylceramide and scavenger receptors are also identified in β-glucan recognition, their function is not well-documented (Willment, J. A. et al. J. Biol. Chem., 2001, 276:43813-43823).

Toll like receptors (TLRs) are part of the large super family of Toll-Interleukin (IL)-1 receptors (TIRs) possessing the cytoplasmic motif for the intracellular signaling function. These molecules provide a first line host defense and have been implicated in infectious and autoimmune diseases in a variety of organisms ranging from flies to mammals. It is now accepted that TLRs are the principal signaling molecules through which mammals sense infection (Beutler, B. et al. J Leukocyte Biol., 2003, 74:479-485). In mammals, 12 different TLRs have been identified each recognizing distinct PAMPs (Akira, S. and Sato, S. Scand. J. Infect. Dis., 2003, 35:555-562). All TLRs, IL-1 receptor and other TIR domain containing receptors, with the exception of TLR3, share a common signaling pathway that depends on the adaptor myeloid differentiation factor 88 (MyD88) (Ganter, B. N. et al. J. Expt. Med., 2003, 197:1107-1117; Mukhopadhyay, S. et al. Immunol., 2004, 112:521-530). Besides MyD88, several adaptor molecules have recently been reported and the differential utilization of these adaptor molecules may provide the specificity for the TLR signaling (Akira, S. J. Biol. Chem., 2003, 278:38105-38108). Evidence for the physical and/or functional interactions among TLRs, and between TLR and other surface receptors, has become available. Gantner et al. have reported collaborative induction of dectin-1 and TLR by β-glucan stimulation as well as the synergistic interaction between these two receptors on NF-κB activation (Ganter, B. N. et al. J. Expt. Med., 2003, 197:1107-1117).

TLR mediated cytokine production depends on its down stream mediators such as IL-1R-associated kinase (IRAK)-4 and TNF receptor-associated factor-6 (TRAF-6) that activate JNK and nuclear factor (NF)-κB (Akira, S. J. Biol. Chem., 2003, 278:38105-38108). NF-κB is a ubiquitous transcription factor that regulates the cytokine gene expression in many immune effecter cells. In most cells, NF-κB is usually present in cytoplasm as latent, inactive and bound to the inhibitory protein κB (I-κB) (Ghosh, S, and Karin, M., Cell, 2002, 109:S81-96). It is activated by a variety of stimuli such as pro-inflammatory cytokines, viral products, lipopolysaccharides, plant derived compounds such as taxol, as well as pathogen and non-pathogen derived β-glucans (Akira, S. and Sato, S. Scand. J. Infect. Dis., 2003, 35:555-562; Young, S. H. et al. J. Biol. Chem., 2001, 276:20781-20787; Lebron, F. et al. J Biol Chem., 2003, 278:25001-25008). On stimulation, I-κBα is phosphorylated and rapidly degraded through proteasomal mechanisms which in turn release the active NF-κB so as to translocate to the nucleus and bind to DNA to initiate cytokine/chemokine gene transcription (Ghosh, S, and Karin, M., Cell, 2002, 109:S81-96; Auphan, N. et al. Science, 1995, 270:232-233).

Immunostimulating properties of glucans have been ascribed to be due to the β-glycosidic linkages, degree of branching and solution conformation (Mueller, A et al. Glycobiology, 2000, 10:339-346). The present inventors have characterized and reported the immunostimulating properties of a (1,4)-α-D-glucan, RR1, a novel polysaccharide obtainable from the medicinal plant Tinospora cordifolia (Nair, P. K. et al. Int. Immunopharmacol., 2004, 4:1645-1659). This novel α-glucan is water soluble and has (1,4)-α-D-glycosidic linkages in the main chain with a (1,6)-α-D-glycosidic linked side chains at an interval of 6 to 7 glucose units. It is non-cytotoxic to normal cells as well as tumor cell lines (CEM, CEM/VLB) even up to 1000 µg/ml and activates the human lymphocyte subsets at varying levels. The activation of NK cells, one of the major arms of innate immunity, was demonstrated by the increased level of killing of target cells by the RR1-treated lymphocytes in a functional assay. The cytokine profile upon RR1 stimulation demonstrates the much desired Th1 pathway of T helper cell differentiation along with high level of induction of regulatory cytokines which may be a self control mechanism of the over production of Th1 response. Its water solubility, non-cytotoxic nature, and its herbal origin indicate the clinical potential of RR1 for immune stimulation.

BRIEF SUMMARY OF THE INVENTION

The subject invention concerns novel immune system stimulating polysaccharides. One such compound exemplified herein has been isolated from the medicinal plant Tinospora cordifolia and characterized. In one aspect, the subject invention provides a compound having the structure shown in FIG. 3 (also referred to herein as RR1), which is an α-D-glucan polysaccharide composed of a (1→4) linked back bone and (1→6) linked branches, with a molecular mass greater than 550 kDa, exhibiting unique immune-stimulating properties.

The immunostimulant properties of RR1 were ascertained by the analysis of RR1 induced activation of human lymphocytes, NK cell functional activity, phagocytic activity, complement activation, cytokine and chemokine synthesis, induction of inducible nitric oxide synthase (iNOS), nitric oxide production, and oxidative stress measurements. The results clearly demonstrated enhancement of the innate immune system components while the cytokine profile demonstrated the Th1 pathway of the T helper cell differentiation of the antigen-specific cell-mediated (adaptive) immunity. Stimulation with RR1 resulted in a several-fold increase in activation of natural killer (NK) cells, the major effecter cells of the innate immune system, and the activation of the complements in the alternate pathway, which is self amplifying and is important in the recognition and clearance of pathogens in the absence of antibodies. RR1 also enhances the phagocytosis of zymosan particles by macrophages. As described in more detail herein, RR1 also upregulated the synthesis of the Th1 cytokines, IL-12, IL-18, IL-1β, and IFN-γ. RR1 also induced the production of the antitumor cytokine TNF-α and MCP-1, but did not cause any significant induction of iNOS. This upregulation of cytokine synthesis is facilitated by the activation of the NF-κB transcription factor through the phosphorylation of iκB protein. The process of RR1 immuno-stimulation involves receptors such as toll-like receptor (TLR) 6 and dectin-1.

An innate immune system strengthened by administration of RR1 enables a subject to prevent the entry of pathogens while the boosted Th1 cells detect and destroy intracellular pathogens, viruses, and malignant cells. Therefore, RR1 can be used as an immunostimulatory, chemopreventive, and therapeutic agent for a variety of human and animal ailments. RR1 can also be combined with other agent, such as anticancer agents (e.g., monoclonal antibodies) for the chemotherapeutic treatment of cancer patients.

Accordingly, another aspect of the subject invention provides methods for modulating an immune response in a subject. In one embodiment, an RR1 compound (RR1, or a pharmaceutically acceptable salt or analog thereof) is administered to the subject in an amount effective to provide a general stimulation of an immune response through the adjuvant-like effect of the RR1 compound. The present invention also provides methods for the use of an RR1 compound of the invention in conjunction with an antigen to stimulate an immune response. Preferably, as used in such methods, the RR1 compound provides an adjuvant-like activity in the generation of a Th1-type immune response to the antigen.

In another aspect, the subject invention provides immune modulating compositions containing at least one RR1 compound and a pharmaceutically acceptable carrier.

A further aspect of the subject invention provides a process for obtaining RR1 from *Tinospora cordifolia* plant material.

(0, 10, 50 and 100 µg/ml) at 37° C. for 24 hours and secreted IL-8 in the medium was analyzed by ELISA protocol.

Figure 19:
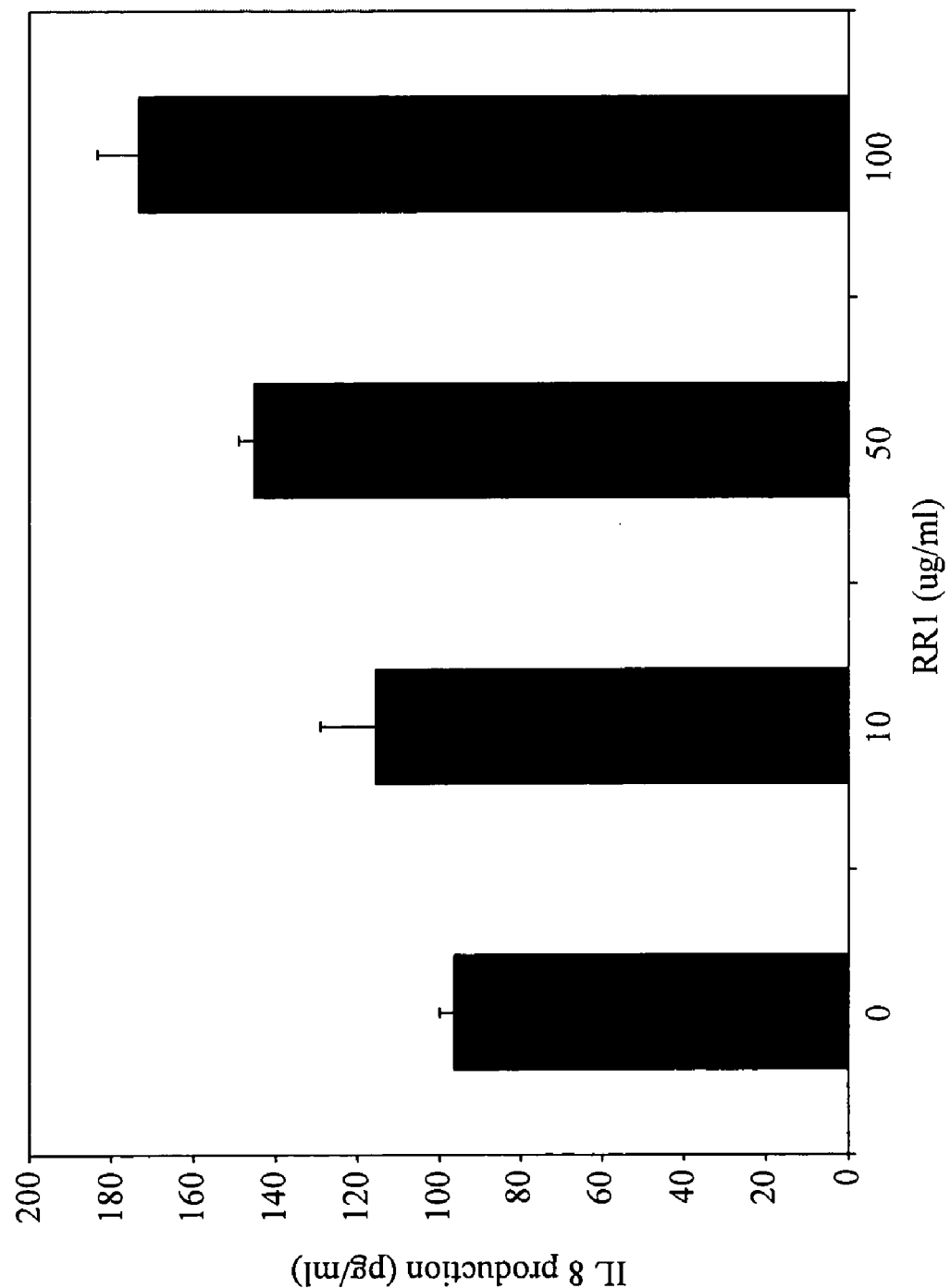

FIG. 19 shows analysis of RR1-induced IL-8 synthesis in HEK293 cells stably transfected with the TLR6 gene. HEK293/TLR6 cells ($1×10^6$) were treated with RR1 (0, 10, 50, and 100 µg/ml) at 37° C. for 24 hours and secreted IL-8 in the medium was analyzed by ELISA protocol.

Figure 20:
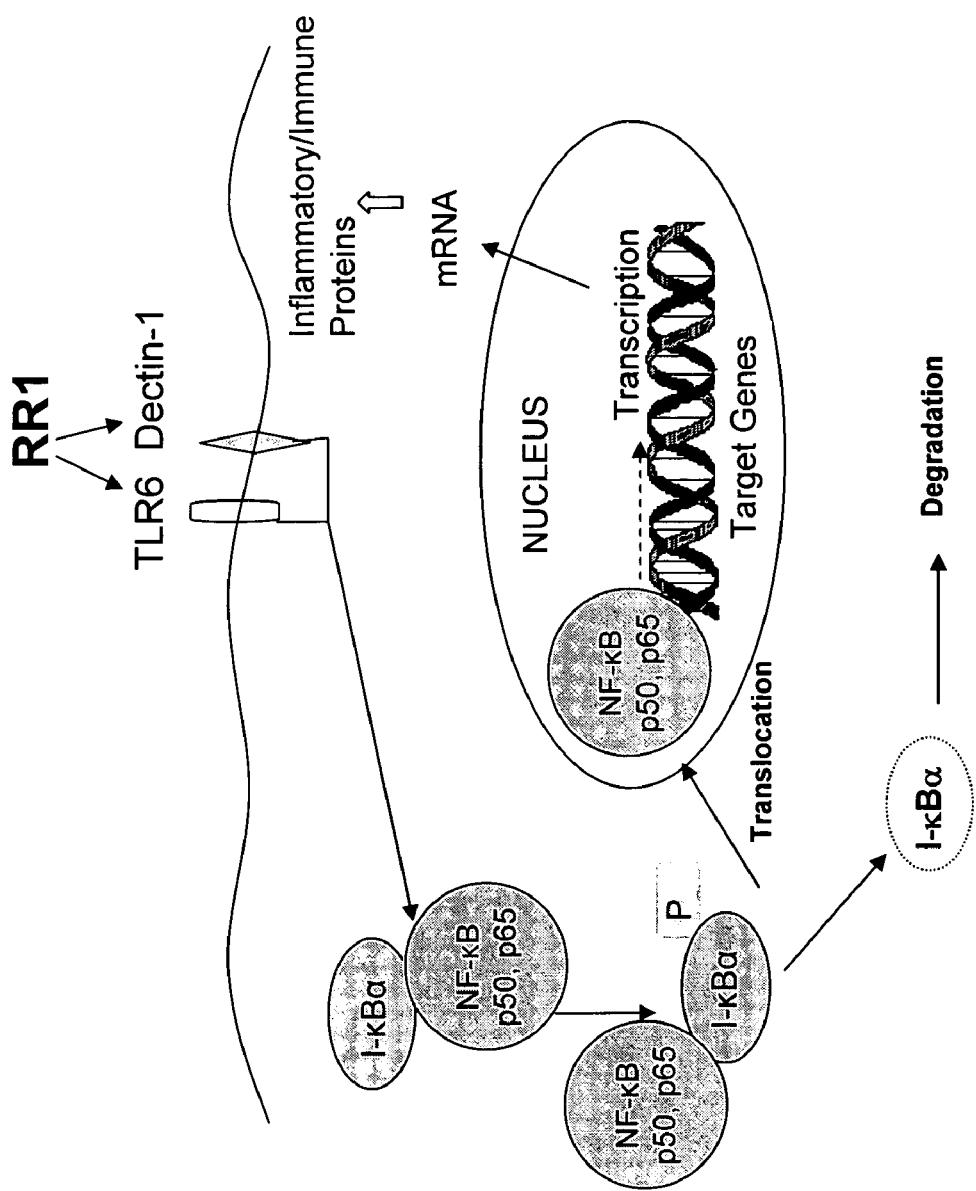

FIG. 20 shows an immune system stimulation pathway of RR1 in macrophages.

DETAILED DESCRIPTION OF THE INVENTION

Figure 3:
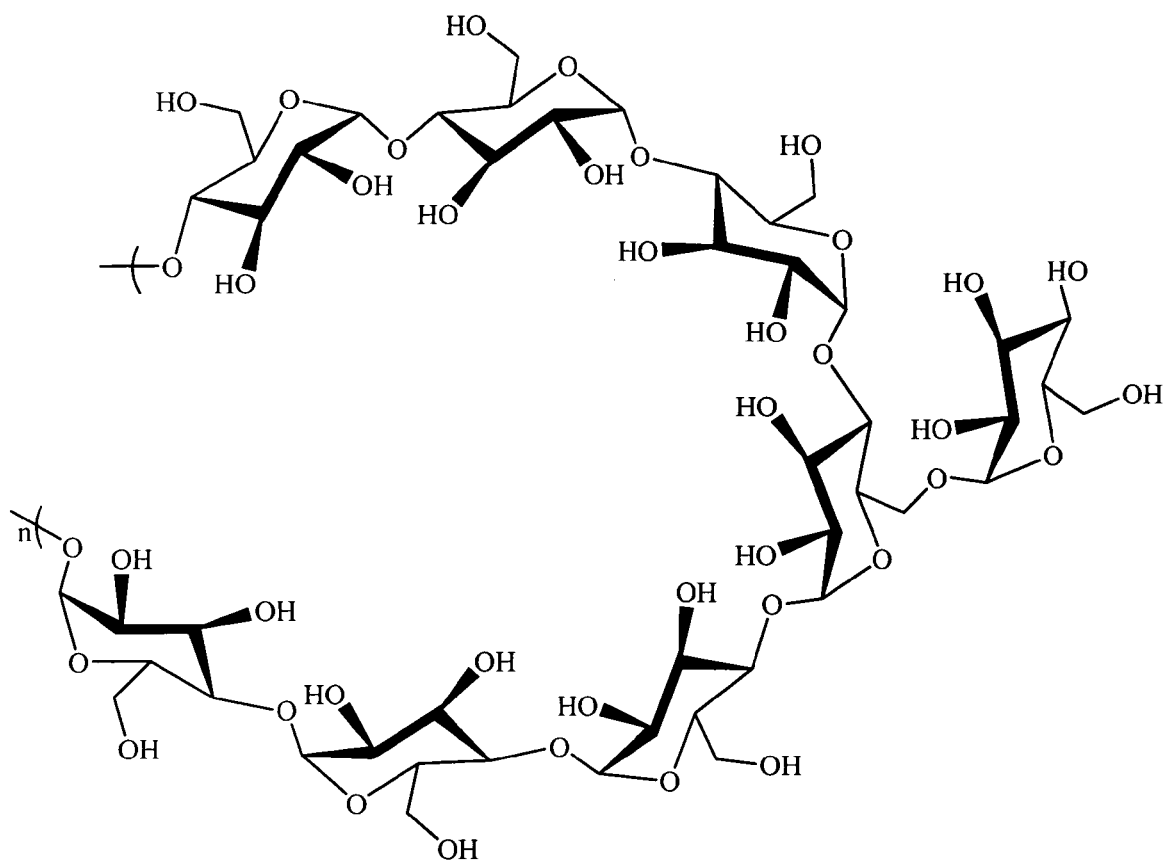
FIG. 3 shows the chemical structure of RR1 ((1,4)-α-D-glucan).

The subject invention provides an isolated compound (RR1), a novel polysaccharide exhibiting unique immune-boosting properties. RR1, which has the structure shown in FIG. 3, is a α-D-glucan polysaccharide composed of a (1→4) linked back bone and (1→6) linked branches, with a molecular mass greater than 550 kDa. RR1 has been isolated from a medicinal herb, *Tinospora cordifolia* (family Minispermaceae), which has been the subject of study for its medicinal properties (Singh, S. S. et al. *Ind. J. Pharm.*, 2003, 35:83-91; Chintalwar, G. et al. *Phytochemistry*, 1999, 52:1089-1094; Manjerakar, P. N. et al. *Fitotherapia*, 2000, 71:254-257; Desai, V. R. et al. *Proc. Indian Acad. Sci.*, 2002, 114:713-719; Subramanyan, M. et al., *Redox. Rep.*, 2002, 7:137-143).

RR1 is non-cytotoxic and non-proliferating to normal lymphocytes, as well as tumor cell lines even at 1000 µg/ml. RR1 activated different subsets of lymphocytes, such as NK cells (331%), T cells (102%) and B cells (39%) at a concentration of 100 µg/ml. The significant activation of NK cells leads to the dose-dependent killing of tumor cells by activated normal lymphocytes in a functional assay. Immune activation by RR1 in normal lymphocytes elicited the synthesis of IL-1β (1080 pg/ml), IL-6 (21833 pg/ml), IL-12 p70 (50.19 pg/ml), IL-12 p40 (918.23 pg/ml), IL-18 (27.47 pg/ml), IFN-γ (90.16 pg/ml), TNF-α (2225 pg/ml) and MCP-1 (2307 pg/ml) at 100 pg/ml concentration, while it did not induce the production of IL-2, IL-4, IL-10, IFN-α and TNF-β. This cytokine profile demonstrates the Th1 pathway of T helper cell differentiation essential for cell-mediated immunity, with a self regulatory mechanism for the control of its overproduction.

RR1 also activated the complement components in the alternate pathway, as demonstrated by a stepwise increase in C3a des Arg components. Incidentally, RR1 stimulation did not produce any oxidative stress in the lymphocytes and caused only a slight increase in nitric oxide production justified by the insignificant induction of iNOS. The fact that RR1 is soluble in water, has high molecular mass, activates lymphocytes (particularly NK cells), activates complement, induces a Th1 pathway-associated cytokine profile, together with a low level of nitric oxide synthesis, and the absence of oxidative stress, confer potential biodefense properties to this novel α-D-glucan.

The signaling mechanism of RR1 was investigated in macrophages to gain further understanding of its immunostimulating properties. When RAW264.7 macrophages were incubated with RR1 at 4° C., RR1 inhibited the nonopsonic binding and phagocytosis of zymosan-A bioparticles in a dose-dependent manner. However, it had very little effect on the opsonic binding and internalization of zymosan A bioparticles. Incubation of macrophages with anti-CD11b mAb followed by RR1 failed to show any inhibitory effect on RR1-induced TNF-α synthesis which confirmed the non-involvement of CR3 on the opsonic binding and internalization of RR1 in macrophages unlike zymosan. The anti-CD11b mAb has significant inhibitory effect on the zymosan A-induced TNF-α synthesis. RR1 induced TNF-α synthesis in macrophages in a dose-dependent manner which can be completely inhibited by the NF-κB inhibitor caffeic acid phenethyl ester (CAPE). RR1 activated NF-κB in a time- and dose-dependent manner and this modulation of nuclear NF-κB activity is associated with the degradation of I-κBα thus facilitating the translocation of NF-κB into the nucleus. RR1-induced NF-κB activity peaks at 8 hours of RR1 stimulation while I-κB-α degradation occurred within 1 hour of stimulation. RR1-induced NF-κB activation occurred through TLR6 signaling because RR1 induced IL-8 synthesis in TLR6-transfected HEK293 cells and not in other transfectants. These results show that RR1 activates the immune system through the activation of macrophages that occurs through TLR6 signaling, NF-κB translocation and production of immune proteins. A schematic of the signal transduction pathway of immune-stimulation by RR1 in monocytes/macrophages is depicted in FIG. 20.

Preferably, the immune response stimulated by the RR1 compound according to the invention is biased toward the Th1-type phenotype and away from the Th2-type phenotype. With reference to the invention, stimulating a Th1-type immune response can be determined in vitro or ex vivo by measuring cytokine production from cells treated with an RR1 compound as compared to those treated without an RR1 compound. Methods to determine the cytokine production of cells include, but are not limited to, those methods described herein, as well as other methods known in the art. The cytokines produced in response to RR1 treatment indicate a Th1-type or a Th2-type biased immune response by the cells.

As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFN-gamma. In contrast, "Th2-type biased cytokines" refers to those associated with a Th$_2$-type immune response, and include, but are not limited to, IL-4, IL-5, IL-10 and IL-13. Cells useful for the determination of RR1 activity include cells of the immune system, primary cells isolated from a subject and/or cell lines, preferably APCs and lymphocytes, even more preferably macrophages and T cells.

Stimulating a Th1-type immune response can also be measured in a subject treated with an RR1 compound and can be determined by any method known in the art including, but not limited to: (1) a reduction in levels of IL-4 measured before and after antigen-challenge; or detection of lower (or even absent) levels of IL-4 in an RR1-treated subject as compared to an antigen-primed, or primed and challenged, control treated without RR1; (2) an increase in levels of IL-12, IL-18 and/or IFN (alpha, beta, or gamma) before and after antigen challenge; or detection of higher levels of IL-12, IL-18 and/or IFN (alpha, beta, or gamma) in an RR1-treated subject as compared to an antigen-primed or, primed and challenged, control treated without RR1; (3) IgG2a antibody production in an RR1-treated subject as compared to a control treated without RR1; and/or (4) a reduction in levels of antigen-specific IgE as measured before and after antigen challenge; or detection of lower (or even absent) levels of antigen-specific IgE in an RR1-treated subject as compared to an antigen-primed, or primed and challenged, control treated without RR1. A variety of these determinations can be made by measuring cytokines made by APCs and/or lymphocytes, preferably macrophages and/or T cells, in vitro or ex vivo using methods described herein or any known in the art. Methods to determine antibody production include any known in the art.

The Th1-biased cytokine induction which occurs as a result of RR1 administration produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

The RR1 compounds of the subject invention are useful for treating pathological conditions in humans or non-human animals requiring immunostimulation, such as conditions involving immunosuppression. Examples of conditions for which immunostimulation is desired include, but are not limited to, treatment or prevention of osteomyelitis, chronic bronchitis, tuberculosis, lower respiratory tract infections, tonsillitis, otitis media, hepatitis, AIDS, diabetes mellitus, diabetic ulcers, and pediatric diseases. The RR1 compounds of the subject invention are also useful as standards to assess the activity of other putative immunostimulatory agents.

By virtue of RR1's immunostimulatory properties, the therapeutic methods, compounds, and compositions of the present invention can be used to treat a number of cell proliferation disorders, such as cancers, including, but not limited to, leukemias and lymphomas, such as acute lymphocytic leukemia, acute non-lymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms' Tumor, bone tumors, and soft-tissue sarcomas, common solid tumors of adults such as lung cancer, colon and rectum cancer, breast cancer, prostate cancer, urinary cancers, uterine cancers, bladder cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The methods of the subject invention can be carried out in vivo or in vitro, to inhibit the growth of cancerous cells in humans and non-human mammals.

Some specific actions attributed to β-glucans may also be relevant to RR-1. This involves the inhibition of NF-kappaB activation induced by lipopolysaccharide (LPS) or other endotoxins/exotoxins. NF-kappaB activation and other pathways play an important role in the development of sepsis and septic shock. The (1→3)-beta-D-glucan has demonstrated decreased activation of NF-kappaB and increased long term survival in mice with sepsis (Williams, D. L. et al. *Shock*, 2000, 13:446-452; Williams, D. L. et al. *Surgery*, 1999, 126: 54-65). Accordingly, the present invention includes a method of treating sepsis or septic shock in a human or non-human mammal by administering at least one RR1 compound. In another aspect, the present invention includes a method for reducing NF-kappaB activation induced by LPS or other endotoxin and/or exotoxin in a human or non-human mammal, by administering at least one RR1 compound of the invention.

By virtue of its action as a biological response modifier, RR1 compounds of the invention may also be administered to subjects for the treatment of other disorders such as acute and chronic pulmonary diseases or any other disorder that may be associated with an abnormality of the innate or adaptive immune systems. The present invention includes methods for treating such disorders. There is evidence to support a role for cancer chemoprevention by plant polysaccharides in addition to an anti-tumor effect (Kim, H. S. et al. *Carcinogenesis*, 1999, 20:1637-1640. The present invention includes methods for cancer chemoprevention, wherein at least one RR1 compound of the invention is administered to a subject.

The therapeutic methods of the present invention can be advantageously combined with at least one additional therapeutic method or therapy known to those of skill in the art for the treatment or management of cell proliferation disorders (e.g., cancer) or other pathological conditions (e.g., diseases or other disorders) that may be treated or managed with immunostimulation or immunosuppression. Examples of such adjunctive therapies include, but are not limited to, chemotherapy, radiation therapy, and administration of anti-cancer drugs or other anti-cancer agents. The adjunctive therapy may be allopathic or non-allopathic, such as acupuncture, massage therapy, energy therapies, etc. The pathological condition may be an acute or chronic disease or disorder.

While RR1 and RR1 analogs can be administered as isolated compounds, it is preferred to administer these compounds as a pharmaceutical composition. The subject invention thus further provides pharmaceutical compositions comprising RR1, or an analog thereof, as an active agent, or physiologically acceptable salt(s) thereof, in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The RR1 compounds of the subject invention can be formulated according to known methods for preparing pharmaceutically useful compositions. Formulations are described in a number of sources which are well known and readily available to those skilled in the art. For example, *Remington's Pharmaceutical Science* (Martin E W, Easton Pa., Mack Publishing Company, $19^{th}$ ed., 1995) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

The RR1 compounds of the present invention include all hydrates and salts of RR1 that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of RR1 may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As used herein, the term "analogs" refers to compounds that are substantially the same as RR1 (as shown in FIG. 3) but which may have been modified by, for example, adding side groups, oxidation or reduction of the parent structure, so long as the parent compound's a conformation and (1→4) and (1→6) glucopyranosyl linkages remain intact, and one or more of the parent compound's immunostimulatory properties is substantially retained. Analogs of the exemplified compounds can be readily prepared using commonly known standard reactions. These standard reactions include, but are not limited to, hydrogenation, alkylation, acetylation, and acidification reactions.

Therapeutic application of the RR1 compounds and compositions containing them can be accomplished by any suitable therapeutic method and technique presently or prospectively known to those skilled in the art. Further, the RR1 compounds of the invention are useful as starting materials or intermediates for the preparation of other useful compounds and compositions.

RR1 compounds of the invention and immune-modulating compositions containing such compounds may be systemically administered (e.g., orally or intravenously) in combination with a pharmaceutically acceptable carrier such as an inert diluent or an assimilable edible carrier. The RR1 compound may be enclosed in hard or soft shell gelatin capsules, may be compressed into tablets, or may be incorporated directly with the food of the patient's diet. For oral therapeutic administration, the RR1 compound may be combined with one or more excipients and used in the form of ingestible tablets, buccal tablets, troches, capsules, elixirs, suspensions, syrups, wafers, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the RR1 compound of the present invention may be incorporated into sustained-release preparations and devices.

The active agent, an RR1 compound of the present invention (i.e., RR1, or pharmaceutically acceptable salts or analogs of RR1), may also be administered intravenously or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the RR1 compound (i.e., RR1, or a pharmaceutically acceptable salt or analog of RR1) in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the RR1 compounds may be applied in pure-form, i.e., when they are liquids. However, it will generally be desirable to administer them to the skin as compositions, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the RR1 compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the RR1 compound to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Accordingly, the present invention includes a pharmaceutical composition comprising an RR1 compound (i.e., RR1, or pharmaceutically acceptable salt or analog thereof) in combination with a pharmaceutically acceptable carrier, which is immunomodulatory. Immunomodulatory compositions adapted for oral, topical or parenteral administration, comprising an amount of RR1 compound constitute a preferred embodiment of the invention. The dose administered to a patient, particularly a human, in the context of the present invention should be sufficient to achieve a therapeutic response in the patient over a reasonable time frame. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

In the context of cancer, a suitable dose is that which will result in a concentration of the active agent (an RR1 compound of the invention) in tumor tissue which is known to achieve the desired response. The preferred dosage is the amount which results in maximum inhibition of cancer cell growth, without unmanageable side effects. Administration of an RR1 compound, and compositions containing such compounds, can be continuous or at distinct intervals, as can be determined by a person of ordinary skill in the art.

To provide for the administration of such dosages for the desired therapeutic treatment, pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Mammalian species which benefit from the disclosed methods, compounds, and compositions, include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such species.

Patients in need of treatment using the methods of the present invention can be identified using standard techniques known to those in the medical profession.

As used herein, the terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); pancreatic cancer; retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

According to the method of the subject invention, RR1, or a pharmaceutically acceptable salt or analog thereof, can be administered to a patient by itself, or co-administered with another agent. Co-administration can be carried out simultaneously (in the same or separate formulations) or consecutively. Furthermore, according to the method of the subject invention, RR1, or a pharmaceutically acceptable salt or analog thereof, can be administered to a patient as adjunctive therapy. For example, RR1, or a pharmaceutically acceptable salt or analog thereof, can be administered to a patient in conjunction with chemotherapy.

Thus, the RR1 compounds of the subject invention (RR1, or a pharmaceutically acceptable salt or analog thereof), whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, other immunostimulatory agents, anticoagulants, buffering agents, anti-inflammatory agents, anti-pyretics, time-release binders, anesthetics, steroids, and corticosteroids. Such components can provide additional therapeutic benefit, act to affect the therapeutic action of the RR1 compound, or act towards preventing any potential side effects which may be posed as a result of administration of the RR1 compound. The RR1 compounds of the subject invention can be conjugated to a therapeutic agent, as well.

Additional agents that can be co-administered to a patient, consecutively, or simultaneously, in the same formulation or as a separate formulation, include those that modify a given biological response, such as immunomodulators. For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered. Anti-cancer agents, cytotoxic agents, and/or chemotherapeutic agents may be co-administered to a patient with an RR1 compound of the present invention, consecutively or simultaneously, in the same formulation or as a separate formulation. In one embodiment, the RR1 compound of the invention is co-administered with an antigen. Preferably, the antigen is an active ingredient within a vaccine.

In one embodiment, the invention provides compositions comprising an RR1 compound as the only immunologically active substance. Upon administration, the RR1 compound induces a stimulation of the immune system.

In other embodiments, as indicated above, the RR1 compound can be administered in conjunction with one or more other immunomodulatory molecules, such as antigens (including, but not limited to, proteins, glycoproteins, polysaccharides, and lipids), and/or immunomodulatory facilitators such as co-stimulatory molecules (including, but not limited to, cytokines, chemokines, targeting protein ligand, trans-activating factors, peptides, and peptides comprising a modified amino acid) and adjuvants (including, but not limited to, alum, lipid emulsions, and polylactide/polyglycolide microparticles). The term "immunomodulatory", as used herein, includes immunostimulatory as well as immunosuppressive effects. Immunostimulatory effects include, but are not limited to, those that directly or indirectly enhance cellular or humoral immune responses. Examples of immunostimulatory effects include, but are not limited to, increased antigen-specific antibody production; activation or proliferation of a lymphocyte population such as NK cells, $CD4^+$ T lymphocytes, $CD8^+$ T lymphocytes, macrophages, and the like; increased synthesis of immunostimulatory cytokines including, but not limited to, IL-1, IL-2, IL-4, IL-5, IL-6, IL-12, IFN-gamma, TNF-alpha, and the like. Immunosuppressive effects include those that directly or indirectly decrease cellular or humoral immune responses. Examples of immunosuppressive effects include, but are not limited to, a reduction in antigen-specific antibody production such as reduced IgE production; activation of lymphocyte or other cell populations that have immunosuppressive activities such as those that result in immune tolerance; and increased synthesis of cytokines that have suppressive effects toward certain cellular functions. One example of this is IFN-gamma, which appears to block IL-4 induced class switch to IgE and IgG1, thereby reducing the levels of these antibody subclasses.

The RR1 compound and the antigen and/or immunomodulatory facilitator can be administered together in the form of a conjugate or co-administered in an admixture sufficiently close in time so as to modulate an immune response. Preferably, the RR1 compound and immunomodulatory molecule are administered simultaneously. The term "co-administration" as used in this context refers to the administration of at least two different substances sufficiently close in time to modulate an immune response. Preferably, co-administration refers to simultaneous administration of at least two different substances.

As used herein, the term "conjugate" refers to a complex in which an RR1 compound and an immunomodulatory molecule are linked. Such conjugate linkages include covalent and/or non-covalent linkages.

As used herein, the term "antigen" means a substance that is recognized and bound specifically by an antibody or by a T cell antigen receptor. Antigens can include peptides, proteins, glycoproteins, polysaccharides, gangliosides and lipids; portions thereof and combinations thereof. The antigens can be those found in nature or can be synthetic. Haptens are included within the scope of "antigen". A hapten is a low molecular weight compound that is not immunogenic by itself but is rendered immunogenic when conjugated with an immunogenic molecule containing antigenic determinants.

As used herein, the term "adjuvant" refers to a substance which, when added to an immunogenic agent, nonspecifically enhances or potentiates an immune response to the agent in the recipient host upon exposure to the mixture.

In another embodiment, the invention provides compositions comprising an RR1 compound and an antigen. Antigens suitable for administration with RR1 compounds include any molecule capable of eliciting a B cell or T cell antigen-specific response. Preferably, antigens elicit an antibody response specific for the antigen. A wide variety of molecules are antigens. These include, but are not limited to, sugars, lipids and polypeptides, as well as macromolecules such as complex carbohydrates, and phospholipids. Small molecules may need to be haptenized in order to be rendered antigenic. Preferably, antigens of the present invention include peptides, lipids (e.g., sterols, fatty acids, and phospholipids), polysaccharides such as those used in *Hemophilus influenza* vaccines, gangliosides and glycoproteins.

As used herein, the term "peptide" includes peptides and proteins that are of sufficient length and composition to achieve a biological response, e.g. antibody production or cytokine activity whether or not the peptide is a hapten. Typically, the peptides are of at least six amino acid residues in length. The term "peptide" further includes modified amino acids, such modifications including, but not limited to, phosphorylation, glycosylation, pegylation, lipidization and methylation.

In one embodiment, the invention provides compositions comprising an RR1 compound and an antigenic peptide. Antigenic peptides can include purified native peptides, synthetic peptides, recombinant proteins, crude protein extracts, attenuated or inactivated viruses, cells, micro-organisms, or fragments of such peptides.

Many antigenic peptides and proteins are known, and available in the art; others can be identified using conventional techniques. Protein antigens that can serve as immunomodulatory facilitators include, but are not limited to, the following examples. Isolated native or recombinant antigens can be derived from plant pollens (see, for example, Rafnar et al. (1991) *J. Biol. Chem.* 266:1229-1236; Breiteneder et al. (1989) *EMBO J.* 8:1935-1938; Elsayed et al. (1991) *Scand. J. Clin. Lab. Invest. Suppl.* 204:17-31; and Malley (1989) *J. Reprod. Immunol.* 16:173-186), dust mite proteins (see, for example, Chua et al. (1988) *J. Exp. Med.* 167:175-182; Chua et al. (1990) *Int. Arch. Allergy Appl. Immunol.* 91:124-129; and Joost van Neerven et al. (1993) *J. Immunol.* 151:2326-2335), animal dander (see, for example, Rogers et al. (1993) *Mol. Immunol.* 30:559-568), animal saliva, bee venom, and fungal spores. Live, attenuated and inactivated microorganisms such as HIV-1, HIV-2, herpes simplex virus, hepatitis A virus (Bradley et al. (1984) *J. Med. Virol.* 14:373-386), rotavirus, polio virus (Jiang et al. (1986) *J. Biol. Stand.* 14:103-109), hepatitis B virus, measles virus (James et al. (1995) *N. Engl. J. Med.* 332:1262-1266), human and bovine papilloma virus, and slow brain viruses can provide peptide antigens. For immunization against tumor formation, immunomodulatory peptides can include tumor cells (live or irradiated), tumor cell extracts, or protein subunits of tumor antigens. Vaccines for immuno-based contraception can be formed by including sperm proteins administered with an RR1 compound (Lea et al. (1996) *Biochim. Biophys. Acta* 1307:263).

The antigens to be used in the compositions and methods of the invention are not critical. Mixtures of different antigens may be used according to the present invention. Preferably, proteins or peptides derived from a viral or a bacterial pathogen, or from fungi or parasites, are used as such antigens (including derivatized antigens or glycosylated or lipidated antigens or polysaccharides or lipids). Another preferred source of antigens are tumor antigens. Preferred pathogens are selected from human immunodeficiency virus (HIV), hepatitis A and B viruses, hepatitis C virus (HCV), rous sarcoma virus (RSV), Epstein Barr virus (EBV) Influenza virus, Rotavirus, *Staphylococcus aureus, Chlamydia pneumonias, Chlamydia trachomatis, Mycobacterium tuberculosis, Streptococcus pneumonias, Bacillus anthracis, Vibrio*

*cholerae, Plasmodium* sp. (*Pl. falciparum, Pl. vivax*, etc.), *Aspergillus* sp. or *Candida albicans*. Antigens may also be molecules expressed by cancer cells (e.g., tumor antigens). The derivation process may include the purification of a specific protein from the pathogen/cancer cells, the inactivation of the pathogen as well as the proteolytic or chemical derivatization or stabilization of such a protein. In the same way, tumor antigens (cancer vaccines) or autoimmune antigens may be used in the compositions and methods according to the present invention. Thus, a tumor vaccination or a treatment for autoimmune diseases may be performed.

The RR1 compound and antigen can be administered as RR1-antigen conjugate and/or they can be co-administered as a complex in the form of an admixture, such as in an emulsion. The association of the RR1 compound and the antigen molecules in an RR1-antigen conjugate can be through covalent interactions and/or through non-covalent interactions, including high affinity and/or low affinity interactions. Examples of non-covalent interactions that can couple RR1 compound and an antigen in an RR1-antigen conjugate include, but are not limited to, ionic bonds, hydrophobic interactions, hydrogen bonds and van der Waals attractions.

In another embodiment, an RR1 compound can be administered in conjunction with one or more immunomodulatory facilitators. Thus, the invention provides compositions comprising an RR1 compound and an immunomodulatory facilitator. As used herein, the term "immunomodulatory facilitator" refers to molecules which support and/or enhance the immunomodulatory activity of an RR1 compound. Examples of immunomodulatory facilitators can include co-stimulatory molecules, such as cytokines, and/or adjuvants. The RR1 compound and facilitator can be administered as an RR1-facilitator conjugate and/or they can be co-administered as a complex in the form of an admixture, such as in an emulsion. The RR1 compound and the facilitator molecules in an RR1-facilitator conjugate can be associated through covalent interactions and/or through non-covalent interactions, including high affinity and/or low affinity interactions. Examples of non-covalent interactions that can couple an RR1 compound and a facilitator in an RR1-facilitator conjugate include, but are not limited to, ionic bonds, hydrophobic interactions, hydrogen bonds and van der Waals attractions.

Immunomodulatory facilitators include, but are not limited to, co-stimulatory molecules (such as cytokines, chemokines, targeting protein ligand, trans-activating factors, peptides, and peptides comprising a modified amino acid) and adjuvants (such as alum, lipid emulsions, and polylactide/polyglycolide microparticles).

Among suitable immunomodulatory cytokine peptides for administration with RR1 compounds are the interleukins (e.g., IL-1, IL-2, IL-3, etc.), interferons (e.g., IFN-alpha, IFN-beta, IFN-gamma), erythropoietin, colony stimulating factors (e.g., G-CSF, M-CSF, GM-CSF) and TNF-alpha. Preferably, immunostimulatory peptides for use in conjunction with RR1 compounds are those that stimulate Th1-type immune responses, such as IL-12 (Bliss et al. (1996) *J. Immunol.* 156:887-894), IL-18, TNF-alpha, beta, and gamma, and/or transforming growth factor (TGF)-alpha.

Peptides administered with RR1 compounds can also include amino acid sequences that mediate protein binding to a specific receptor or that mediate targeting to a specific cell type or tissue. Examples include, but are not limited to, antibodies or antibody fragments, peptide hormones such as human growth hormone, and enzymes. Immunomodulatory peptides also include peptide hormones, peptide neurotransmitters and peptide growth factors. Co-stimulatory molecules such as B7 (CD80), trans-activating proteins such as transcription factors, chemokines such as macrophage chemotactic protein (MCP) and other chemoattractant or chemotactic peptides are also useful peptides for administration with an RR1 compound of the invention.

The RR1 compound can also be conjugated to other antigens such as lipids, polysaccharides, gangliosides and the like, through a linking group such as a peptide.

The invention also provides for the administration of an RR1 compound in conjunction with an adjuvant. Administration of an antigen with an RR1 compound and an adjuvant leads to a potentiation of a immune response to the antigen and thus, can result in an enhanced immune response compared to that which results from a composition comprising the RR1 compound and antigen alone. Thus, in another embodiment, the invention provides compositions comprising an RR1 compound, an antigen, and an adjuvant whereby the RR1 compound/antigen/adjuvant are co-administered. Preferably, the immunogenic composition contains an amount of an adjuvant sufficient to potentiate the immune response to the immunogen. Preferably, adjuvants include, but are not limited to, oil-in-water emulsions, water-in-oil emulsions, alum (aluminum salts), liposomes and microparticles, including but not limited to, polysytrene, starch, polyphosphazene and polylactide/polyglycosides. More preferably, the RR1 compound and antigen are co-administered with alum. More preferably, the RR1 compound and antigen are co-administered with liposomes. Still more preferably, the RR1 compound and antigen are co-administered with an oil-in-water emulsion.

Suitable adjuvants also include, but are not limited to, squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873-875, as well as, lipid-based adjuvants and others described herein. For veterinary use and for production of antibodies in animals, mitogenic components of Freund's adjuvant (both complete and incomplete) can be used.

As with all immunogenic compositions, the immunologically effective amounts of the components can be determined empirically. Factors to be considered include the antigenicity, whether or not RR1 compound and/or antigen will be complexed with or covalently attached to an immunomodulatory facilitator, an adjuvant or carrier protein or other carrier, route of administration and the number of immunizing doses to be administered. Such factors are known in the vaccine art and it is well within the skill of immunologists to make such determinations without undue experimentation.

The invention further provides for compositions in which an RR1 compound and an immunomodulatory molecule(s) are in proximate association at a distance effective to enhance the immune response generated compared to the administration of the RR1 compound and the immunomodulatory molecule as an admixture. Thus, the invention provides compositions and methods of use thereof comprising an encapsulating agent that can maintain the proximate association of the RR1 compound and immunomodulatory molecule until the complex is available to the target. Preferably, the composition comprising the RR1 compound, immunomodulatory molecule, and encapsulating agent is in the form of adjuvant oil-in-water emulsions, microparticles and/or liposomes. More preferably, adjuvant oil-in-water emulsions, microparticles and/or liposomes encapsulating an RR1-immunomodulatory molecule are in the form of particles from about 0.04 µm to about 100 µm in size, more preferably, from about 0.1 µm to about 20 µm, even more preferably, from about 0.15 µm to about 10 µm.

Colloidal dispersion systems, such as microspheres, beads, macromolecular complexes, nanocapsules and lipid-based system, such as oil-in-water emulsions, micelles, mixed micelles and liposomes can provide effective encapsulation of RR1 compound-containing compositions.

A further aspect of the subject invention provides a process for obtaining RR1 from *Tinospora cordifolia* plant material. According to a preferred embodiment, RR1 is isolated from the aerial parts (stem and leaves) of the plant material. 500 g of the dried and powdered plant material is extracted in a sox let extractor for 72 hours with pure methanol. The residue is taken in hot distilled water, centrifuged and collected from the supernatant. It is centrifuged again and the crude polysaccharide is precipitated with 80% alcohol from the supernatant. The precipitate is filtered, washed with alcohol, dissolved in distilled water, and the clear solution is treated with 15% trichloroacetic acid. The solution is centrifuged to remove any residue and the clear supernatant is reprecipitated with acetone. The precipitate is filtered, washed several times with acetone and redissolved in distilled water. The clear solution is dialyzed (membrane MWCO 60000 Da) in running water for 72 hours and lyophilized in tubes in a speedvac. An exemplified embodiment of the process is shown in the flow chart of FIG. 1. A scientist skilled in the art of natural products purification can easily adapt the methods described and substitute a variety of solvents and stationary phases for those described in the preferred embodiment of the invention. The aqueous fraction of *Tinospora cordifolia* extract can be separated by draining, filtering, decanting, or by any other method known in the art to separate aqueous parts of solutions or mixtures. In addition to chromatography, methods such as crystallization and partitioning can also be used to purify the desired compounds. Various alternative reagents may be utilized for isolation of the RR1 compound. For example, monohydric alcohols may be used instead of ethanol. Acetone can be substituted with ethanol in the isolated procedure. See, for example, Brown G. G., Unit Operations, John Wiley & Sons, 1956; McCabe, W. L. and J. C. Smith, Unit Operations of Chemical Engineering, McGraw-hill, 1956; and Perry, R. H., and D. Green, Perry's Chemical Engineers' Handbook, $7^{th}$ Edition, McGraw-Hill, 1997, which are incorporated herein by reference in their entirety.

Optionally, once obtained, the isolated RR1 compound can be used as a starting material to synthesize an RR1 analog of the subject invention. Optionally, the process can further include the step of evaluating the isolated RR1 compound or analog for immunomodulatory activity using in vitro or in vivo assays, such as those described herein.

There is no particular limitation as to the method for extracting RR1 from the plant. For example, extraction with various solvents or supercritical fluid extraction is applicable. There is no particular limitation as to the solvents used for extraction of RR1 from the plant. Examples of suitable solvents include aqueous media such as water, inorganic salt aqueous solution and buffer solutions, and organic solvents such as alcohol, hexane, toluene, petroleum ether, benzene, ethyl acetate, chloroform, dichloromethane, 1,1,2-trichloroethane, di-methylsulfoxide, and acetone, among which alcohol is preferred. Water can be undistilled water, distilled water, deionized water, or pure water. Examples of buffer solution that may be used include phosphate buffer and citrate buffer.

In extracting RR1 from the plant material, it is appropriate to use a solvent which is suitable for therapeutics, such as water, water-containing ethanol, or anhydrous ethanol. Examples of the alcohol that may be used include monohydric alcohols such as methanol, ethanol, propanol and butanol, and multi-hydric alcohols such as propylene glycol and glycerol, among which a monohydric alcohol is preferred, and particularly ethanol is preferred. These solvents may be used alone or as a mixture. As the mixed solvent, water-containing alcohols are preferred. Water-containing monovalent alcohols are more preferred, and water-containing ethanol is particularly preferred.

For extraction, the solvent may be used, for example, in an amount of 0.1 to 10,000 parts by weight preferably 1 to 100 parts by weight based on 1 part by weight of the plant. There is no particular limitation as to the extraction temperature, but the extraction is preferably carried out at 0 to 100° C., more preferably at 20 to 90° C. There is no particular limitation as to the time for extraction, but it may preferably be conducted, for example, for a period of 1 minute to 1 week, more preferably 30 minutes to 1 day.

There is no particular limitation as to the apparatus used for extraction, and a vessel designed for efficient extraction, a stirrer, a reflux condenser, a Soxhlet extractor, a homogenizer, a shaker, a supersonic generator, etc., may be used. The liquid extract may be treated by means of various solid-liquid separation such as sedimentation, cake filtration, clear filtration, centrifugal filtration, centrifugal sedimentation, compression separation or filter press.

For preparing the plant powder, all or parts of the plant containing RR1 may be used, such as leaves, branches, stems, stem bark, roots, seeds, cultured cells or organs, or callus. The aerial parts (stem and leaves) are preferred. The plant material may be used as such or after being treated physically or chemically or biologically. Examples of the method of physical or chemical treatment are drying, freeze-drying, disruption, and extraction. The physically or chemically treated matter includes dried matter, freeze-dried matter, disrupted matter and extracted matter. The extracted matter includes the residue of the plant obtained after the extraction.

For preparing the plant powder, the preferably dried *Tinospora cordifolia* plant material can be crushed with a compression crusher, such as jaw crusher, gyratory crusher or cone crusher; shearing machine, such as cutter mill or shredder; impact crusher, such as hammer crusher; roll mill, such as roll crusher; rotary mill, such as disintegrator or cage mill; screw mill, such as coffee mill; rolling mill, such as edge runner; hammering mill, such as stamp mill; roller mill, such as centrifugal roller mill, ball bearing mill, bowl mill, or zego mill; high speed rotary mill, such as swing hammer mill, pin mill, cage mill, turbo-type mill, or centrifugal mill; vessel vibrating mill, such as rolling ball mill, vibrating ball mill, planetary ball mill, or CF mill; jet mill, such as flow-pipe type mill, stirring tank mill, annular-type mill, air suction type mill, impact plate impact miller, or fluidized bed mill; crusher, such as ultrasonic shredder; stone mortar or mortar. The product obtained by the aforementioned method may further be processed physically or chemically to give plant powder.

The plant powder can be coarse or fine. The average particle size of the plant powder is preferably 0.1 μm to 1 mm, more preferably 1 to 100 μm, and particularly 2 to 50 μm in a dry state. The average particle size of the plant powder in a dry state can be determined, for example, by a laser diffraction particle distribution analyzer. Alternatively, when the plant powder is swelled with a 1:1 mixture of glycerol and water, the average particle size of the powder is preferably 1 μm to 10 mm, more preferably 10 μm to 1 mm, and particularly 20 to 500 μm. The average particle size of the plant powder in a swelling state can be determined, for example by observation with a microscope.

Methods of drying are known in the art. For example, the method of drying can involve drying under heating and reduced pressure, drying under heating and atmospheric pressure, or drying with a spray drier or with drum drier, or freeze-drying, among which drying under heating and reduced pressure or freeze-drying is preferred.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. As used herein, the term "tumor" is inclusive of non-solid neoplasms, such as leukemia. Molecular and phenotypic analysis of cancer cells within a tissue will usually confirm if the cancer is endogenous to the tissue or if the lesion is due to metastasis from another site.

As used herein, the terms "treat" or "treatment" refer to both therapeutic treatment and prophylactic or preventative measures, wherein the object is to prevent or slow down (lessen) an undesired physiological change or disorder, such as the development or spread of a cell proliferation disorder, such as cancer, or other pathological conditions (e.g., diseases or other disorders). Preferably, the pathological condition is one that may be treated or managed with either immunostimulation or immunosuppression. For purposes of this invention, beneficial or desired clinical results include, but are not limited to, alleviation of symptoms, diminishment of extent of disease, stabilized (i.e., not worsening) state of disease; delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "(therapeutically) effective amount" refers to an amount of an agent, such as an RR1 compound of the invention or other agent, effective to treat a pathological condition (e.g., a disease or other disorder), such as a cell proliferation disorder, in a mammal. In the case of cancer, the therapeutically effective amount of the agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the agent may prevent growth and/or kill existing cancer cells, it may be cytostatic and/or cytotoxic. For cancer therapy, efficacy can, for example, be measured by assessing the time to disease progression (TTP) and/or determining the response rate (RR).

As used herein, the term "anti-cancer agent" refers to a substance or treatment that inhibits the function of cancer cells, inhibits their formation, and/or causes their destruction in vitro or in vivo. Examples include, but are not limited to, cytotoxic agents (e.g., 5-fluorouracil, TAXOL) and anti-signaling agents (e.g., the PI3K inhibitor LY).

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston), and anti-androgens such as flutamide, nilutamide, bicalutamide, leuprolide, and goserelin, etc.

As used herein, the term "RR1 compound" is intended to refer to RR1, as shown in FIG. 3, or a pharmaceutically acceptable salt or analog of RR1. As used herein, the term "isolated" with respect to RR1 or a RR1 compound refers to the compound substantially free from the medium in which it naturally occurs, e.g., from *Tinospora cordifolia* plant material or plant extract. However, an isolated RR1 compound may also be obtained by appropriate chemical synthesis reactions known to those skilled in the art (Greene, T. W. and Wuts, P. G. M. "Protective Groups in Organic Synthesis" John Wiley & Sons, Inc. New York. 3rd Ed. pg. 819, 1999; Honda, T. et al. *Bioorg. Med. Chem. Lett.*, 1997, 7:1623-1628; Honda, T. et al. *Bioorg. Med. Chem. Lett.*, 1998, 8:2711-2714; Konoike, T. et al. *J. Org. Chem.*, 1997, 62:960-966; Honda, T. et al. *J. Med. Chem.*, 2000, 43:4233-4246).

The terms "comprising", "consisting of" and "consisting essentially of" are defined according to their standard meaning. The terms may be substituted for one another throughout the instant application in order to attach the specific meaning associated with each term.

As used herein, the singular forms "a", "an", and "the" include plural reference unless the context clearly dictates otherwise. Thus, for example, a reference to "an RR1 compound" includes more than one such RR1 compound. A reference to "an immunomodulatory molecule" includes more than one such immunomodulatory molecule, or type of immunomodulatory molecule. A reference to "an antigen" is used to refer to more than one antigen, or type of antigen, and the like.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P.

Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Following are examples that illustrate materials, methods, and procedures for practicing the invention. The examples are illustrative and should not be construed as limiting.

Materials and Methods

Isolation and characterization of RR1. Preliminary investigations with extracts of the *Tinospora cordifolia* powder (commercially available from GARRY and SUN, Inc., Reno, Nev.) revealed that the immune stimulating principle is confined in the aqueous fraction. The procedure adapted for the isolation is illustrated in the flow chart shown in FIG. 1. The final RR1 compound, shown in FIG. 3, was isolated in about 0.1% yield of the total dry material used for extraction as a puffy solid that dissolved in water. The initial analysis of final product and the $^{13}$C NMR spectra revealed that it is a polysaccharide. Therefore, detailed polysaccharide analyses such as the glycosyl composition, linkage, molecular weight and conformation of the glucose units at the anomeric center were performed at the Complex Carbohydrate Research Center, University of Georgia, Athens. The glycosyl composition analysis was done by the combined Gas Chromatography/Mass Spectrometry (GC/MS) of the per-O-trimethylsilyl derivatives of the monosaccharide methyl glucosides obtained from RR1 by acidic methanolysis according to the method of York et al. (York, W. S. et al. *Methods Enzymol.*, 1985, 118:3-40). Inositol was used as an internal standard in this analysis. The monosaccharide derivatives were identified by their characteristic retention time and further authenticated with their mass spectra. To perform glycosyl linkage analysis, the sample was permethylated three times by the method of Cikanu and Kereck (Ciucanu, I. and F. Kereck *Carbohydr. Res.*, 1984, 131:209-217), hydrolyzed with 2 M trifluroacetic acid, reduced with NaBD$_4$ and acetylated with acetic anhydride/pyridine and the resulted partially methylated alditol acetates (PMAA) were analyzed by GC/MS. The sugar residues were identified by their characteristic retention times and mass spectral data. The conformations at the anomeric center of the glucopyranosyl units were obtained based on the 500 MHz protonNMR spectra recorded in D$_2$O and by comparison with the anomeric proton signals of standard samples. The molecular mass was obtained from the size exclusion chromatography using SUPELCO silica column (1.0×30 cm), eluting with 50 mM ammonium formate buffer at a rate of 0.5 m/min. and detected by the refractive index. Dextran samples were used as standards and the molecular mass was obtained by comparing the retention time of the eluted peak with the standards.

Immunostimulating Properties. To measure the immune stimulatory property of RR1, the activation of the different subsets of lymphocytes, syntheses of cytokines such as interleukin (IL)-1β, IL-2, IL-4, IL-6, IL-10, IL-12 p70 and p40, IL-18, interferon (IFN)-α and γ, Tumor Necrosis factor (TNF)-α and β, monocyte chemo-attractant protein (MCP)-1, synthesis of nitric oxide (NO), and the extent of oxidative stress elicited in human lymphocytes was analyzed. Normal lymphocytes were isolated by the histopaque density gradient method from fresh blood drawn from healthy volunteers and utilized for various assays. Human leukemic (CEM) and multidrug resistant (CEM/VLB) cell lines were grown in RPMI medium supplemented with 10% fetal bovine serum and antibiotics in 5% CO$_2$ incubator at 37° C.

Activation of Lymphocytes. Normal lymphocytes ($10^6$/ml) were treated with 0-100 μg of RR1 for 24 hours in a CO$_2$ incubator maintained at 37° C. in RPMI medium. The cells were then stained with specific fluorochrome-conjugated monoclonal antibodies for 30 minutes at room temperature and analyzed in a Coulter Elite Flow Cytometer by four and five color immunotyping assay protocol of Alamo and Melnick (Alamo, A. L. and S. J. Melnick *Cytometry*, 2000, 42:363-370) and the percentage of activation of subsets of lymphocytes such as NK, T and B cells were calculated.

Cytotoxicity of RR1 treated lymphocytes. To evaluate the enhanced cytotoxicity of activated lymphocytes, a functional assay was adopted using RR1-activated lymphocytes as effecter cells and human leukemic cells (CEM) as targets (Liu, L. et al. *Nat. Med.*, 2002, 8:185-189; Jerome, K. R. et al. *Nat. Med.*, 2003, 9:4-5). Briefly, normal lymphocytes ($10^6$/ml) were treated with different concentrations of RR1 in RPMI medium for 24 hours in a CO$_2$ incubator at 37° C. On the next day, target cells (CEM $1 \times 10^6$/ml) were labeled with 4.6 μM membrane labeling dye PKE26 (SIGMA) in 1 ml PBS at room temperature for 3 minutes. The labeling was stopped by adding an equal volume of fetal bovine serum (GIBCO, Life Sciences, MD) for one minute. The labeled tumor cells were then incubated with RR1 treated lymphocytes in an effecter to target ratio 1:1 for 4 hours and untreated lymphocytes were used as control. The percentage of cells killed by the activated NK cells was determined by fixing the mixture with 1 ml of 2% paraformaldehyde solution for 30 minutes on ice followed by suspending in 0.5% Tween 20 in PBS. The cell mixture was stained with 7.5 μl of anti-active caspase-3-FITC antibody (BD Biosciences, CA) for 30 minutes at room temperature, washed with PBS and analyzed in a Coulter Elite Flow Cytometer.

Quantification of Cytokine and Chemokine Synthesis. Cytokines such as IL-1β, IL-2, IL-4, IL-6, IL-10, IL-12p40, IL-12p70, IL-18, IFN-γ and TNF-α, β and chemokine, MCP-1 were quantified by ELISA procedure using kits from BD Biosciences, according to manufacturer's protocols. IFN-α was assayed using the ELISA kit of RESEARCH DIAGNOSTICS Inc. (New Jersey). In short, 50 μl of ELISA diluent is pipetted into antibody coated wells of 96 well plates followed by 100 μl of each standard and test samples, shaken for 5 seconds to mix the contents in the wells, covered with plate sealer and incubated for 2 hours at room temperature. After incubation, the contents of the wells were aspirated and washed five times with wash solution. After complete removal of the wash solution in the final wash, 100 μl of detection solution was added, covered with plate sealer, and incubated for 1 hour. The wells were washed 7 times with wash solution and added 100 μl of one step substrate reagent and incubated for 30 minutes in dark. The color development was stopped by adding 50 μl of stop solution and the absorbance were recorded at 450 nm with a reference wave length of 570 nm in a BIO-RAD Benchmark plate reader.

Complement activation pathway. Human complement C3a des Arg and C4a des Arg correlate-EIA Kits (ASSAY DESIGN Inc., Ann Arbor, Mich.) were used to measure the cleaved complement components (C3a des Arg and C4a des Arg) according to the manufacturer's protocols. In brief, 1 ml normal blood, drawn from healthy volunteer was incubated with 0-100 μg/ml of RR1 in a CO$_2$ incubator at 37° C. for 24 hours. The treated blood samples were centrifuged at 2000×g at 4° C. and 225 μl of complement reagent 'A' was added to an equal volume of the sample supernatant and vortexed thoroughly. To this mixture, 50 μl of 10 N HCl was added, vortexed again and incubated at room temperature for 1 hour. The samples were centrifuged at 10,000 rpm in a micro centrifuge at room temperature for 5 minutes, 180 μl of the supernatant was transferred to a 15 ml tube, 20 μl of 9 N NaOH was added and vortexed thoroughly. To this mixture 600 μl of complement reagent 'B' was added followed by 10.7 ml of assay buffer, vortexed and used for the analysis. Assay sample (100 μl) was pipetted into wells in a 96-well microplate followed by 50 μl of blue conjugate and 50 μl of yellow antibody. The plates were shaken on a platform shaker at 500 rpm for 2 hours. The wells were aspirated to remove the unbound materials, washed thrice with 200 μl of wash solution and added 200 μl of p-Npp substrate solution. The plate was incubated at 37° C. for 1 hour without shaking, added 50 μl of stop solution and absorbance was taken at 405 nm with a reference wavelength of 570 nm in a BIO-RAD Bench top plate reader.

Inducible Nitric Oxide Synthase (iNOS) induction and Nitric oxide (NO) synthesis. Higher and long lasting release of NO is caused by the enzyme iNOS upon stimulation with arginine on stimulation. The iNOS induction by RR1 stimulation was assayed by QUANTIKINE iNOS immunoassay kit (R&D systems, Minneapolis, Minn.) which employs a sandwich enzyme immunoassay technique. The iNOS was assayed from the cytoplasmic extract of the cells treated with different concentrations of RR1. The samples and standards were pipetted in to the wells of the 96-well plate and any iNOS present was bound to the immobilized antibody. After washing away the unbound substances, an enzyme linked monoclonal antibody specific for iNOS was added. After washing away the unbound antibody enzyme reagent, the color developing substrate solution was added, the color development was stopped by stop solution and the absorbance was read at 450 nm with a reference wave length of 570 nm in the Bio-Rad plate reader.

The NO quantification was assayed by Nitric Oxide quantification kit (ACTIVE MOTIF, Carlsbad, Calif.) as per the manufacturer's protocol. Briefly, lymphocytes ($10^6$/ml) were incubated with varying concentrations of RR1 (0-100 μg/ml) for 24 hours in a nitrate free medium (DULBECO Minimum Essential Medium) at 37° C. The cell culture supernatant (70 μl) was pipetted into the wells of a 96-well plate along with 20 μl reconstituted co-factor and 10 μl nitrate reductase enzyme solution. The plate was shaken at 150 rpm on a plate shaker for 30 minutes at room temperature. Griess reagents A and B (50 μl each) were added into each well, allowed the color to develop for 20 minutes and the absorbance was taken at 540 nm with a reference wavelength of 620 nm in the BIO-RAD plate reader.

Oxidative stress (GSH/GSSG levels). The measure of the reduced (GSH) as well as oxidized (GSSG) levels of glutathione and their ratio are useful indicators for oxidative stress. The levels of GSH and GSSG were assayed by a colorimetric method using Biotech GSH/GSSG-412 kit (Oxis Research, Portland, Oreg.) according to manufacturer's protocol. Briefly, normal blood samples from healthy donors were incubated with different concentrations of RR1 for 24 hours in a 5% $CO_2$ incubator at 37° C. For GSSG, 100 μl of each of the treated sample was frozen at −70° C. for 4 hours, thawed and added 290 μl of 5% meta phosphoric acid (MPA). The samples were vortexed for 15-20 seconds and centrifuged at 1000×g for 10 minutes. MPA extract (50 μl) was added to 700 μl of GSSG buffer that was used for the calorimetric assay. For GSH measurement 50 μl of the whole blood was frozen at −70° C., thawed and added 350 μl of 5% MPA, vortexed for 15-20 seconds and centrifuged at 10,000×g for 10 minutes. MPA extract (50 μl) was added to 3 ml of the assay buffer and used for further analysis. MPA buffer mixture (200 μl) of each standard and sample was transferred to a spectrophotometer cuvette, added 200 μl of chromogen followed by 200 μl of enzyme in the order and incubated at room temperature for 5 minutes. Afterwards, 200 μl of NADPH was added into the cuvette and changes in the absorbance at 412 nm were recorded in a BECKMAN spectrophotometer. The reaction rates were plotted using the absorbance values and the levels of GSH and GSSG were determined.

Statistical Analysis. Single factor ANOVA was used for data analysis.

Cell lines. Mouse monocyte (RAW 264.7), and human embryonic kidney (HEK293) cell lines were obtained from American Type Culture collection, Manassas, Va. for the investigation. HEK293 cells transfected with TLR2, TLR2/6 and TLR4/CD14/MD2 genes were purchased from INVIVOGEN Corporation, San Diego, Calif. The cells were grown in DMEM medium supplemented with 10% fetal bovine serum, L-glutamine (2 mM) and antibiotics (100 units/ml penicillin and 100 μg/ml streptomycin) in tissue culture flasks in a 5% $CO_2$ incubator. RR1 was isolated from *Tinospora cordifolia* powder purchased from GARRY and SUNS (Reno, Nev., USA) according to the extraction procedure described in Nair, P. K. et al. (Nair, P. K. et al. *Int. Immunopharmacol.*, 2004, 4:1645-1659). The endotoxin content of the sample was tested by Lymulus Amoebocyte Lysate Assay (Cambrex, Mass.), which showed insignificant levels (0.0008 ng/ml). Necessary precautions were taken to avoid endotoxin contamination through out the investigation, by using endotoxin free buffers, reagents and sterile water.

Reagents. Zymosan A and FITC-labeled Zymosan A bioparticles were purchased from Molecular Probes, Inc., Eugene, Oreg. Laminarin and Caffeic acid phenethyl ester (CAPE) were from SIGMA Chemical Co., St. Louis, Mo. Antimouse CD11b monoclonal antibody (mAb) was purchased from BD BIOSCIENCES, San Jose, Calif. FITC-labeled TLR2 and PE-labeled TLR4 antibodies were obtained from eBioscience, San Diego, Calif.

Nonopsonized binding of RR1. To determine the inhibitory effect of RR1 on non-opsonized binding of zymosan A bioparticles, mouse monocyte/macrophage cells ($0.5 \times 10^6$) were incubated with 0, 100, 500 and 1000 μg/ml of RR1 at 4° C. to prevent the local release of opsonins including complement (Ezekowitz, R. A. et al. *J. Clin. Invest.*, 1985, 76:2368-2376; Brown, G. D. et al. *J. Expt. Med.*, 2002, 196:407-412). After 1 hour incubation on ice, the cells were washed three times with pre-chilled culture medium, added FITC-conjugated zymosan A particles at a ratio of 25 particles/cell and kept on ice for another hour. The cells were washed with PBS twice and incubated in DMEM at 37° C. for 30 minutes in a $CO_2$ incubator. The unbound zymosan particles were removed by extensive washing with medium and the intracellular fluorescence of the zymosan-FITC analyzed in a Coulter Elite flow cytometer.

Opsonized binding and Phagocytosis. To determine the effect of RR1 and laminarin on opsonized binding and phagocytosis of zymosan A particles, RAW 264.7 cells were treated with RR1 or laminarin (0 and 500 μg/ml) in DMEM at 37° C. for 1 hour. This will ensure the release of opsonins and facilitate opsonic binding. The cells were washed with PBS twice and incubated with zymosan A-FITC bioparticles at a ratio of 25 particles/cell at 37° C. for 1 hour. The cells were suspended in PBS after removing the unbound zymosan particles by extensive washing with the medium, and the intracellular fluorescence analyzed in a Coulter Elite flow cytometer. The fluorescence intensity was expressed as percentage of control.

RR1-induced TNF-α synthesis. RAW 264.7 cells ($0.5 \times 10^6$/ml) were plated on 6-well plates with DMEM medium containing 0.5% FBS (starvation). Once the cells were attached, medium was replaced, RR1 was added at 0, 100, 500 and 1000 µg/ml doses and incubated at 37° C. for 24 hours. The medium was analyzed for the secreted TNF-α using the ELISA kit (BD BIOSCIENCES kit, San Jose, Calif.) based on the manufacturer's protocol.

To determine the effect of NF-κB inhibitor CAPE on TNF-α synthesis, RAW 264.7 cells were treated with 10 µg/ml of CAPE for 1 hour at 37° C. followed by treatment with RR1 (0-1000 µg/ml) overnight in the incubator. The secreted TNF-α in the medium was analyzed using ELISA (BD BIOSCIENCES, San Jose, Calif.).

NF-κB activity. RAW264.7 cells were incubated with 0, 100, 500 and 1000 µg/ml of RR1 for 8 hours and the nuclear proteins were extracted using the NF-κB activity kit from Active Motif, CA according to manufacturer's ELISA instructions. To visualize the NF-κB activation further, Electrophoretic Mobility Shift Assay (EMSA) was performed (Ghosh, S, and Karin, M., *Cell*, 2002, 109:S81-96; Young, S. H. et al. *J. Biol Chem.*, 2001, 276:20781-20787; Lebron, F. et al. *J Biol Chem.*, 2003, 278:25001-25008) with the nuclear protein. A double stranded probe that binds NF-κB (5'-AGT-TGAGGGGACTTTCCCAGC-3', SANTA CRUZ BIOTECHNOLOGY, Santa Cruz, Calif.) was radio labeled with $^{32}$P-ATP, and EMSA performed with 5 µg of nuclear extract. The EMSA reaction mixtures were incubated for 30 minutes at room temperature, and DNA-protein complexes were separated on 6% polyacrylamide gels and visualized by autoradiography. To determine the time-dependent activation of NF-κB, nuclear extracts were prepared from RR1 (100 µg/ml)-treated cells at different time periods (0, 4, 8, 14, 20 hours after stimulation). The nuclear extracts were analyzed for the protein content, and NF-κB activity analyzed using ELISA kit from ACTIVE MOTIF, Carlsbad, Calif.

I-κBα degradation. The degradation of IκB-α is a prerequisite for the activation of NF-κB. To determine the effect of RR1 on cellular IκB-α levels and its degradation, immunoblot analysis was performed with cytosolic lysates from RR1-treated RAW 264.7 macrophages for different time periods (0, 15 minutes, 30 minutes, 1 hour). The lysates were separated by SDS-PAGE on 12% gels and transferred to nitrocellulose membranes using a TransBlot apparatus (BIO-RAD, Hercules, Calif.). The membranes were hybridized with IκB-α specific monoclonal antibodies (1:1000) by the Western blot hybridization protocol (Lebron, F. et al. *J Biol Chem.*, 2003, 278:25001-25008) using antimouse IκB-α antibody (CELL SIGNALING TECHNOLOGY, Inc, Beverly, Mass.) using the color detection system (BIO-RAD, Hercules, Calif.).

Effect Blocking of CR3 with CD11b mAb on opsonised binding. To examine whether the glucan specific receptors CR3 is involved in the opsonised recognition/binding of RR1 on macrophages, monoclonal antibodies (mAbs) specific for CR3 (Rat antimouse CD11b from BD BIOSCIENCES, San Jose, Calif.) were used for blocking the CR3. RAW 264.7 cells ($0.5 \times 10^6$) were treated with 5 µg/ml of monoclonal antibody for 1 hour at 37° C. in the $CO_2$ incubator before incubating with RR1 (0-100 µg/ml) for 3 hours. TNF-α released by the macrophages into the medium was analyzed by ELISA kit (BD Biosciences, San Jose, Calif.) (Brown, G. D. et al. *J. Expt. Med.*, 2002, 196:407-412; Brown, G. D. et al. *J. Exp. Med.*, 2003, 197:1119-1124).

TLR signaling. To determine the involvement of TLR signaling, parental HEK293 as well as HEK293 cells transfected with human TLR2, TLR6, TLR2/6 or TLR4/CD14/MD2 genes (cloned into pDUO plasmid), were used. These cells ($0.5 \times 10^6$/ml) were incubated with 0-100 µg/ml of RR1 for 24 hours. Since these cells produce very low level of TNF-α and detectable levels of IL-8 upon activation, IL-8 secreted into the medium was analyzed using ELISA procedure. Incidentally, the IL-8 synthesis is also under the control of the transcription factor NF-κB.

TLR mRNA and protein levels. TLR2, 4 and 6 mRNA levels were analyzed by RT-PCR using total RNAs extracted from RR1 treated cells. Total RNA was extracted from RR1-treated and untreated RAW 264.7 cells and 0.5 µg/ml RNA was reverse transcribed and amplified using mouse TLR2, 4 and 6 specific PCR primers (R&D SYSTEMS, Minneapolis, Minn.). Mouse GAPDH gene was also amplified as a control. The PCR products were separated on agarose gel.

EXAMPLE 1

Characterization of RR-1

Figure 2A:
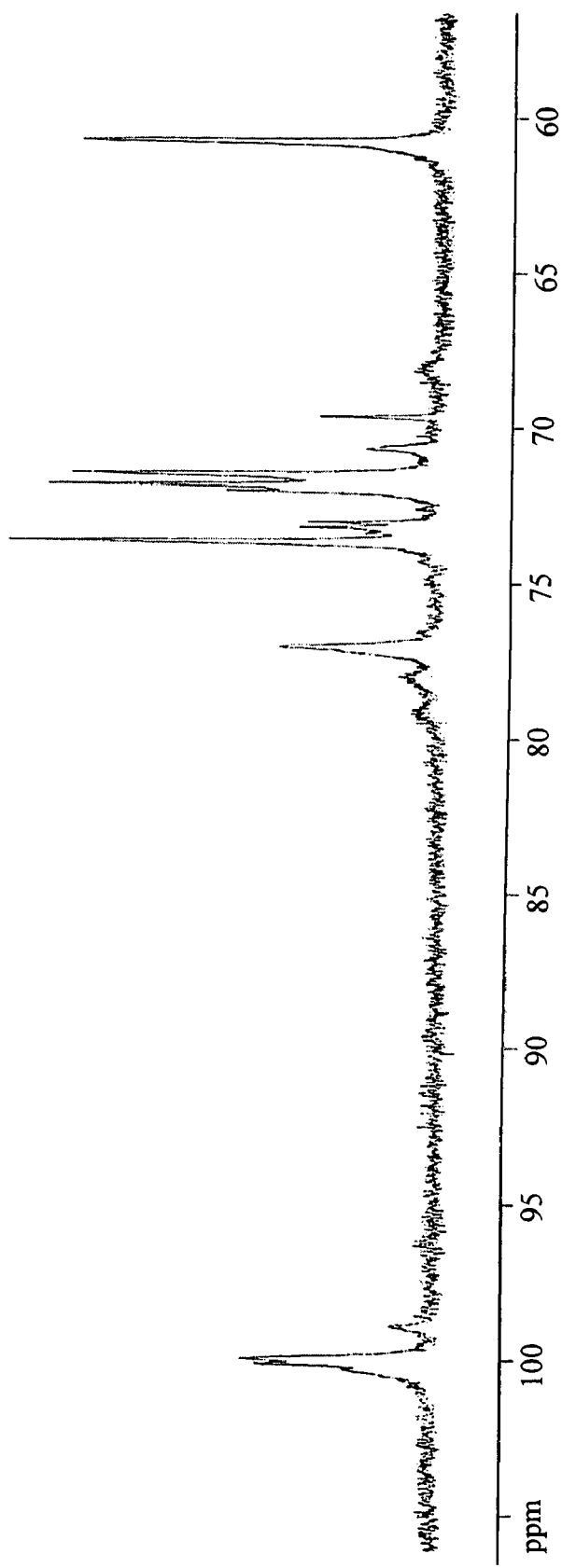
FIGS. 2A-2B show (a) $^{13}$CNMR spectra of RR1 in $D_2O$ showing (1-4) and (1-6) glycosidic linkages (b) 500 MHz protonNMR spectra of RR1 in $D_2O$ showing the α-conformation.
Figure 2B:
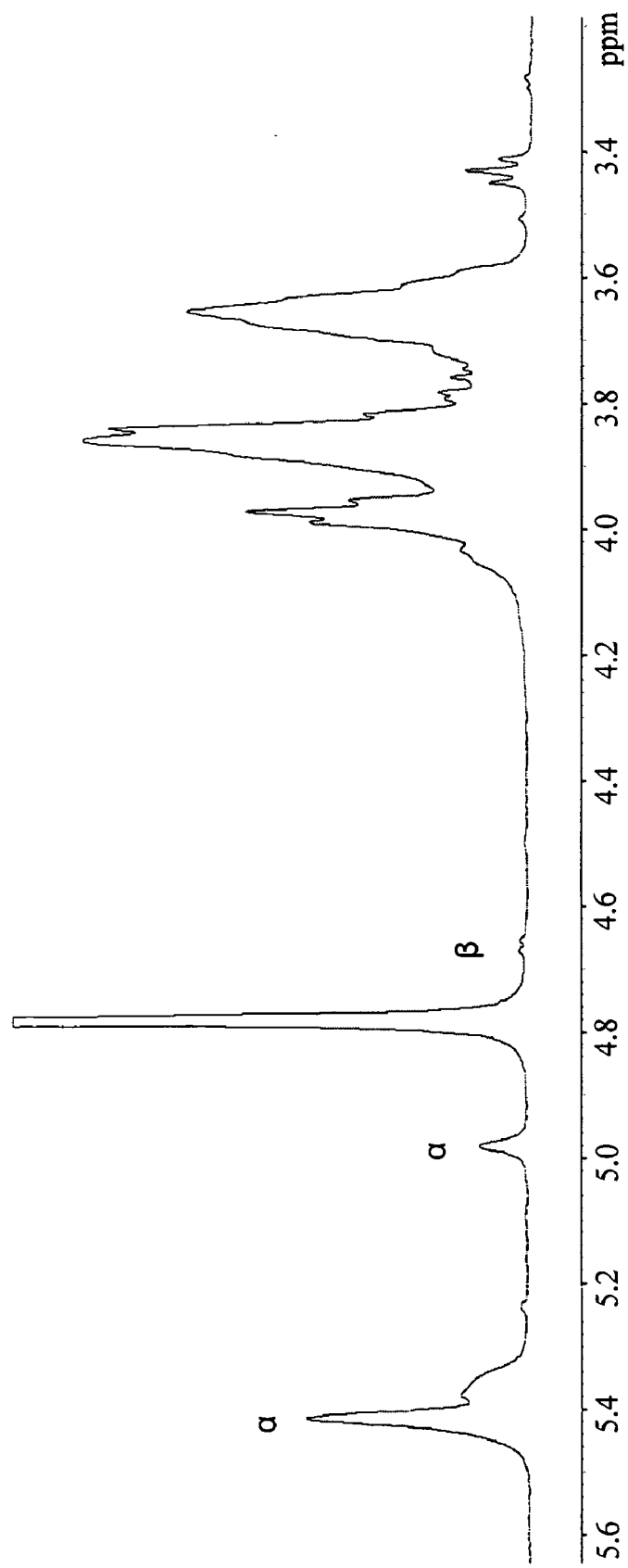

The results of the glycosyl composition and linkage analyses corroborated with initial findings and the $^{13}$C NMR spectral data on the carbohydrate composition of RR1. The glycosyl composition analysis showed glucose as the only component in RR1 while linkage analysis revealed three types of glucopyranosyl residues corresponding to three types of linkages: 4-linked glucopyranosyl residue (80%), 4,6-linked glucopyranosyl residue (12%) and terminal glucopyranosyl residue (8%). The $^{13}$C NMR spectra (FIG. 2A) showed well resolved signals for the carbon atoms in the glucopyranosyl moieties-C1 (δ 99.97 ppm), C2 (δ 73.68 ppm), C3 (δ 71.89 ppm), C4 (δ 77.09 ppm), C5 (δ 69.67 ppm) and C6 (δ 60.83 ppm). The downfield shifts in the C1 and C4 signals confirm the (1→4) linkage while the signal at δ 71.53 ppm may be due to the C6 of the (1→6) linkage. The signals at δ 5.44 ppm (not well resolved) and that at δ 5.00 ppm in the 500 MHz protonNMR spectra (FIG. 2B) are due to the a proton associated with the anomeric carbon of the glucopyranosyl units. On the other hand, the very weak signal at δ 4.66 ppm may be due to that of the β anomer. However, the ratio of the signals of α-D-glucose to β-D-glucose is about 99.9:1 and hence almost all glucose units appeared to be in the α configuration. Therefore, RR1 is a α-D-glucan with (1→4) linked glucopyranosyl units in the main chain with (1→6) linked glucopyranosyl unit branches and a 0.15 degree of branching (FIG. 3). In the size exclusion chromatography, RR1 eluted as a single peak at 12.32 minutes which was very close to the peak for the 511 kDa dextran sample (retention time: 12.72 minutes). Therefore, RR1 was assigned a molecular weight >550 kDa.

EXAMPLE 2

Non-cytotoxic/cell Proliferation Effect

Figure 4A:
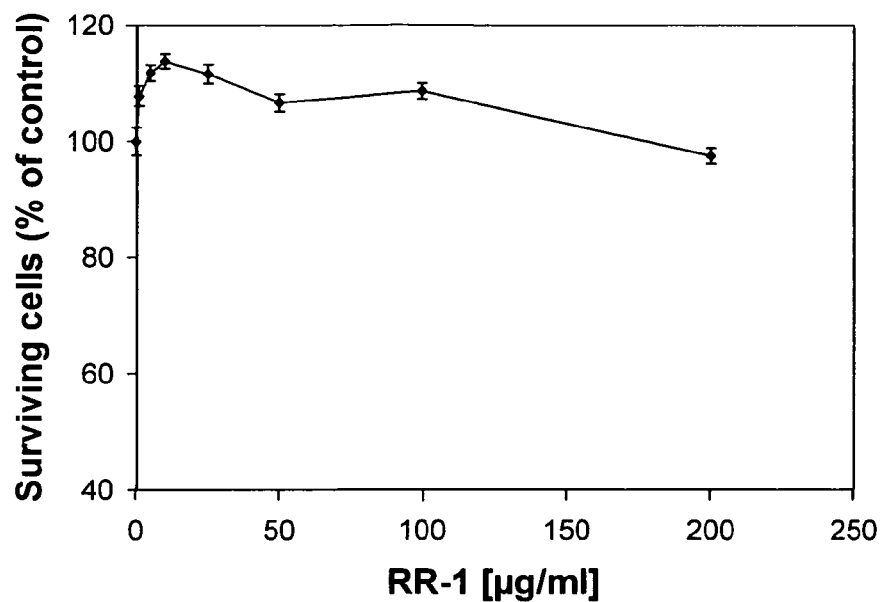
FIGS. 4A-4B show cytotoxic analysis of RR1 in normal lymphocytes (a) and tumor cell lines (b). Cells ($10^6$) were treated with RR1 for 24 hours and cytotoxicity assay performed using MTT cell proliferation kit (Roche Biochemicals). The percentage of surviving cells over control was plotted against RR1 concentrations.
Figure 4B:
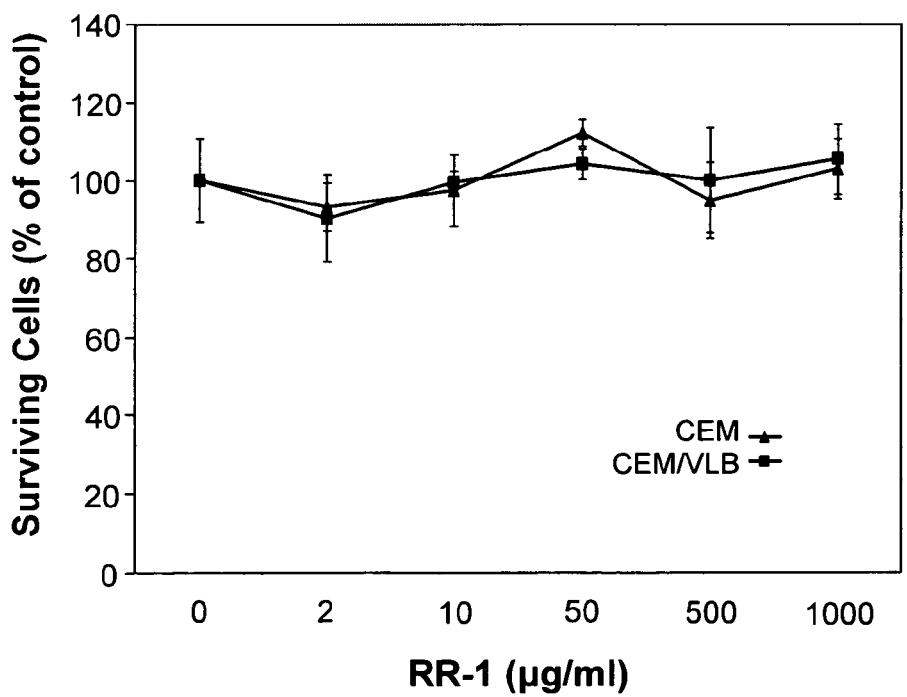

The results of the MTT assay displayed in FIGS. 4A and 4B show that RR1 has no direct cytotoxic or cell proliferating effect, either on normal lymphocytes or on tumor cell lines (CEM and CEM/VLB) at concentrations as high as 1000 µg/ml.

EXAMPLE 3

Lymphocyte Activation

Figure 5:
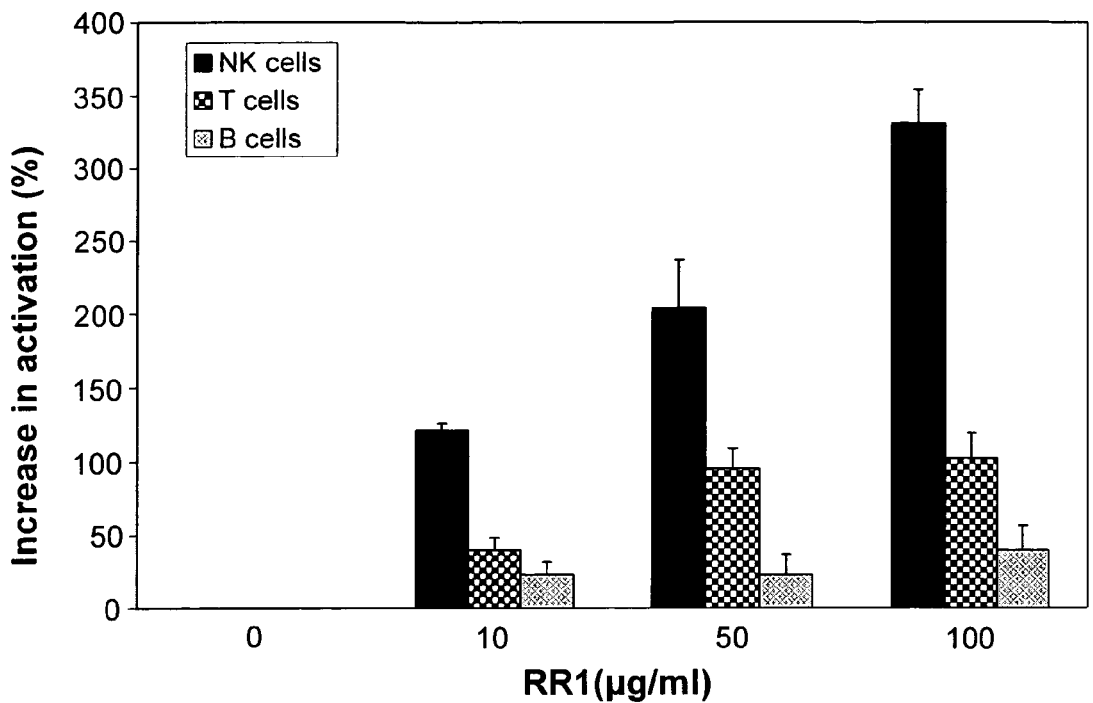
FIG. 5 shows flow cytometric analysis of Activation of NK, T and B cells by RR1. Normal lymphocytes were treated with RR1 (0-100 μg/ml) for 24 hours at 37° C. in a $CO_2$ incubator. The cells were stained with a panel of cell specific antibodies conjugated with different fluorochromes: CD3-FITC, CD16/56-PE, CD19-ECD, CD69-PC5 or CD8-FITC, CD4-PE, CD3-ECD, CD69-ECD. The stained cells were analyzed in a Coulter Elite flow cytometer in a 4-color assay. ***$p<0.001$.
Figure 6:
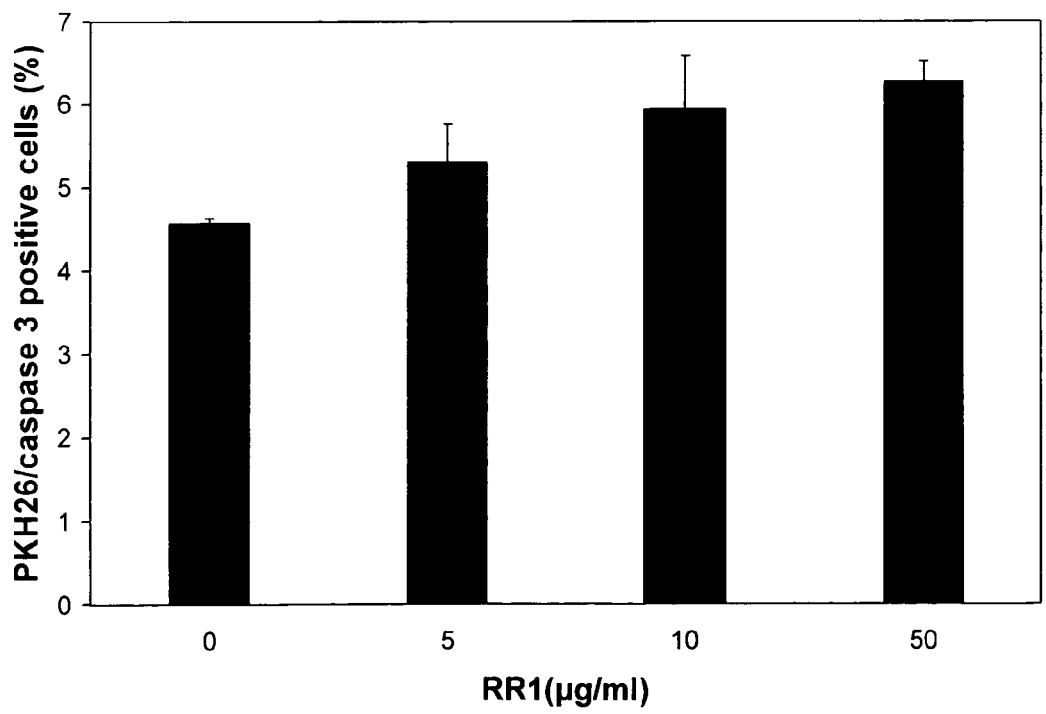
FIG. 6 shows flow cytometric assay for cytotoxicity of RR1 activated human lymphocytes. Normal lymphocytes were treated with RR1 (0-100 μg/ml) for 24 hours in RPMI medium. The cells were washed and co-incubated with PKH26-labeled human leukemic CEM cells for 12 hours for the active NK cells to lyse the tumor cells. The cell mixtures were stained with FITC-labeled and activated caspase-3 monoclonal antibody. The percentage of PKH26+ and Caspase-3+ cells were quantified by analyzing in a Beckman-Coulter Elite flow cytometer (**$p=0.01$).

Lymphocytes are the key effecter cells of the mammalian immune system and these studies show that the different subpopulations of lymphocytes are activated by RR1 at varying levels. B cells are activated by 39%, T cells by 102% and NK cells 331% with 100 µg/ml of RR1 (FIG. 5). The >3 fold activation of NK cells is of high significance, as NK cells are the main effecters of the innate immune system that comes into contact with antigens/mitogens before antibody production and recognition by the adaptive immune system. The increased activity of NK cells by RR1 is quite evident from the results of the functional cytotoxic assay, shown in FIG. 6. RR1-treated normal lymphocytes were able to kill a higher percentage of tumor cells compared to untreated cells and a dose-dependent enhancement of cytotoxicity of activated lymphocytes was evident.

EXAMPLE 4

Complement Activation Pathway

Figure 7:
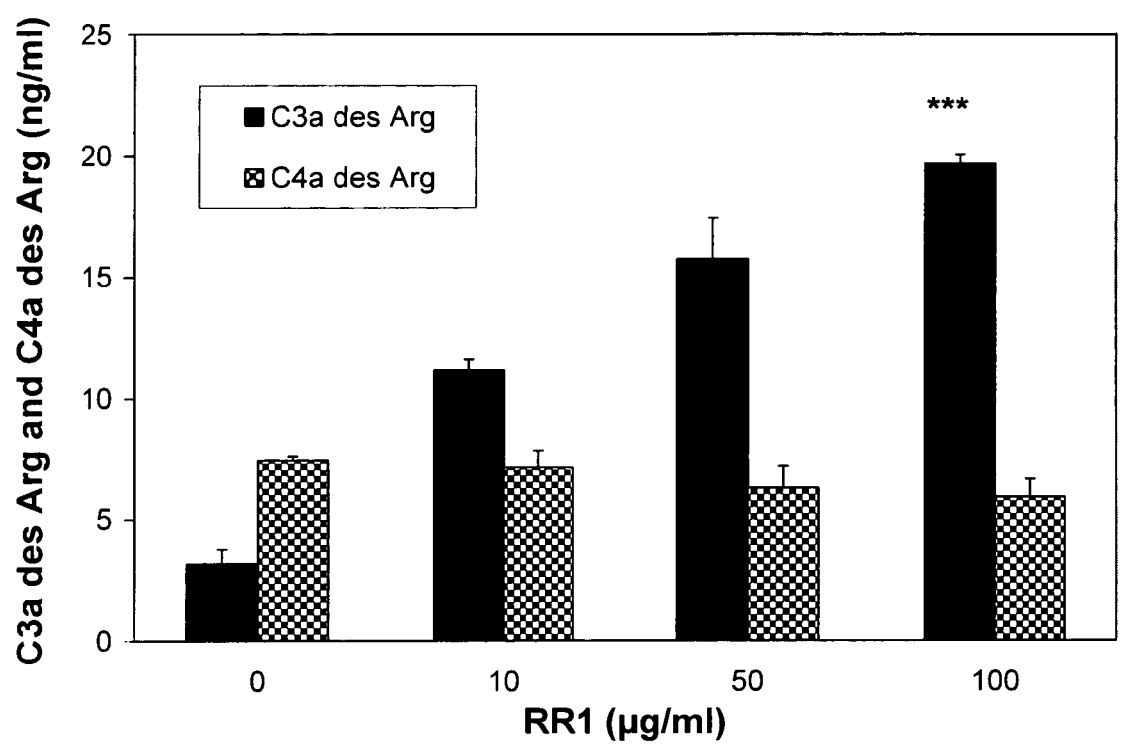
FIG. 7 shows analysis of RR1-induced activation of complement pathways. Normal blood samples from healthy volunteers were incubated with RR1 (0-100 μg) for 24 hours. Human complement C3a des Arg and C4a des Arg correlate EIA Kits (Assay Design Inc., Ann Arbor, Mich.) were used for quantification of classic and alternative pathway of complement activation using an ELISA procedure. ***$p<0.001$.

A step-wise increase in the levels of C3a des Arg of the alternative pathway was noticed with an increase in concentrations of RR1, as shown in FIG. 7. This observation is analogous with several reports on complement activation by other polysaccharides. C3a and C4a are bioactive cleavage products released from plasma components C3 and C4 during the complement activation cascade in alternative and classical pathways (Ember, J. A. et al. The Human complement system in Health and Disease, Ed. Volnakis, J. E. and M. M. Frank, Marcel Dekker Inc., New York, 1998, pp. 241-248), which are quickly converted to less active C3a-des Arg and C4a-des Arg forms and are involved in the mediation of cellular immune responses. The alternative pathway is self-amplifying and is important in the clearance and recognition of pathogens in the absence of antibodies (Stahl, G. M. et al. *Am. J. Pathol.*, 2003, 162:449-455). β-glucans are reported to activate the alternative pathway and the host-mediated antitumor activity exhibited by these polymers was correlated with the activation of the complement system (Hamuro, J. et al. *Am. J. Pathol.*, 1978, 93:526-617). Lipopolysaccharides activate the complement system via alternative as well as classical pathways; the lipid part activates the classical pathway while the polysaccharide moiety activates the alternative pathway (Morrison, D. C. and R. J. Ulevitch *Am. J. Pathol.*, 1978, 93:526-617).

EXAMPLE 5

Synthesis of Cytokines

Figure 8A:
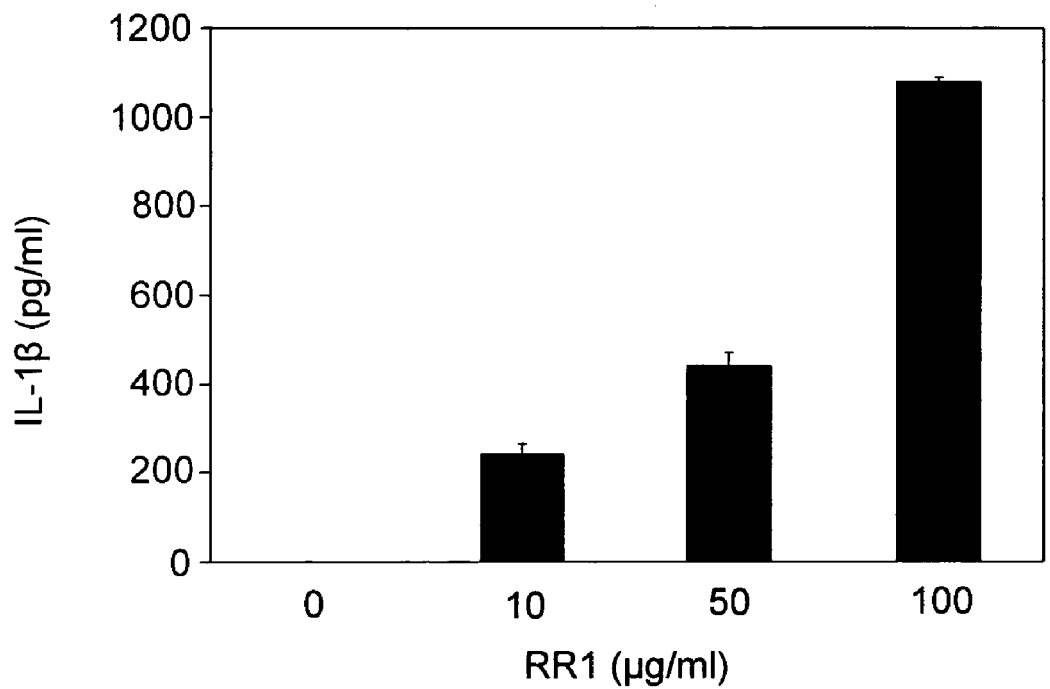
FIGS. 8A-8H show synthesis of cytokines and chemokine in RR1-induced normal lymphocytes. Normal lymphocytes from healthy volunteers were treated with RR1 (0-100 μg) at 37° C. for 24 hours in a $CO_2$ incubator in RPMI medium. The supernatant medium was analyzed for the production of cytokines and chemokine in an ELISA procedure using reagent kits (BD Biosciences). RR1 induced the synthesis of IL-1β, IL-6, IL12p40, IL-12p70, and IL-18, TNF-α, IFN-γ, and MCP-1 significantly (***$p<0.001$).
Figure 8B:
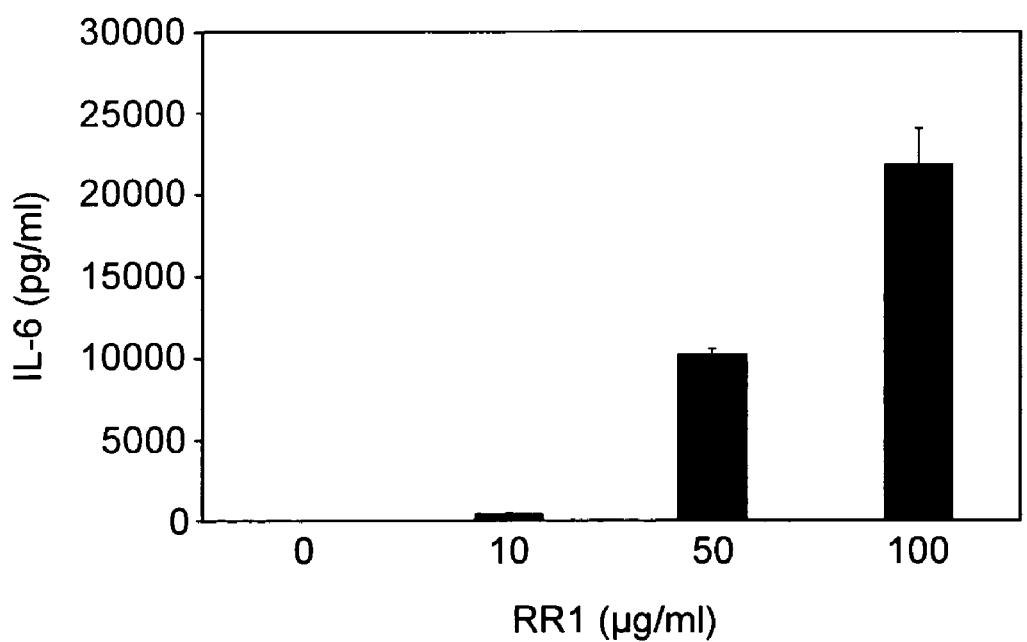
Figure 8C:
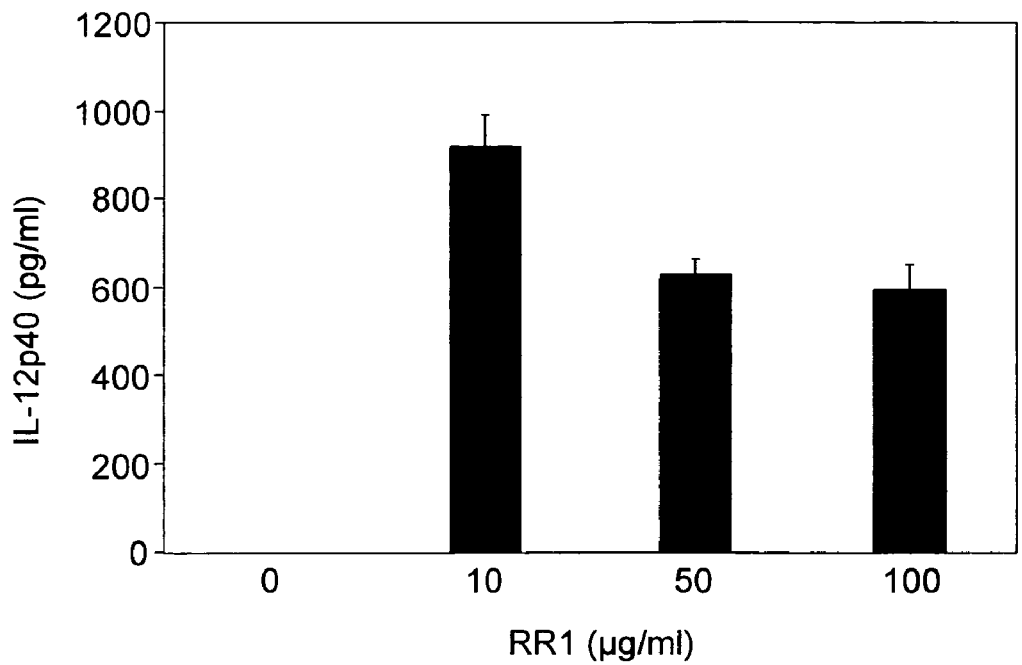
Figure 8D:
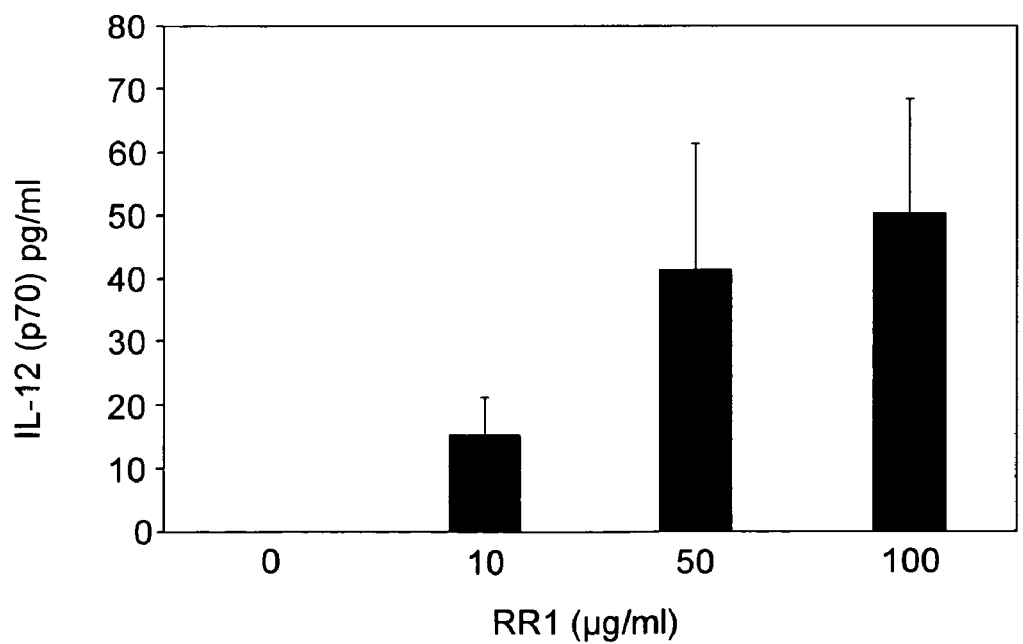
Figure 8E:
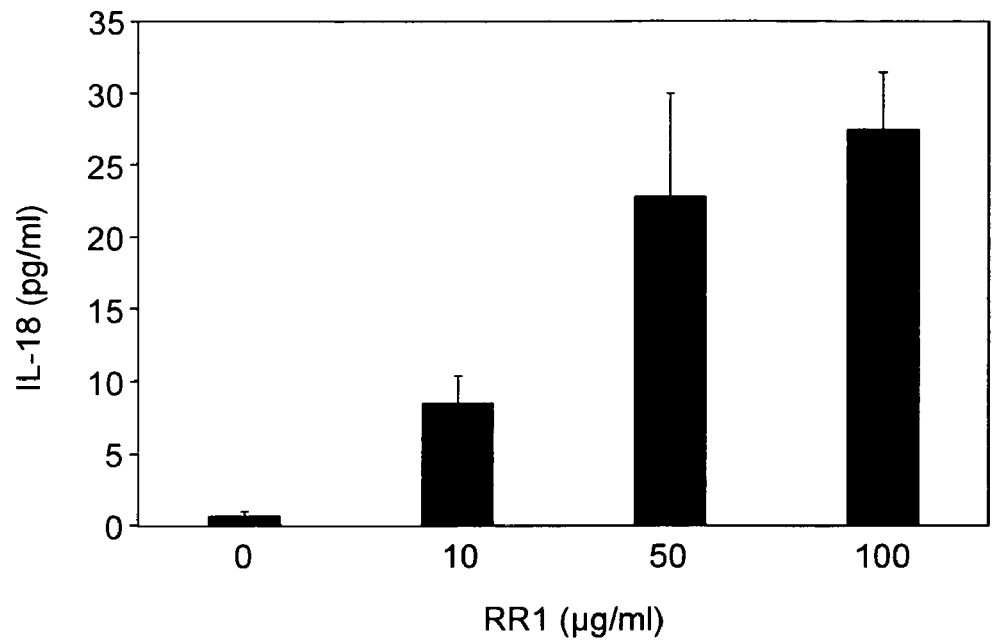
Figure 8F:
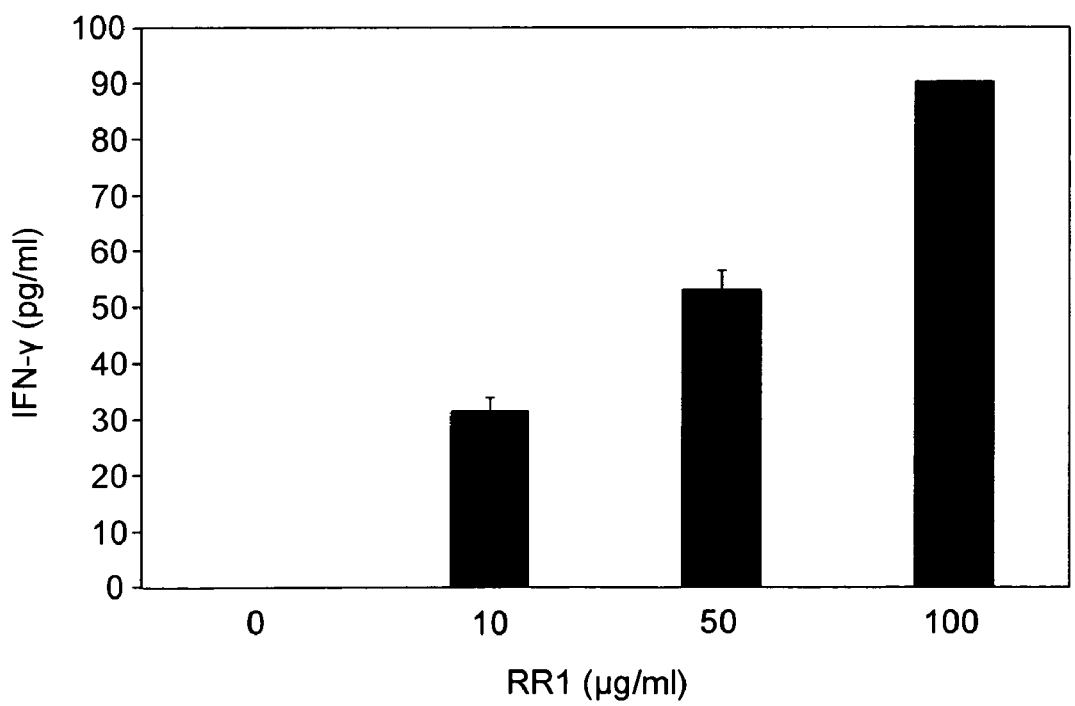
Figure 8G:
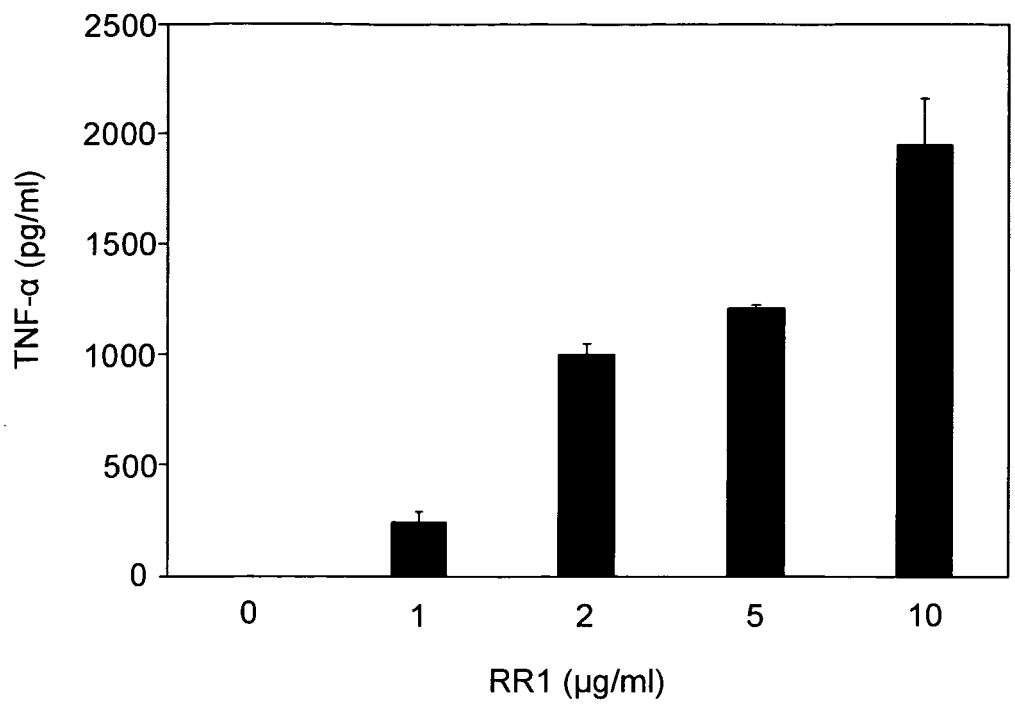
Figure 8H:
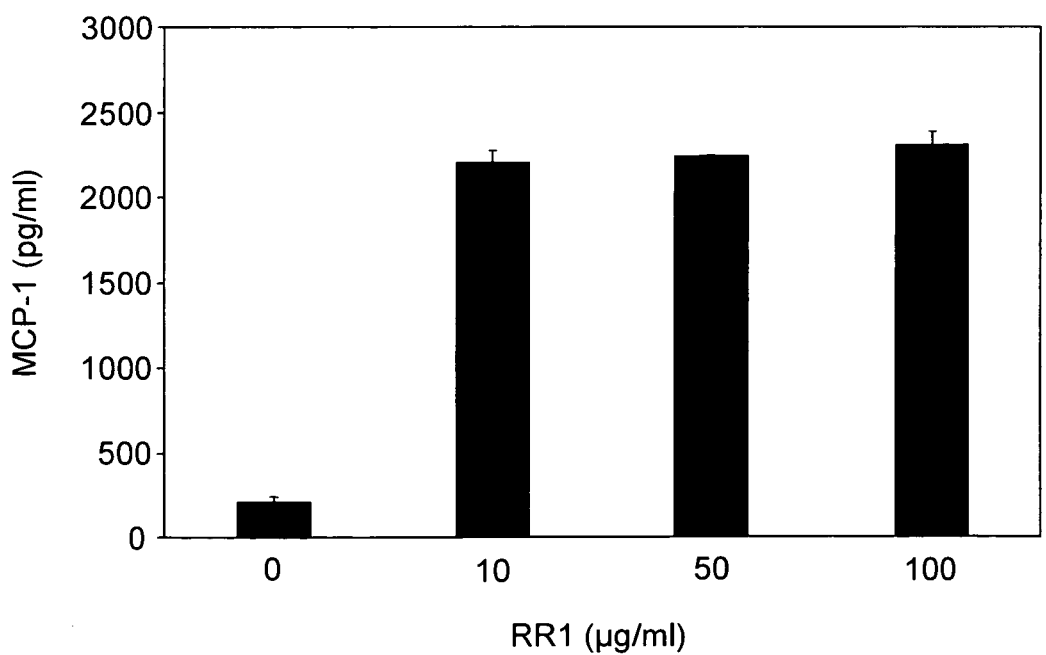

As shown in FIGS. 8A-8H, RR1 induced the synthesis of IL-1β (1080 pg), IL-6 (21833 pg), IL-12 p40 (918.23 pg), IL-12 p70 (50.19 pg), IL-18 (27.47 pg), IFN-γ (90.16 pg), MCP-1 (2307 pg) and TNF-α (2225 pg), but did not induce the production of IL-2, IL-4, IL-10, TNF-β and IFN-α. In general, a dose-dependent increase in the production of cytokines was observed with RR1 except for IL-12 (p40), in which the maximum was recorded at 10 µg/ml and further increase in the RR1 exhibited a decreasing trend, as shown in FIG. 8C. MCP-1 production was very significant up to 10 µg/ml of RR-1 and higher RR1 concentration produced only slight increase, as shown in FIG. 8H. In general, pro-inflammatory cytokines IL-1β, IL-6, and TNF-α, and the regulatory cytokine IL-12 p(40) exhibited higher levels of production compared to other cytokines.

The mammalian immune system recognizes antigens, pathogens and non-self molecules, which trigger defense mechanisms through the activation of immune competent cells, production of chemical messengers (the cytokines and chemokines), activation of complement cascade pathway, and synthesis of nitric oxide (NO). Cytokines are a group of low molecular weight regulatory non-antibody proteins secreted by immune component cells in response to stimulation. They bind to specific receptors of target cells triggering signal transduction pathways that ultimately lead to gene expression in target cells. Cytokines regulate the intensity and duration of immune responses by stimulating or inhibiting activation, proliferation and/or differentiation of various cells and by regulating the secretion of antibodies or other cytokines. The pleiotropy, redundancy, synergy and antagonism exhibited by cytokines permit them to coordinate and regulate cellular activities. Inflammatory responses are crucial in controlling and eliminating infectious agents as well as in promoting wound healing for restoration of tissue integrity.

IL-1β and TNF-α induce the production of each other, as well as that of IL-6, and act synergistically and regulate several biological actions, besides IL-1 being self-inductive (Horai, R. et al. *J. Exp. Med.*, 2000, 191:313-320). The production of IL-1β and TNF-α in RR1 treated lymphocytes is consistent with that in the LPS stimulated human monocyte cell lines (THP-1) (Baqui, A. A. et al. *Clin. Diagn. Lab. Immunol.*, 1998, 5:341-347). IL-12 (p70) is the bioactive isoform of IL-12 and is an important factor in the differentiation of naive T cells into effecter T helper type 1 ($Th_1$) CD4+ lymphocytes secreting IFN-γ (Trinchieri, G. et al. *Prog. Growth Factor Res.*, 1992, 4:355-368). In addition, it is also reported to have stimulatory effects on NK cells (Wajchman, H. J. et al. *Cancer Res.*, 2004, 64:1171-1180). Recently, IL-12 (p70) has emerged as an efficient and minimally toxic antitumor cytokine due to its ability to elicit the $Th_1$ response (Hiscox, S. and Jiang, W. G. *In Vivo*, 1997, 11:125-132). Beyond the immune system, this cytokine is also reported to have the capacity to inhibit UV-induced apoptosis and initiation of DNA repair in UV damaged keratinocytes which ultimately protect the cells from malignancy (Schwarz, A. et al. *Nat. Cell Biol.*, 2002, 4:26-31). IL-12(p40), the homodimeric isoform, is a receptor antagonist of the bioactive heterodimeric isoform p70 in mouse (Gillessen, S. et al. *Eur. J. Immunol.*, 1995, 25:200-206). In the RR1-treated cells, IL-12 (p40), the regulatory cytokine, is produced in many fold excess to the bioactive form which may be a natural mechanism to control the over-production of the bioactive form p70. IL-18 is another potent inducer of IFN-γ and, apparently, NK cells (Micallef, M. J. et al. *Eur. J. Immunol.*, 1996, 26:1647-1651). RR1 induction of IL-18 production may be an early response in the development of $Th_1$ response, acting in consonance with IL-12 and IFN-γ.

MCP-1 is a potent chemo-attractant for monocytes and activated CD4 and CD8 T cells that is reported to induce granule release from NK and CD8+ cells, activate NK function in CD56+cells, and act as a potent releasing factor for histamine from basophiles (Rollins, B. J. *Blood*, 1997, 90:909-928). Further, it is reported to exhibit antitumor effects by enhancing tumor specific immunity, presumably in a T cell dependent manner (Laning, J. et al., *J. Immunol*, 1994, 153:4625-4635). Observations made by the present inventors indicate that RR1 induces the production of this cytokine significantly at 10 µg/ml. The significant synthesis of TNF-α by RR1 stimulation may play a critical role in host resistance to infections and to the growth of malignancy. TNF-α and its receptors are essential for protection against tuberculosis and for NO synthesis in macrophages early in infection (Lipton, S. A. *Neurochem. Int.*, 1996, 29:111-114). RR1-induced IFN-γ production may function in part to promote the activity of the components of the cell-mediated immune system such as Cytotoxic T Lymphocytes (CTLs), macrophages and NK cells in addition to its inhibitory role in $Th_2$ response. It stimulates the bactericidal activity of phagocytic cells and, therefore, boosts the innate immune response (Watford, W. T.

et al. *Cytokine Growth Factor Rev.*, 2003, 14:361-368). Moreover, it may modulate MCP-1 synthesis in macrophages as in LPS (Munder, M. et al. *J. Exp. Med*, 1998, 187:2103-2108).

CD4+ T cells contribute to the regulation of antigen specific (adaptive) immune system through the recognition of antigens and consequent production of cytokines. The distinct pattern of cytokine production by CD4+ cells form a dichotomy, Type 1 ($Th_1$) characterized by IFN-γ production and promotes elimination of intracellular pathogens and Type 2 ($Th_2$) characterized by IL-4 production, involves IgE and eosinophils suitable for elimination of extra cellular pathogens. Cytokines act directly on T cells during primary activation and appears to be the most direct mediator among the factors influencing the terminal differentiation. The presence of IL-12 leads to $Th_1$ response while IL-4 leads to $Th_2$ development and the two pathways express mutually suppressive effect as well. IL-1 is identified as an inducer of IL-12 (Rollins, B. J. *Blood*, 1997, 90:909-928) while IL-18 is an early response in the development of $Th_1$ cells by induction of IFN-γ. The cytokine profile, IL-12, IL-18, IFN-γ together with IL-1 by RR1 stimulation and the dose-dependent synthesis of these cytokines clearly demonstrate the $Th_1$ pathway which is essential for cellular immunity and killing of intracellular pathogens and malignant cells. This observation is in conformity with IL-12-induced, IFN-γ-dependent T cell development to $Th_1$ and CD8+ cytotoxic effector cells (Russo, D. M. et al. *Expt. Parasitol.*, 1999, 93:161-170; Yoshimoto, T. et al. *J. Immunol.*, 1998, 161:3400-3407; Russo, D. M. et al. *Infect. Immun.*, 2000, 68:6826-6832). Concurrent signaling as well as synergistic action by IL-12 and IL-18 induces prolonged IFN-γ production and the continuous strong expression of IL-18R mRNA in T cells (Yoshimoto, T. et al. *J. Immunol.*, 1998, 161:3400-3407). The early inflammatory events such as T cell adhesion to inflammatory sites was also reported for IL-12 and IL-18 (Ariel, A. et al. *J. Leuk. Biol.*, 2002, 72:192-198). The higher level of the synthesis of the regulatory isoform of IL-12 (p40) may be a natural mechanism to contain the excessive production of the $Th_1$ response.

Figure 9:
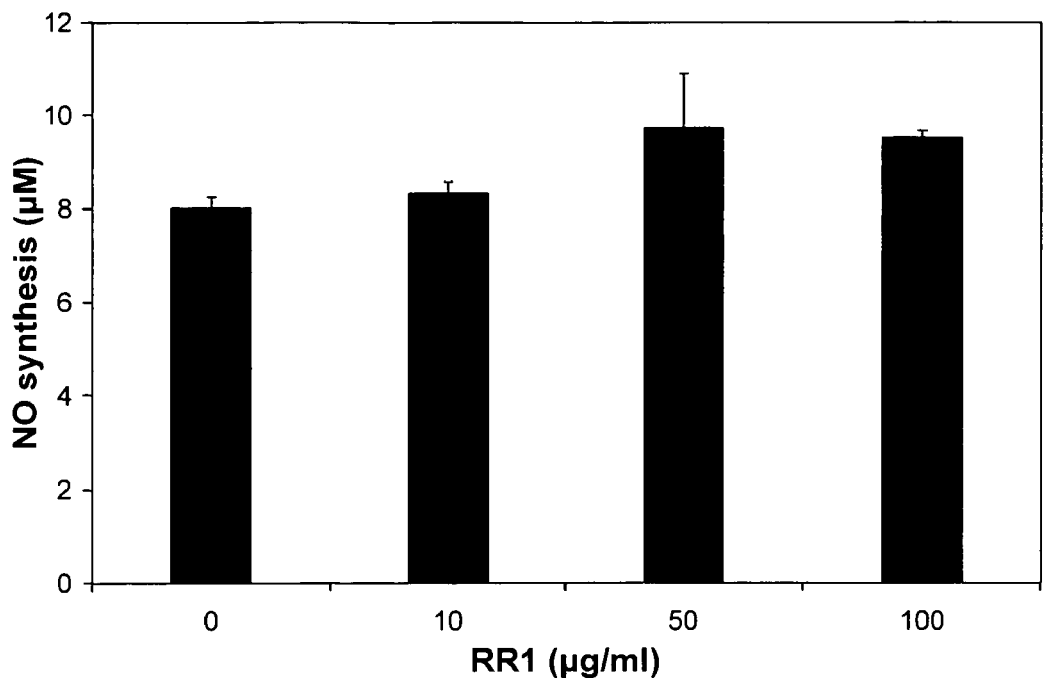
FIG. 9 shows RR1-induced NO synthesis in normal lymphocytes. Normal lymphocytes from healthy volunteers were treated with RR1 (0-100 μg) at 37° C. for 24 in a $CO_2$ incubator in MEM medium. The supernatant medium was analyzed for the production of NO using assay kit from Active Motif, Carlsbad, Calif. and data analyzed using ANOVA ($p=0.109$).

NO levels are also reported to play an important role in the modulation of Th cell differentiation and polarization. Yamasaki et al. (Yamasaki, A. et al. *Yonago Acta Medica*, 1998, 44:7-15) and Taylor-Robinson et al. (Taylor-Robinson, A. W. et al. *Eur. J. Immunol.*, 1994, 24:980-984) reported an inhibitory role of NO on $Th_1$ cytokines while Bauer et al. (Bauer, H. et al., *Immunol*, 1997, 90:205-211) reported the same for $Th_1$ as well as $Th_2$ cytokines by NO from activated T cells. In the present study, RR1 treatment induced only ≦21% increase in NO (FIG. 9). The enzyme iNOS produced a high output of NO from macrophages upon stimulation. The present investigations revealed that RR1 did not stimulate the induction of iNOS significantly. The absence of iNOS induction by RR1 supports the conclusion that there is an insignificant increase in the production of NO. The present investigations with monocytes isolated from peripheral blood mononuclear cells by Monocyte Isolation kit II (Miltenyi Biotec, Germany) or with human monocyte cell line THP-1 (ATCC) also did not induce any higher levels of NO with RR1 treatment. The low level of NO synthesis by RR1 does not appear to exert any inhibition of the $Th_1$ pathway. IFN-α, IFN-γ and TNF-α are known up-regulators of NO synthesis (Shin, J. Y. et al. *Immunopharmcol. Immunotoxicol.*, 2002, 24:469-482; Hirazumi, A. and Furusawa, E. *Phytother Res.*, 1999, 13:380-387). As RR1 stimulation resulted in the synthesis of IFN-γ and TNF-α, and very little IFN-α, it is reasonable to assume that IFN-α priming may be a necessary step for triggering the production of higher levels of NO by polysaccharides (Ring, A. et al. *J. Infect. Dis.*, 2002, 186: 1518-1521).

RR1 stimulation does not produce any oxidative stress in lymphocytes, indicated by the levels of the GSH, GSSG, and their ratio (Table 1), corresponding to the NO synthesis data. No significant elevation in the amount of hydrogen peroxide was observed (data not shown). The low level of the synthesis of NO suggests an immune mediatory role for NO. The non-cytotoxic nature of RR1, even at fairly high concentrations (1000 µg/ml), may be attributed to the low level production of NO together with the ability of this polysaccharide not to induce oxidative stress in the cells.

TABLE 1

GSH, GSSG, and GSH/GSSG ratio of Normal Lymphocytes treated with RR1

| RR1 (µg/ml) | GSH (µM) | GSSG (µM) | GSH/GSSG |
|---|---|---|---|
| 0 | 367.09 ± 4.4 | 22.60 ± 0.44 | 14.56 ± 0.69 |
| 5 | 365.08 ± 3.81 | 22.77 ± 0.58 | 14.05 ± 0.41 |
| 10 | 366.10 ± 0.97 | 22.67 ± 0.41 | 14.34 ± 0.35 |
| 50 | 364.43 ± 0.10 | 22.75 ± 0.55 | 14.25 ± 0.40 |

Immune stimulation by induction of cytokines and synthesis of NO, activation of macrophages, induction of phagocytic, cytotoxic, and antitumor activities have been reported recently in polysaccharide or polysaccharide containing fractions of *Phanax ginseng*, *Morinda citrifolia*, and *Echinacea* (Shin, J. Y. et al. *Immunopharmcol. Immunotoxicol.*, 2002, 24:469-482; Hirazumi, A. and Furusawa, E. *Phytother Res.*, 1999, 13:380-387; Goel, V. et al. *J. Nutri. Biochem*, 2002, 13:487-492). RR1 is a α-D-glucan structurally distinct from amylopectin as the later cannot induce any immune stimulation. The similarity of its structure to the "conserved molecular pattern" of the cell wall components of fungal β-glucans may be the reason for the activation of the immune system, while the differences (i.e., the a conformation and the (1→4) linkages) may account for the low-level production of NO and the consequent non-cytotoxicity. This water soluble, neutral α-glucan has molecular mass and a branching sequence well within the range of the polysaccharides exhibiting significant immune stimulant properties (Bohn, J. A. and N. BeMiller *Carbohydr. Polymers*, 1995, 28:3-14; Brown, G. D. and S. Gordon Immunity, 2003:19:311-315; Kulicke, W. M. et al. *Carbohydr. Res.*, 1997, 295:135-143; Bao, X. et al. *Carbohyd. Res.*, 2001, 336:127-140). The water solubility can overcome the granuloma formations exhibited by particulate β-glucans while the high molecular mass, being in the most potent range, enables it to be retained by the host's organs for a longer period without degradation (Williams, D. L. et al. *Clin. Immunotherapy*, 1996, 5:392-396; Nono, I. et al. *Pharmacobiodyn.*, 1991, 14:9-19; Suda, M. et al. *FEMS Immunol. Med. Microbiol.*, 1996, 15:93-100).

The noncytotoxic nature, the significant activation of the lymphocytes, especially the NK cells, and the alternate pathway of complement activation, clearly demonstrate stimulation of the innate immune system, while the cytokine profile resulting from the activation unequivocally proclaims the stimulation of the antigen-specific cell-mediated (adaptive) immunity ($Th_1$ pathway) with a self-regulating mechanism of its excess production. The absence of IL-4 synthesis ($Th_1$ suppressor cytokine) and IL-10 (the inhibitor of IL-12) on stimulation with RR1 is in good agreement with the $Th_1$ pathway of T cell differentiation. The IFN-γ production by the concurrent signaling of IL-12 and IL-18 may serve as a potent anti-anthrax agent, devoid of side effects, if any, of the exogenous IFN treatment, as well. A stimulated innate immune system can fight the entry of any pathogens into the host and has the capacity to prevent primary infections from actually causing disease (Parham, P. Nature, 2003, 423:20). The unique immune stimulating properties of RR1, without exerting oxidative stress and any direct cytotoxic effect, thus far described, can make it as a potent bio-defense agent against a number of pathogens and human malignancies.

EXAMPLE 6

Effect of RR1 on Nonopsonic Binding of Zymosan A-FITC Bioparticles

Figure 10:
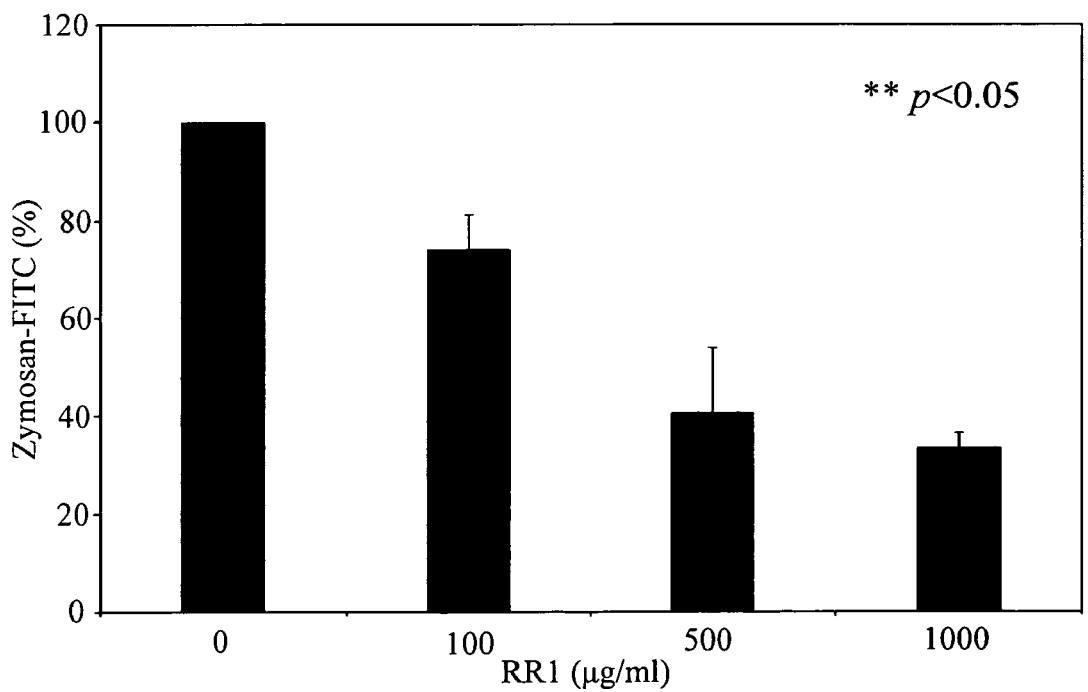
FIG. 10 shows the inhibitory effect of RR1 on nonopsonic recognition/binding of FITC-labeled zymosan A bioparticles on RAW264.7 macrophages. RR1 inhibits the binding and internalization of nonopsonic binding of zymosan A bioparticles in a dose-dependent manner. The cells were incubated with RR1 for 1 hour on ice (4° C.) in DMEM containing 0.5% FBS followed by zymosan A biparticles for 1 hour on ice. The cells were warmed for 7 minutes at 37° C. for internalization of zymosan A bioparticles and intracellular FITC fluorescence analyzed in a Coulter Elite flow cytometer.

FIG. 10 shows the inhibitory effect of RR1 on the nonopsonic recognition and binding of FITC-labeled zymosan A bioparticles to macrophages. A dose-dependent inhibition in the fluorescence intensity is observed with increase in concentration of RR1 with about 65% inhibition at 1000 μg/ml RR1 concentration. The incubation of cells at 4° C. during the experimentation will prevent the release of opsonins, thus facilitating nonopsonic binding.

EXAMPLE 7

Effect of RR1 on Opsonized Binding and Phagocytosis

Figure 1:
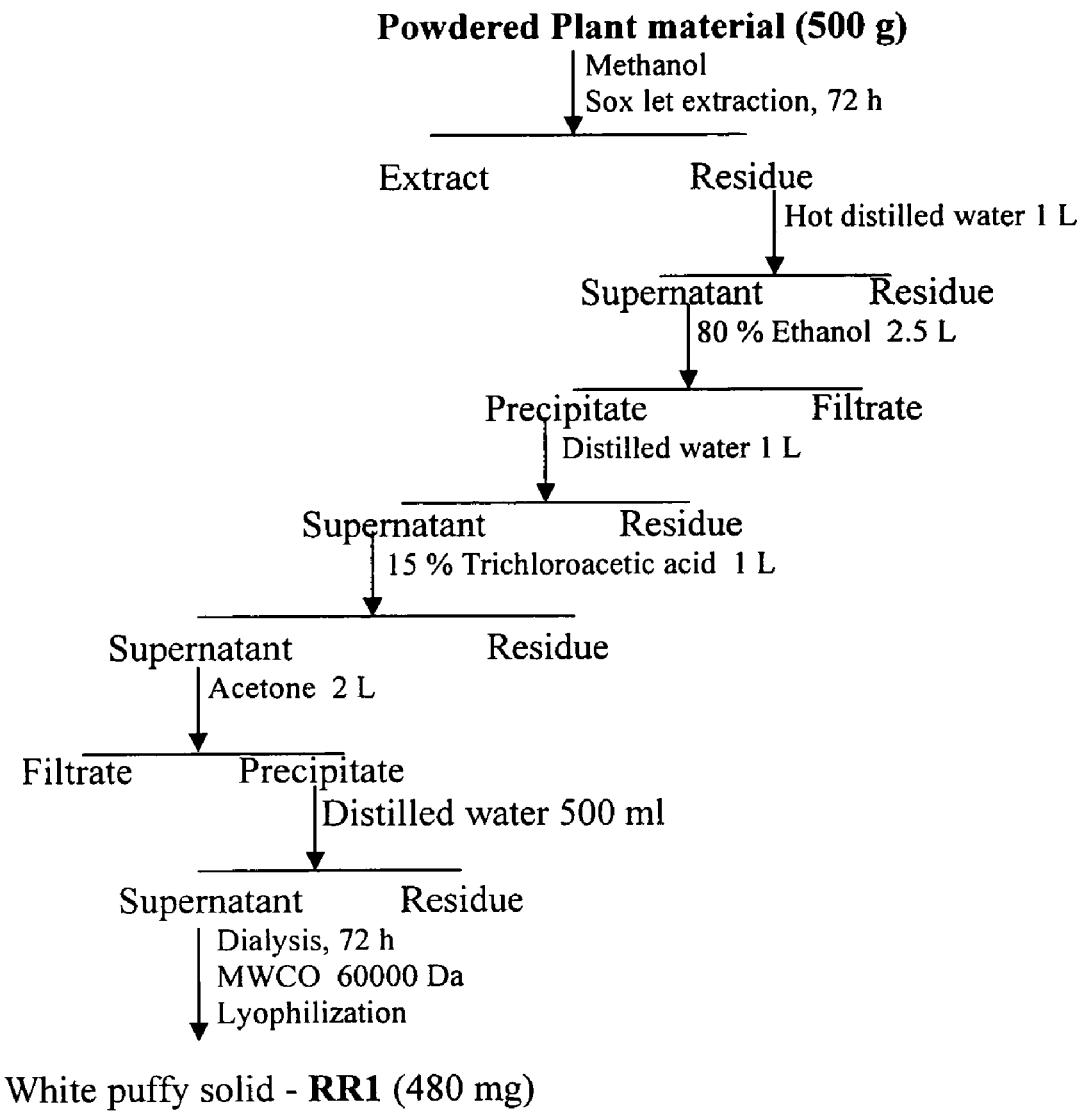
FIG. 1 shows a flow diagram describing the isolation of RR1.

The inhibitory effect of RR1 and laminarin on the phagocytosis of zymosan A bioparticles at 37° C. is presented in FIG. 1. Laminarin, a structurally defined β-glucan, has absolute inhibitory effect on the phagocytosis, where as RR1 failed to show any significant effect. Phagocytosis involves the binding and internalization of particles by macrophages.

EXAMPLE 8

Involvement of CR3 on RR1 Effect

CR3 is a β-glucan specific receptors involved in the opsonized binding of polysaccharides on monocytes leading to macrophage activation and inflammatory response. Incubation of monocytes with CR3 (CD11b) specific monoclonal antibodies at 5 μg/ml followed by RR1 incubation failed to inhibit or reduce the TNF-α synthesis of RAW 264.7 cells. However, significant reduction (41.31%) in TNF-α synthesis was observed when RAW 264.7 macrophages were treated with CD11b antibody followed by soluble zymosan (Table 2).

TABLE 2

TNF-α synthesis in RAW264.7 macrophages after anti-CD11b (CR3 specific) inhibition of opsonized binding of glucans

| Glucan | % reduction of secreted TNF-α |
|---|---|
| Control | 0 |
| Zymosan A (100 μg/ml) | 41.31 ± 6.90** |
| RR1 (100 μg/ml) | 4.25 ± 3.66 |
| RR1 (500 μg/ml) | 1.89 ± 0.50 |

Cells were incubated with CR3 (5 μg/ml) for 2 h followed by glucan treatment for 1 h at 37° C.
**$p < 0.05$

EXAMPLE 9

TNF-α Synthesis

Figure 12:
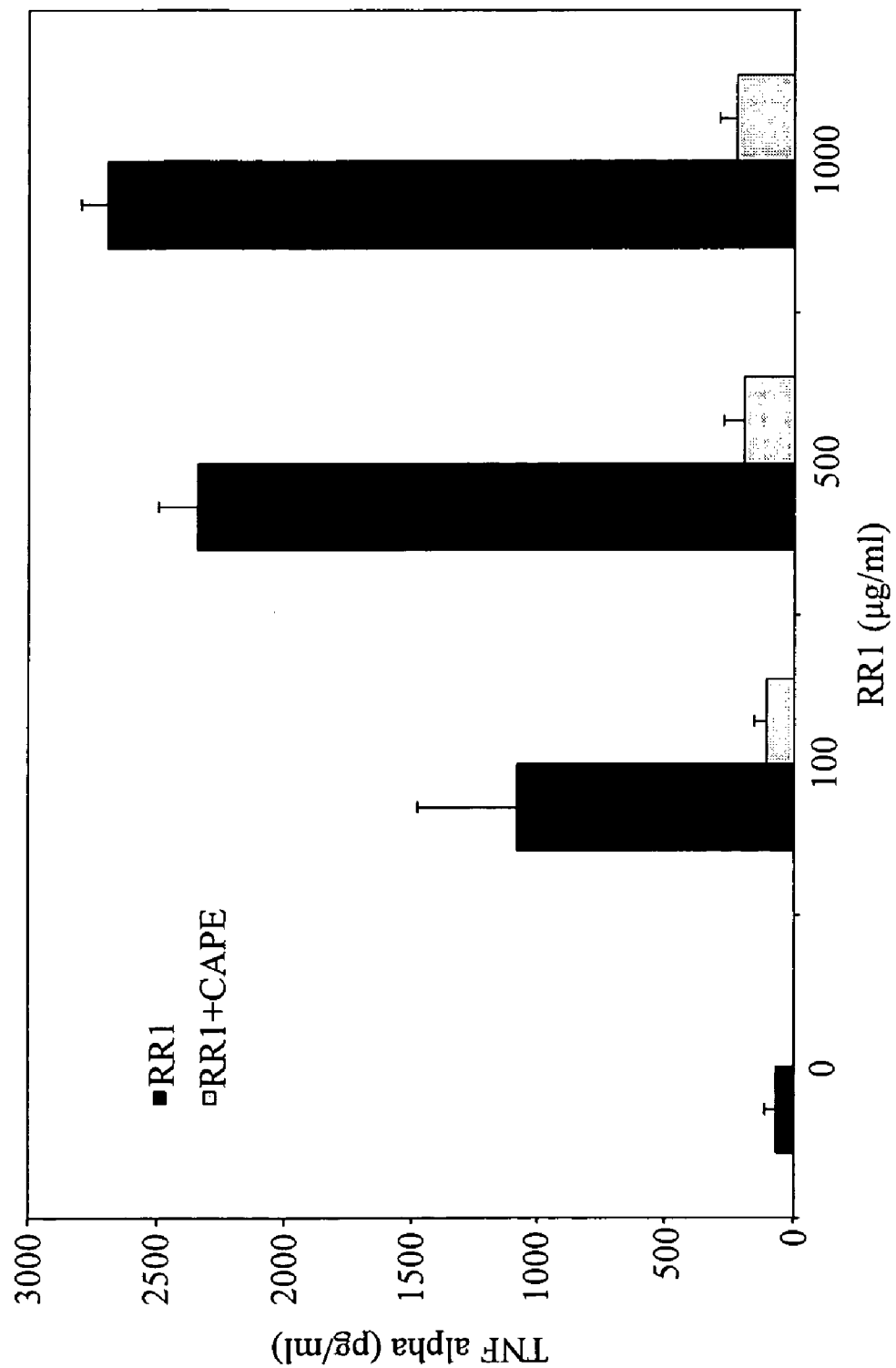
FIG. 12 shows TNF-α synthesis by RAW264.7 cells induced by RR1 in the presence or absence of NF-κB inhibitor caffeic acid phenethyl ester (CAPE). The cells were pre-incubated with 10 μg/ml CAPE for 1 hour in 0.5% FBS containing DMEM medium and replaced with medium containing RR1 at varying concentrations for 4 hour at 37° C. The medium was analyzed for secreted TNF-α using ELISA protocol.

FIG. 12 shows RR1-induced TNF-α synthesis with and without the NF-kB inhibitor, caffeic acid phenethyl ester (CAPE). A dose-dependent increase in the synthesis of TNF-α was evident with escalating RR1 doses. When CAPE was incubated at 10 μg/ml for 1 hour prior to RR1 treatment of monocytes, TNF-α synthesis was completely inhibited in all the concentrations of RR1.

Figure 14:
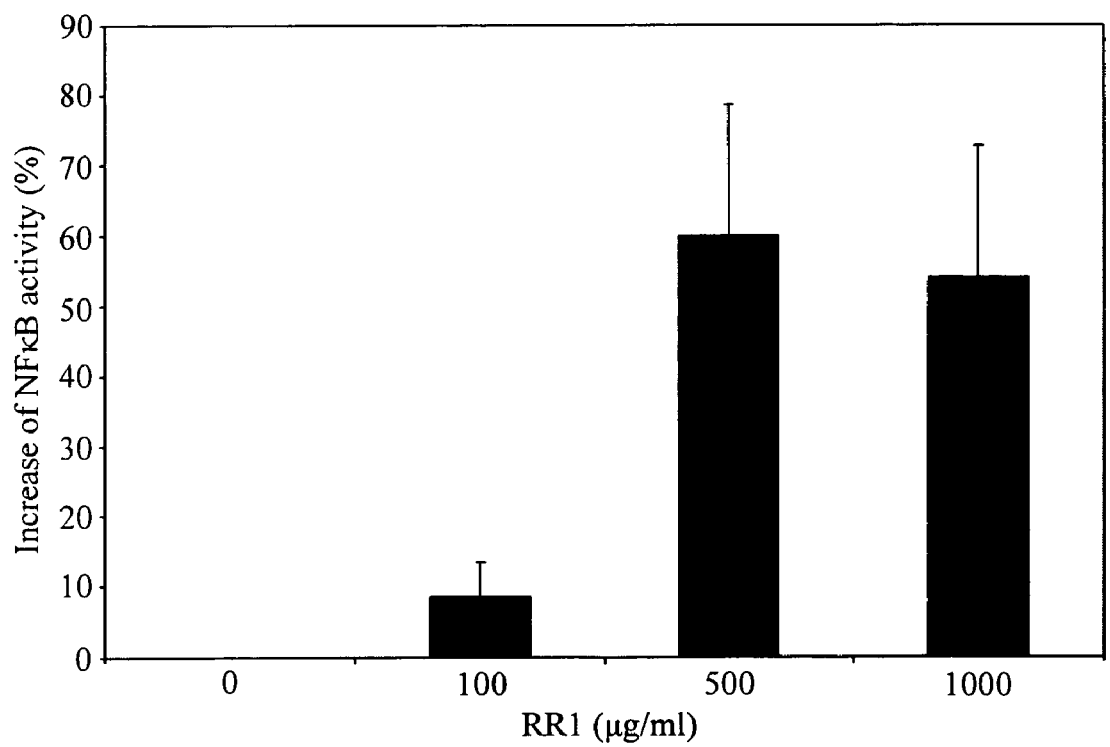
FIG. 14 shows dose-dependent activation of transcription factor NF-κB in RR1 treated RAW264.7 macrophages. NF-κB activity increased with escalating doses of RR1, reaching a plateau at 500 μg/ml.
Figure 13:
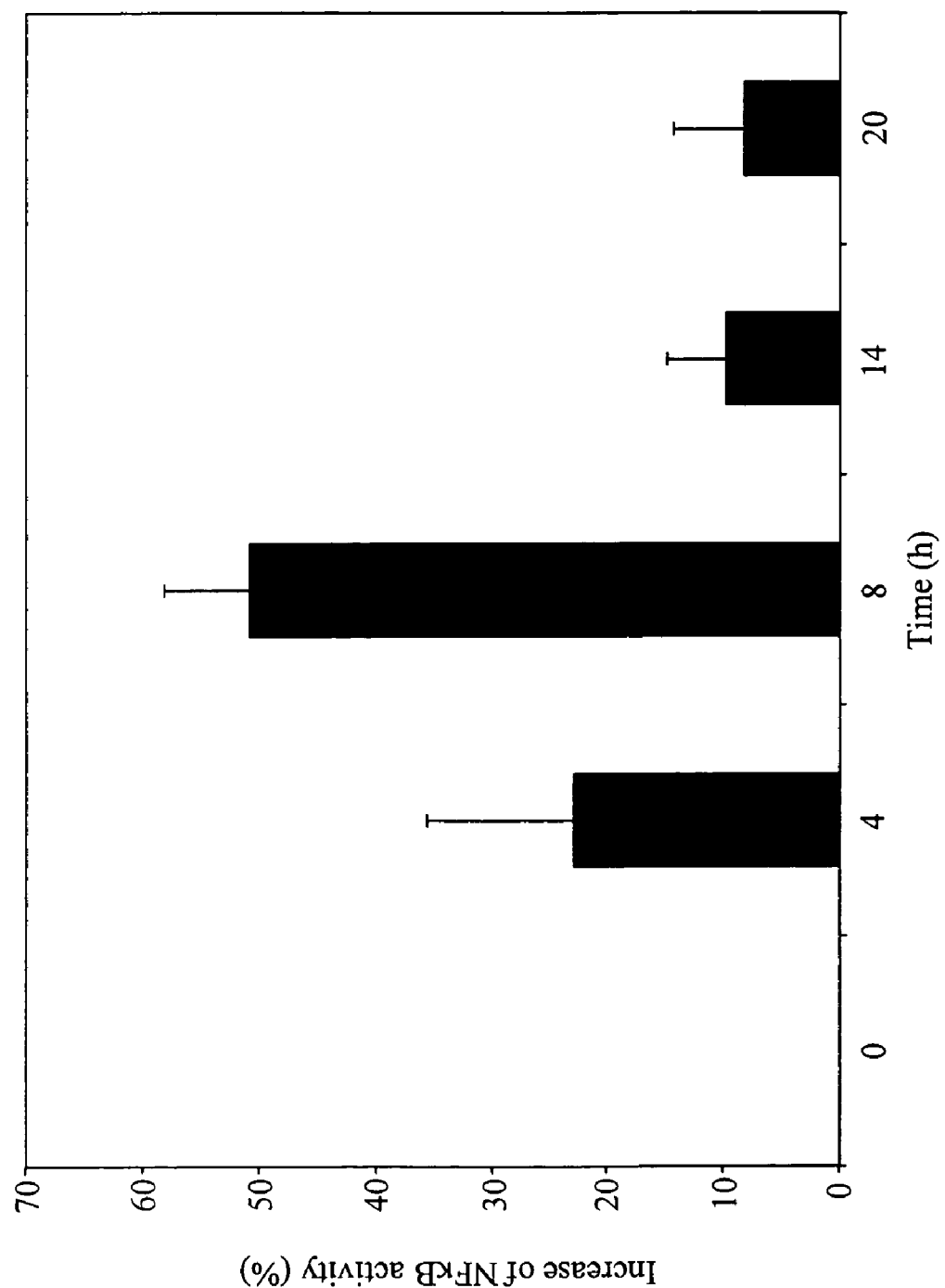
FIG. 13 shows DNA binding activity of transcription factor NF-κB in the RR1-treated RAW 264.7 macrophages over time. The macrophages were treated with 100 μg/ml of RR1 and NF-κB activity of the nuclear extracts analyzed at 2, 4, 8, 14, and 20 hours after incubation using ELISA protocol.
Figure 15:
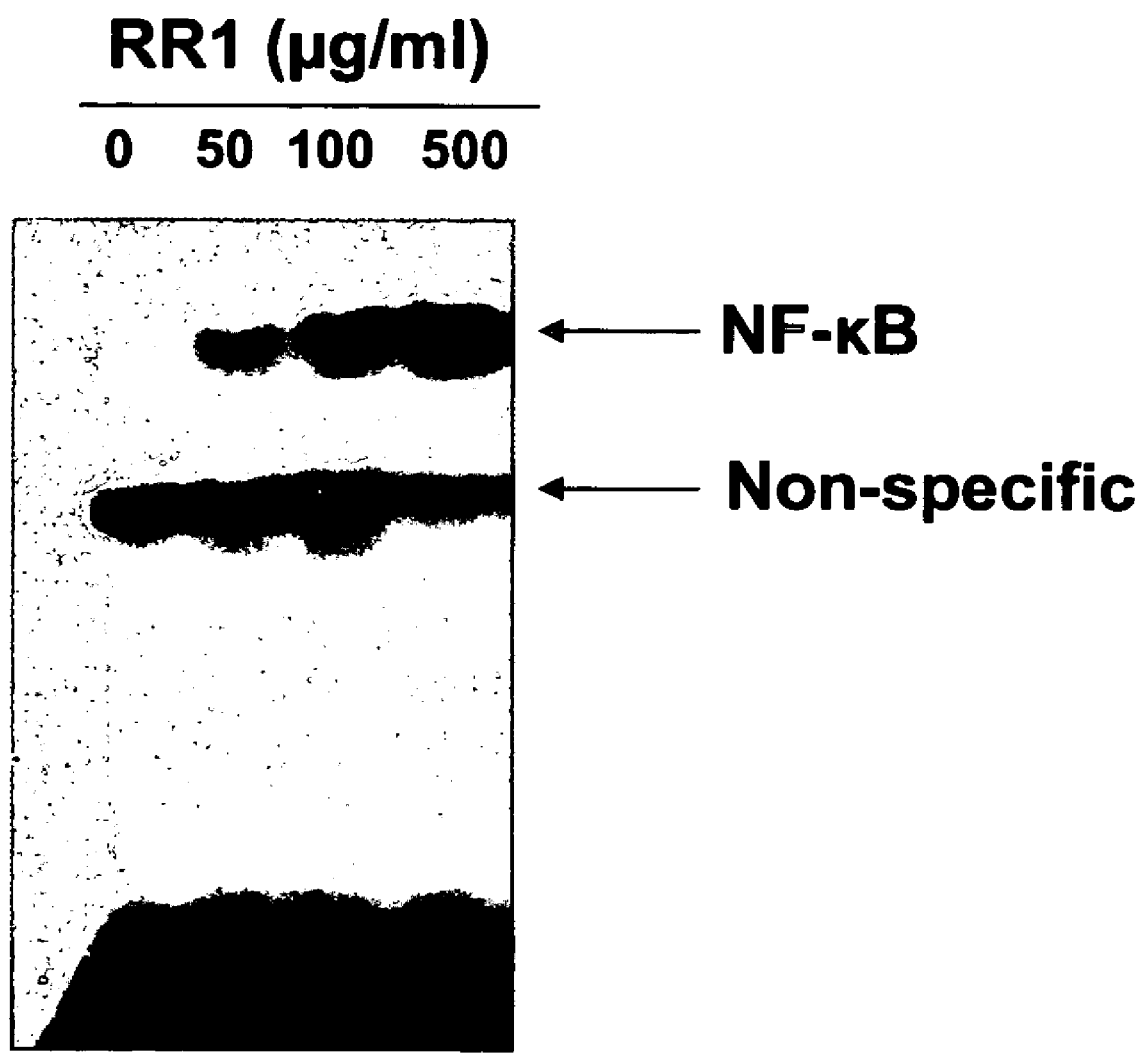
FIG. 15 shows DNA binding activity of transcription factor NF-κB in the nuclear extract of RAW264.7 cells as determined by EMSA gel shift assay. A dose-dependent increase in intensity of NF-κB specific band is visible based on the intensity of non-specific band.

To determine the kinetics of NF-kB activation, the NF-kB activity in RR1-treated macrophages was analyzed at various time intervals using the ELISA protocol (FIG. 13). NF-κB activity increased with time of stimulation, peaked at 8 hours followed by a decrease in the activity later. Based on these results, all further NF-κB activation studies were performed with 8 hours of stimulation and a dose-dependent increase in the NF-κB activity was observed with increasing RR1 concentration and reaching a plateau between 500-1000 μg/ml RR1 doses (FIG. 14). The visualization of the shift in the heterdodimeric band of NF-κB by EMSA corroborates the quantification of the ELISA experiment as evident from the increase in the intensity of the upper band (p65 heterodimeric band) in a concentration dependent manner (FIG. 15).

EXAMPLE 10

IκB-α Degradation

Figures 16, 17:
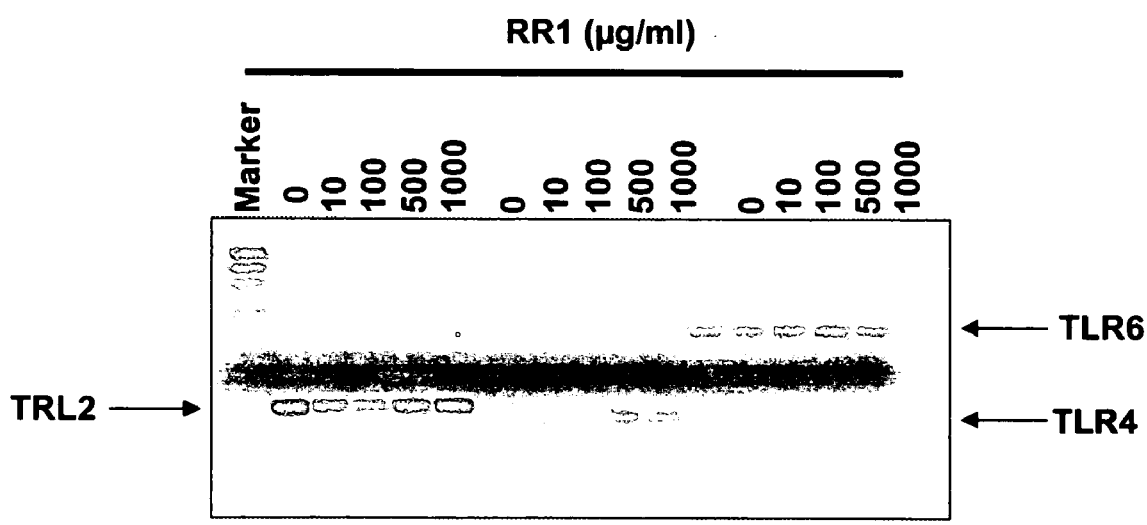
FIG. 16 shows that stimulation of RAW 264.7 macrophages with RR1 induces cytosolic I-κBα degradation. The cells were treated with RR1 at intervals of 15, 30, and 60 minutes. Degradation of I-κBα levels in cytoplasmic lysates was determined by immunoblot analysis using antimouse I-κBα mAb.
FIG. 17 shows RT-PCR of TLR2, TLR4 and TLR6 mRNAs in RAW264.7 cells stimulated with RR1. The cells ($1\times10^6$) were treated with RR1 (0, 10, 100, 500 and 1000 μg/ml) at 37° C. for 24 hours in a $CO_2$ incubator and mRNA amplified with mouse TLR specific primers.

IκB-α phosphorylation and degradation is a pre-requisite for NF-κB activation which facilitate the translocation of NF-κB from cytoplasm to nucleus. The IκB-α western blot shows the results of I-κBα levels for various intervals of stimulation after RR1 treatment. A steady decrease in I-κBα is clear at 30 minutes of RR1 incubation with a complete removal of its expression after 60 minutes of RR1 treatment at 100 μg/ml (FIG. 16).

EXAMPLE 11

TLR mRNAs and Proteins mRNA levels of TLR2, 4 and 6 (FIG. 17) genes remained similar at 0-1000 μg/m RR1 concentrations. Therefore, transcription of TLRs appeared to be not altered by RR1 treatment.

Figure 18:
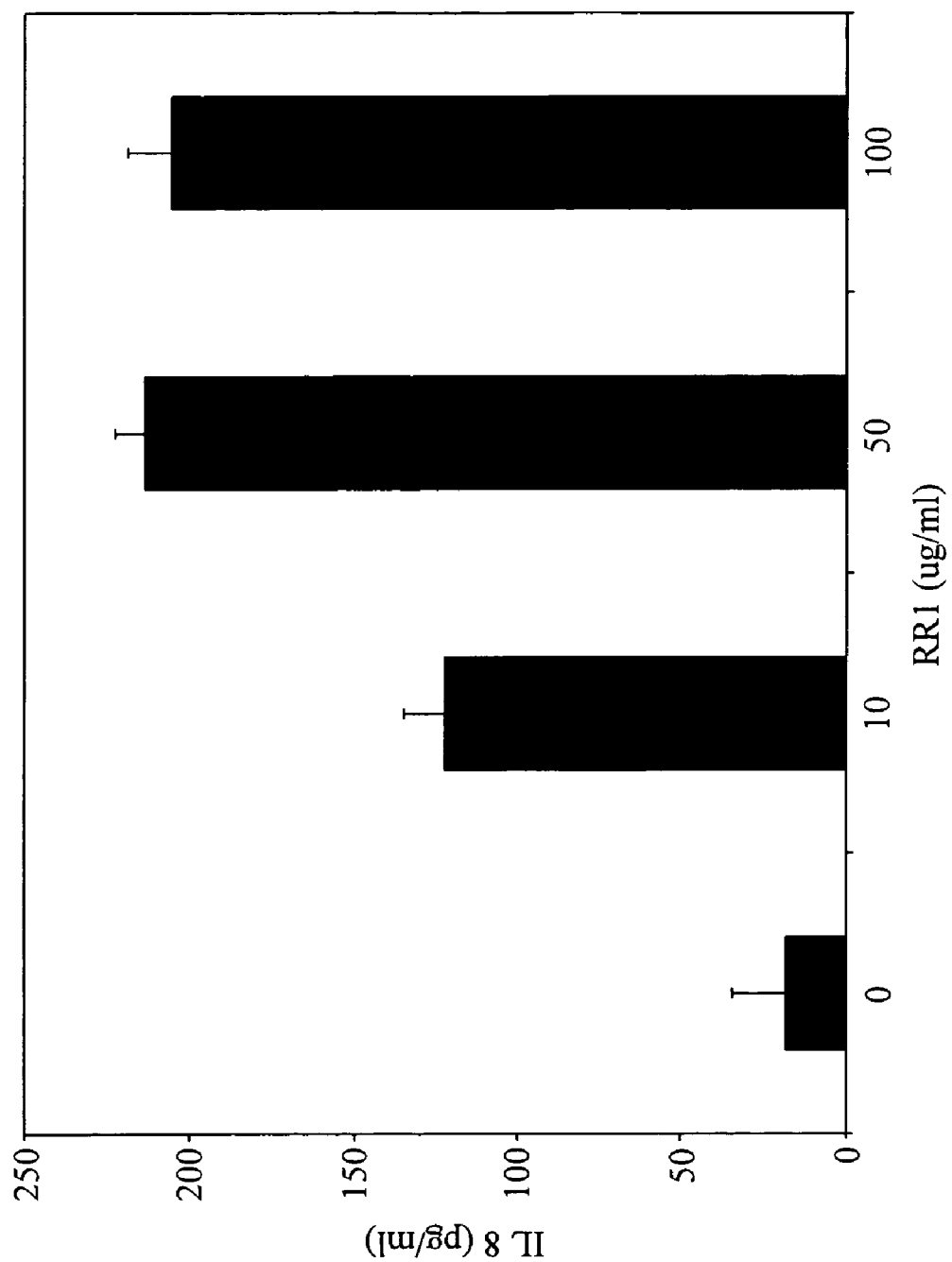
FIG. 18 shows analysis of RR1-induced IL-8 synthesis in HEK293 cells stably transfected with TLR2 and TLR6 genes. HEK293/TLR2/TLR6 cells ($1\times10^6$) were treated with RR1

Role of TLRs in RR1 signaling. To test the roles played by different TLRs on RR1 signaling, parent HEK293 cells were incubated as well as receptor transfectants (TLR2, TLR4/CD14/MD2, TLR6/or TLR2/TLR6) with RR1 and followed the IL-8 production after 24 hours. RR1 did not induce IL-8 production in parental HEK as well as HEK cells transfected with TLR2, or TLR4/CD14/MD2 genes. However, HEK cells transfected with TLR6 as well as TLR2/6 genes showed copious induction of IL-8 and a dose-dependent induction was visible in its synthesis (FIGS. 18 and 19). It is also interesting to note that TLR 2 transfected cells did not produce any IL-8 with RR1 treatment (0-100 μM).

Tinospora cordifolia is a widely used immunostimulating herb in the Ayurvedic (Indian) system of medicine (Chopra, R. N., I. C. Chopra, K. D. Handa, L. D Kanpur (Editors), 1982, Glossary of Indian Medicinal Plants; Council of Scientific an Industrial Research, New Delhi, Dhar VN & Sons, Kolkata, India). The present inventors have described the isolation and characterization of a novel 1,4-α-D-glucan (RR1) from this medicinal herb, which was found to possess immunostimulating properties. This water soluble polysaccharide has (1,4)-α-D-glycosidic linkages in the main chain with (1,6)-α-D-glycosidic-linked side chains at an interval of 6,7 glucose units. To understand further the mechanism of immune system stimulation, this investigation was undertaken. The results described herein show that RR-1 has only little inhibitory effect on the binding and internalization of opsonized zymossan A bioparticles (phagocytosis). This was in contrast of the effect of laminarin, a soluble fungal derived β-glucan which showed about 90% inhibition of zymosan bioparticle internalization (Brown, G. D. et al. *J. Expt. Med.*, 2002, 196:407-412; Czop, J. K. and Austen, K. F. *J. Immunol.*, 1985, 134:2588-2593; Goldman, R. *Exp. Cell Res.*, 1988, 174:481-490).

Complement receptor 3 (CR3) is a heterodimeric transmembrane glycoprotein, belonging to the β2-integrin family, consisting of CD11b non-covalently associated with CD18. Distinct functional domains have been identified in the extracellular portions of the CD11b subunit of CR3 (Diamond, M. S. et al. *J. Cell Biol.*, 1993, 120:1031-1043; Thornton, B. P. et al. *J. Immunol.*, 1996, 156:1235-1246; Lu, C. et al. *J. Biol. Chem.*, 1998, 273:15138-15147; Dana, N. et al. *J. Immunol.*, 1986, 137:3259-3263). In β-glucan signaling, CR3 serves as a leukocyte receptor for particulate (Ross, G. D. et al. *Complement*, 1987, 4:61-74) and soluble glucans (Thornton, B. P. et al. *J. Immunol.*, 1996, 156:1235-1246). This receptor functions as a glucan receptor through COOH terminal lectin site that acts to prime the receptor. It is reported that the I or A domain of CR3 is essential for binding and phagocytosis of C3bi-coated particles (Diamond, M. S. et al. *J. Cell Biol.*, 1993, 120:1031-1043; Dana, N. et al. *J. Immunol.*, 1986, 137:3259-3263) and the lectin domain located C-terminal to the I-domain (Thornton, B. P. et al. *J. Immunol.*, 1996, 156:1235-1246), is responsible for nonopsonic binding properties of CR3 (Balsam, L. B. et al. *J. Immunol.*, 1998, 160:5058-5065; Ross, G. D. et al. *J. Immunol.*, 1985, 134:3307-3315). The ability of polysaccharides to prime CR3 can be mimicked by antibodies that bind near to the lectin site (Thornton, B. P. et al. *J. Immunol.*, 1996, 156:1235-1246). Cabec et al. (Cabec, V. L. et al. *Infect. Immunity*, 2000, 68:4736-4745) showed that under nonopsonic conditions, phagocytosis of zymosan involves distinct molecular determinants of the receptor and that nonopsonic phagocytosis occurs independently of C-terminal lectin site. Brown et al. (Brown, G. D. et al. *J. Expt. Med.*, 2002, 196:407-412) showed inhibition of binding of opsonized zymosan to macrophages with CR3 specific mAb 5C6 and the levels of inhibition were similar to pervious reports (Xia, Y. et al. *J. Immunol.*, 1999, 162:2281-2290). However, inhibition of CR3 with 5C6 mAb failed to inhibit the nonopsonised binding of zymosan particles. The CR3 inhibition experiments with RAW 264.7 cells using anti-CD11b monoclonal antibody showed a 41% reduction in the zymosan-induced TNF-α synthesis under opsonised conditions (37° C.). However, antibody incubation failed to inhibit RR1 induced TNF-α synthesis of RAW264.7 cells under opsonic as well as nonopsonic conditions. Therefore, it appears that CR3 receptor on macrophages may not be involved in the recognition and priming of RR1 leading to the synthesis of cytokines.

Zymosan is a yeast derived particle composed mainly of polysaccharides of which α-glucan and mannan are the major constituents. It has been used as a model for the receptor binding investigations on macrophages employing selective blocking agents specific to receptors. The non-involvement of the β-glucan receptors, CR3 and mannose receptor, in the unopsonized binding of zymosan on mouse macrophages was already demonstrated from the lack of any inhibitory effects to dimethyl glycoside and mannan, respectively (Brown, G. D. et al. *J. Expt. Med.*, 2002, 196:407-412). On the other hand, laminarin, the structurally defined water soluble β-glucan, exhibited very strong inhibition on the nonopsonic binding on macrophages demonstrating the involvement of β-glucan receptors (Brown, G. D. et al. *J. Expt. Med.*, 2002, 196:407-412; Ross, G. D. et al. *Complement*, 1987, 4:61-74). The strong and concentration dependent inhibitory effect of RR1 on the fluorescence of nonopsonised zymosan-FITC particles demonstrates the involvement of same type of receptors in zymosan and RR1 for nonopsonic recognition and binding consistent with the TNF-α production and its blocking by glucan phosphate can inhibit macrophage activation (Ganter, B. N. et al. *J. Expt. Med.*, 2003, 197:1107-1117). The strong inhibitory effect of laminarin on opsonized binding and the consequent TNF-α production can be attributed to the involvement of same type of receptors for the binding and internalization of zymosan particles and laminarin as both have similar molecular pattern and conformation (linear glucose polymers due to the β-glycosidic linkage). On the other hand RR1 is an α-glucan having a different molecular conformation (spiral due to the α-glycosidic linkage) and hence may involve different type of receptors for binding/internalization.

Brown et al. (Brown, G. D. et al. *J. Expt. Med.*, 2002, 196:407-412; Brown, G. D. et al. *J. Exp. Med.*, 2003, 197: 1119-1124; Brown, G. D. and Gordon, S. *Nature*, 2001, 413: 36-37) described the dectin-1 receptor, exclusively responsible for the nonopsonic recognition of zymosan by primary macrophages. These authors showed that dectin-1 mAb 2A11 specific for Dectin-1 receptor can inhibit the binding of unopsonized zymosan in a level comparable with the inhibition obtained with the exogenous β-glucans, glucan phosphate or laminarin, indicating that the mAb is bound at or near the β-glucan binding site. Also Adachi et al. (Adachi, Y. et al. *Infect Immun.*, 2004, 72:4159-71) have recently demonstrated that HEK293 cells transected with mouse dectin-1 cDNA could bind to a gel forming β-glucan, schizophyllan, and the binding can be inhibited by pretreatment with other β-glucans but not by α-glucans demonstrating the specificity of dectin-1 to β-glucans.

To identify further the receptor(s) responsible for priming RR1, RR1-induced cytokine synthesis in HEK 293 cells transfected with various TLRs was investigated. HEK293 cells do not produce TNF-α under polysaccharide stimulation; therefore, other cytokines were analyzed. Since these cells produce IL-8 upon stimulation and also based on the fact that IL-8 production is under the control of NF-kB activation, IL-8 in HEK293-transfectants were analyzed (Wang, Q. et al. *Infect Immun.*, 2001, 69:2270-2276; Torok, A. M. et al. *Infect Immun.*, 2005, 73:1523-1531). TLRs are type I transmembrane proteins and to date 12 members of TLR have been described in humans. HEK293 cells are deficient in these receptors, and it is reported that TLR1, TLR2 and TLR6 are all recruited to phagosomes containing zymosan A particles (Underhill, D. M. et al. *Nature*, 1999, 401:811-815; Ozinsky, A. et al. *Proc. Natl. Acad. Sci. USA.*, 2000, 97:13766-13771). Both TLR2 and TLR6 are required for activation of NF-kB and production of inflammatory cytokines such as TNF-α by zymosan A particles. In the present study RR1 induced IL-8 production in TLR6- as well as TLR2/6-transfected HEK293 cells and not in other transfectants. A dose-dependent increase in the synthesis or IL-8 was also observed. RR1 treatment has not induced any IL-8 induction in TLR2 or TLR4 gene transfected HEK293 cells.

The innate immune system recognizes and responds to diverse microbial products and non-self molecules through TLRs and other receptors of and elicits highly specific responses (Netea, M. G. et al. *Trends Microbiol.*, 2004, 12:484-488). The ligand specificity of the small number of receptors suggest cooperation among them such as homo-/hetero-dimerization, and collaboration with non-TLRs such as CD14, MD2 and Dectin-1 to achieve specificity of the challenges (Ganter, B. N. et al. *J. Expt. Med.*, 2003, 197:1107-1117; Wright, S. D. et al. *Science*, 1990, 252:1321-1322; Medzhitov, R. *Nature Reviews Immunol.*, 2001, 1:135-145; Brown, G. D. and Gordon, S. *Cell. Microbiol.*, 2005, 7:471-479; Shimazu, R. et al. *J Exp Med.*, 1999, 189:1777-1782). Underhill et al. (Underhill, D. M. et al. *Nature*, 1999, 401: 811-815) have demonstrated that particle internalization is not required for the inflammatory response in zymosan induced macrophage activation as the response is mediated by TLRs.

β-glucan studies have shown that NF-κB activation in macrophages is one of the critical steps for the synthesis of cytokines and chemokines leading to immune stimulation (Brown, G. D. et al. *J. Expt. Med.*, 2002, 196:407-412; Brown, G. D. et al. *J. Exp. Med.*, 2003, 197:1119-1124). Non-activated NF-κB is located in the cytoplasm bound to inhibitory protein IκB-α. The IκB-α is phosphorylated and degraded in response to inflammatory stimuli, leading to the activation of NF-κB. The activated NF-κB is translocated from the cytoplasm into the nucleus, where it binds to the promoter regions of target genes and regulates their transcription. When target genes are turned on by NF-κB, mRNA synthesis occurs and protein expression follows. NF-κB activation studies performed in the present study has confirmed that NF-κB activation is the underlying mechanism for the immune system stimulating properties of RR1.

Rel or NFκB protein comprises a family of structurally related eukaryotic transcription factors that are involved in the control of large number of cellular and organizational processes including immune and inflammatory responses and apoptosis in addition to the persistent activation of a number of disease states such as cancer, arthritis, chronic inflammation, asthma, neurodegenerative and heart diseases (Beyaert, R. (ed.), 2004, "Nuclear Factor-kB: Regulation and Role in Disease" Kluwer Academy Publishers Dordrecht, The Netherlands; Ghosh, S. et al. *Annu Rev Immunol.*, 1998, 16:225-260). These proteins are related by a highly conserved DNA binding/dimerization domain called the Rel homology. NF-κB refers to the p50-RelA (p65) heterodimer, the major Rel/NF-κB complex in most cells. The Rel-NF-κB transcription factor bound to 9-10 base pair DNA sites called κB in the dimer. The individual dimers have distinct DNA binding specificities for a collection of related κB sites. The complete inhibition of the TNF-α synthesis with the preincubation of macrophages with CAPE followed by RR1 unequivocally demonstrates the involvement of NF-κB in the cellular signaling pathway of RR1. The CAPE exhibit the inhibition of NF-κB by preventing the translocation of the p65 subunit to the nucleus and the inhibition is specific for the p65 heterodimer translocation (Natarajan, K. et al. *Proc. Natl. Acad. Sci. USA*, 1999, 199693:9090-9095). The concentration dependent NF-κB expression in the ELISA measurements and the NF-κB heterodimeric band in the EMSA gels further confirm the active participation of NF-κB in the transcriptional regulation of cytokine production. The degradation of the IκB-α before the expression of NF-κB expression is an essential requirement for NF-κB activation in the signaling pathway and the degradation of the cytosolic IκB-α within the first 60 minutes of RR1 stimulation justifies the NF-κB pathway. The time course experiments show that the activation of the NF-κB starts after the degradation of IκB-α and reaching a peak at 8 hours of stimulation followed by a decrease. The transient nature of the NF-κB activation is evident from the time course experiment which in turn prevents the continuous and persistent activation of NF-κB and the consequent over production of the inflammatory cytokines.

One of the target genes activated by NF-κB might be that which encodes the IκB-α. The newly synthesized IκB-α enters the nucleus and removes the NF-κB from DNA and export the complex back to the cytoplasm and restore the original latent state and thus prevent the continuous activation. The decrease in the activity of NFκB in the nuclear extract after 8 hours can be attributed to this reverse transportation and thus the NF-κB activation is maintained as a transient process lasting for few hours only.

The cell wall β-glucan from *Pneumocystis carinii* is reported to activate murine macrophages by inducing the translocation of p65 NF-κB heterodimers into the nucleus which takes place in a time-dependent manner detectable as early as at 1 hour of stimulation, peaked between 2-4 hours and began to decrease after 6 hours continuous stimulation (Lebron, F. et al. *J Biol. Chem.*, 2003, 278:25001-25008). Similar studies with LPS resulted in a rapid translocation of the p65 NF-κB in 10-30 mts consistent with an earlier report (O'Connell, M. A. et al. *J. Biol. Chem.*, 1998, 273:30410-30414). However, IκB-α degradation was noticed only after 2 hours of stimulation that completed in 4 hours. In zymosan-stimulated macrophages Young et al. reported the NF-κB activation at 2 hours of stimulation which peaked at 8 hours, and decreased afterwards (Brown, G. D. et al. *J. Expt. Med.*, 2002, 196:407-412). The present inventors have observed almost a similar trend in the kinetics of the NF-κB translocation upon RR1 stimulation that was detected at 4 hours, peaked at 8 hours and decreased upon stimulation for longer period. The IκB-α degradation in the cytosolic extract is observed as early as 30 minutes and completed in 1 hour of stimulation. The difference in the extent and timing of NF-kB translocation into the nucleus compared to LPS or *Pneumocystis carinii* glucan may be one of the contributing factors for the defense properties of RR1 and β-glucan. The slower kinetics of the degradation of the IκB-α and the much slower nuclear translocation of the NF-κB with a prolonged transient period compared to LPS may be contributing to the host defense properties of RR1 and β-glucans; moreover, RR1 stimulation in human leukocytes produces high levels of regulatory cytokine, IL-12 p(40) and anti-inflammatory cytokines IL-10 and MCP-1 as well (Nair, P. K. et al. *Int. Immunopharmacol.*, 2004, 4:1645-1659). In short, these results showed that RR1 stimulates the immune system by activating the macrophages through TLR6 signaling and an NF-kB activation mechanism leading to production of immune proteins. The latent and prolonged activation of NF-kB coupled with sudden I-kBα degradation may differentiate its activation from other activating molecules such as LPS and fungal cell wall glucans.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A pharmaceutical composition comprising an isolated compound having the following chemical structure (I) or a pharmaceutically acceptable salt or analog thereof; and a pharmaceutically acceptable carrier:

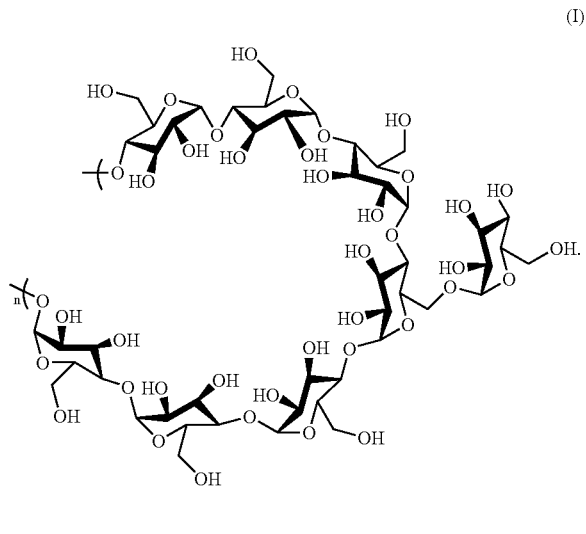

(I)

2. The pharmaceutical composition of claim 1, further comprising an immunomodulatory facilitator.

3. The pharmaceutical composition of claim 1, further comprising an antigen.

4. The pharmaceutical composition of claim 1, further comprising an adjuvant.

5. The pharmaceutical composition of claim 1, further comprising an antigen and an adjuvant.

6. The pharmaceutical composition of claim 1, further comprising an anti-cancer agent.

7. The pharmaceutical composition of claim 1, further comprising a cytotoxic agent.

8. The pharmaceutical composition of claim 1, further comprising a chemotherapeutic agent.

9. The pharmaceutical composition of claim 1, further comprising an immunomodulator selected from the group consisting of tumor necrosis factor (TNF), interferon, nerve growth factor (NGF), platelet derived growth factor (PDGF), and tissue plasminogen activator.

10. The pharmaceutical composition of claim 1, further comprising a biological response modifier selected from the group consisting of lymphokine, interleukin, and growth factor.

11. A method for stimulating an immune response, comprising administering to cells, in vitro or in vivo, an effective amount of a pharmaceutical composition comprising an isolated compound having the following chemical structure (I) or a pharmaceutically acceptable salt or analog thereof; and a pharmaceutically acceptable carrier:

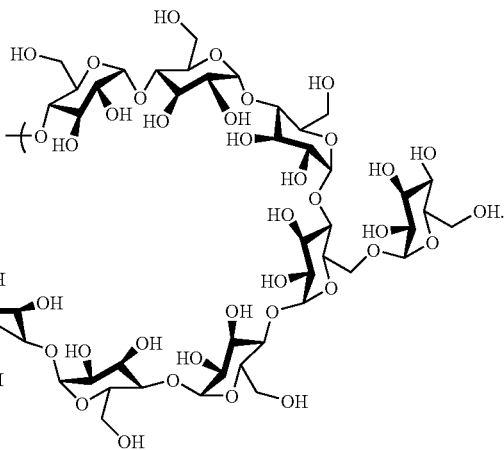

(I)

12. The method of claim 11, wherein the compound is administered to a subject, and wherein the subject's immune system is stimulated by said administering.

13. The method of claim 12, wherein the subject's immune system is stimulated by activation of macrophages.

14. The method of claim 12, wherein the subject's immune system is stimulated in one or more of the following ways:
(a) increase in activation of natural killer (NK) cells;
(b) increase in tumor necrosis factor (TNF)-alpha synthesis in macrophages;
(c) increase in macrophage chemotactic protein (MCP)-1 synthesis;
(d) activation of NF-kB;
(e) increase in Th1 cytokine production; and
(f) increase in level of C3a des Arg of the alternative complement activation pathway.

15. The method of claim 12, wherein the subject is suffering from a cell proliferation disorder.

16. The method of claim 15, wherein the cell proliferation disorder is cancer.

17. The method of claim 12, wherein the subject is suffering from an infection.

18. A process for preparing pharmaceutical composition wherein said process comprises obtaining RR1 from *Tinospora cordifolia* plant material, wherein said process comprises the following steps: (a) providing *Tinospora cordifolia* plant material; (b) extracting an isolated compound having the following chemical structure (I) or a pharmaceutically acceptable salt or analog thereof:

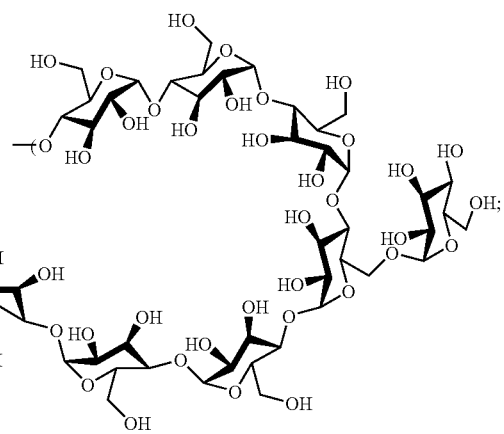

(I)

and (c) mixing the extracted compound with a pharmaceutically acceptable carrier to form a pharmaceutical composition.

19. The pharmaceutical composition, according to claim 1, comprising an isolated compound having the following chemical structure (I) or a pharmaceutically acceptable salt thereof:
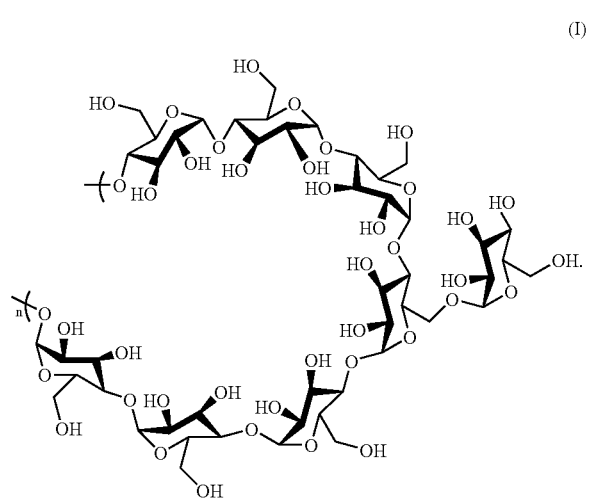
(I)
20. The method, according to claim 11, comprising the administration of an isolated compound having the following chemical structure (I) or a pharmaceutically acceptable salt thereof:
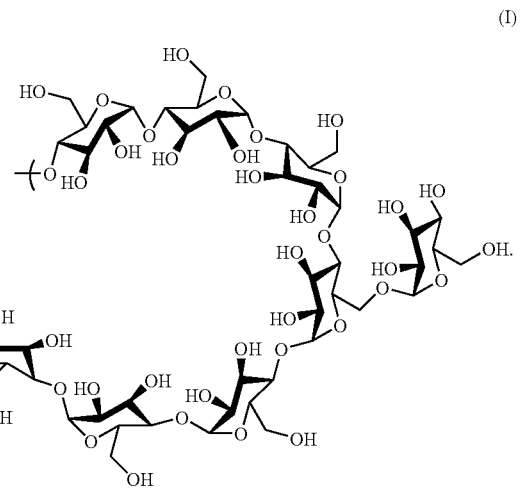
(I)
* * * * *

UNITED STATES PATENT AND TRADEMARK OFFICE
CERTIFICATE OF CORRECTION

| | | |
|---|---|---|
| PATENT NO. | : 7,425,548 B2 | Page 1 of 1 |
| APPLICATION NO. | : 11/178620 | |
| DATED | : September 16, 2008 | |
| INVENTOR(S) | : P. K. Raveendran Nair, Steven J. Melnick and Cheppail Ramachandran | |

It is certified that error appears in the above-identified patent and that said Letters Patent is hereby corrected as shown below:

Column 23,
Line 50, "0.5 m/min." should read --0.5 ml/min.--.

Column 24,
Line 20, "PKE26" should read --PKH26--.

Column 31,
Line 49, "≦21%" should read --≤21%--.

Column 32,
Line 39, "(i.e., the a conformation" should read --(i.e., the α conformation--.

Figure 11:
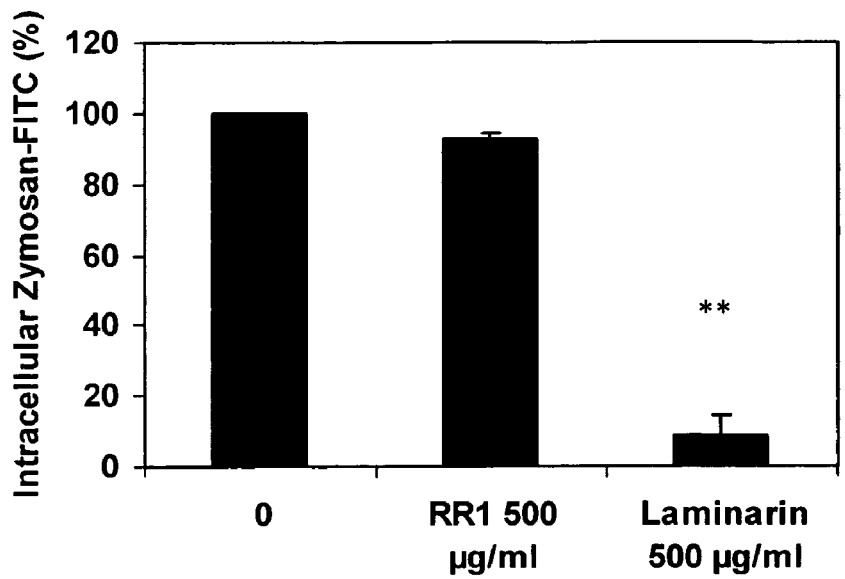
FIG. 11 shows the inhibitory effect of RR1 and laminarin on opsonized binding and internalization (phagocytosis) of FITC-labeled zymosan A bioparticles in RAW264.7 macrophages. Monocytes were incubated with RR1 at 37° C. for 1 hour followed by FITC-labeled zymosan A bioparticles for another 1 hour at 37° C. The cells were washed and intracellular fluorescence measured in a Coulter Elite Flow cytometer.

Column 33,
Line 35, "FIG. 1" should read --Figure 11--.

Column 40,
Line 41, Claim 18, "Preparing pharmaceutical" should read --preparing a pharmaceutical--.

Signed and Sealed this

Thirteenth Day of January, 2009

JON W. DUDAS
*Director of the United States Patent and Trademark Office*